United States Patent
Currie et al.

(10) Patent No.: US 10,618,938 B2
(45) Date of Patent: Apr. 14, 2020

(54) COMPOSITIONS FOR COLON CLEANSING AND THE TREATMENT OF GASTROINTESTINAL DISORDERS

(71) Applicant: Ironwood Pharmaceuticals, Inc., Cambridge, MA (US)

(72) Inventors: Mark G. Currie, Sterling, MA (US); Robert Solinga, Brookline, MA (US); Christopher Leitheiser, Arlington, MA (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/570,838

(22) PCT Filed: Apr. 29, 2016

(86) PCT No.: PCT/US2016/030061
§ 371 (c)(1),
(2) Date: Oct. 31, 2017

(87) PCT Pub. No.: WO2016/178979
PCT Pub. Date: Nov. 10, 2016

(65) Prior Publication Data
US 2018/0148476 A1 May 31, 2018

Related U.S. Application Data

(60) Provisional application No. 62/156,077, filed on May 1, 2015.

(51) Int. Cl.
| | |
|---|---|
| *A61K 38/00* | (2006.01) |
| *C07K 7/08* | (2006.01) |
| *A61K 9/00* | (2006.01) |
| *A61P 1/10* | (2006.01) |
| *A61P 35/00* | (2006.01) |
| *A61K 38/10* | (2006.01) |
| *A61K 38/12* | (2006.01) |
| *A61K 45/06* | (2006.01) |

(52) U.S. Cl.
CPC .............. *C07K 7/08* (2013.01); *A61K 9/0031* (2013.01); *A61K 9/0053* (2013.01); *A61K 38/10* (2013.01); *A61K 38/12* (2013.01); *A61K 45/06* (2013.01); *A61P 1/10* (2018.01); *A61P 35/00* (2018.01); *A61K 38/00* (2013.01)

(58) Field of Classification Search
None
See application file for complete search history.

(56) References Cited

FOREIGN PATENT DOCUMENTS

| WO | WO14131024 | 8/2014 |
| WO | WO16015055 | 1/2016 |

OTHER PUBLICATIONS

Akhter et al. Org. Biomol. Chem., 2009, 7, 1547-1553 | 1547. (cited in ISR).*
Brady et al., "Strategies for the development of conotoxins as new therapeutic leads." Marine drugs 11.7: 2293-2313, 2013.
Hossain et al., "Solid phase synthesis and structural analysis of novel A-chain dicarba analogs of human relaxin-3 (INSL7) that exhibit full biological activity." Organic & biomolecular chemistry 7.8: 1547-1553, 2009.
Pitari, G. M., "Pharmacology and clinical potential of guanylyl cyclase C agonists in the treatment of ulcerative colitis." Drug design, development and therapy 7: 351, 2013.
Safar et al., "The carba-modification of cystine-containing peptides: Synthesis of selectively protected cystathionines and their incorporation into the oxytocin molecule." In Peptides-American Symposium, vol. 13, pp. 119-120. Escom Science Publishers, 1994.
Tam et al., "Disulfide bond formation in peptides by dimethyl sulfoxide, Scope and applications." Journal of the American Chemical Society 113.17: 6657-6662, 1991.
Wu et al.,"Assignment of disulfide bonds in proteins by chemical cleavage and peptide mapping by mass spectrometry." Post-translational Modifications of Proteins. Humana Press, 1-22, 2002.

* cited by examiner

*Primary Examiner* — Jeanette M Lieb
(74) *Attorney, Agent, or Firm* — Honigman LLC; Kelly T. Murphy; Jonathan P. O'Brien

(57) ABSTRACT

The present invention provides peptides and compositions that are useful for the treatment of gastrointestinal disorders or for colon cleansing. The present invention also provides compositions and methods of treating gastrointestinal disorders and pharmaceutical compositions for accomplishing the same. In some embodiments, these pharmaceutical compositions include oral dosage forms.

30 Claims, 27 Drawing Sheets
Specification includes a Sequence Listing.

Figure 1

ACTIVITY AND STABILITY DATA FOR REPRESENTATIVE PEPTIDES

|  | Activity/Potency | | Metabolic Stability |
|---|---|---|---|
|  | cGMP in T84 | GCCA Binding | Diluted in RIF |
| SEQ ID NO:43 | ++ | ++ | ++ |
| SEQ ID NO:47 | +++ | ++ | + |
| SEQ ID NO:62 | ++ | ++ | +++ |
| SEQ ID NO:64 | ++ | ++ | ++ |

KEY (ST=ST CORE)

| Category | Parameter | Fair (+) | Good (++) | Excellent (+++) |
|---|---|---|---|---|
| Activity/ Potency | cGMP in T84 ($EC_{50}$ pH 7) | > 150nM | 50-150nM | <50nM |
|  | GCCA Binding (Mean $IC_{50}$, pH 5-8) | Worse than ST | Similar to ST | Better than ST |
|  | In vivo Pharmacology | Worse than ST | Similar to ST | Better than ST |
| Stability | Metabolic: Diluted Rat Intestinal Fluid (% remaining at 1 hr) | < 50% | 50-75% | 75-100% |

T84 Activity hSTa=NSSNY-ST Core
32-2=SEQ ID NO: 3
32-4=SEQ ID NO: 4
32-9=SEQ ID NO: 5
32-10=SEQ ID NO: 6
32-11=SEQ ID NO: 7

T84 Activity

ST core=ST Core; Peptide 1= SEQ ID NO: 8; Peptide 2= SEQ ID NO: 8; Peptide 3= SEQ ID NO: 9; Peptide 4= SEQ ID NO: 9; Peptide 5= SEQ ID NO: 9; Peptide 6= SEQ ID NO: 10; Peptide 7= SEQ ID NO: 10

Figure 4

T84 Activity

| Peptide Concentration (uM) | nM cGMP | | | | | |
|---|---|---|---|---|---|---|
| | SEQ ID NO: 23 | | SEQ ID NO: 23 | | SEQ ID NO: 24 | |
| 0 | | 1.4 | 1.4 | 4.8 | 0.5 | 3.2 |
| 0.1 | 65.7 | 53.3 | 18.4 | 21.9 | 2.0 | 1.7 |
| 0.3 | 80.4 | 88.5 | 75.6 | 80.1 | 11.2 | 24.9 |
| 1 | 121.3 | 104.0 | 97.9 | 98.0 | 55.1 | 58.7 |
| 3 | 116.8 | 102.7 | 143.1 | 118.5 | 99.3 | 108.2 |
| 10 | 133.2 | 112.0 | 133.6 | 139.9 | 135.7 | 134.5 |

| Peptide Concentration (uM) | nM cGMP | | | | | | |
|---|---|---|---|---|---|---|---|
| | SEQ ID NO: 25 | | SEQ ID NO: 26 | | SEQ ID NO: 27 | | ST core |
| 0 | 1.1 | 2.0 | 1.1 | 1.0 | 1.7 | 1.2 | 0.7 | 0.8 |
| 0.1 | 90.5 | 80.5 | 76.8 | 76.3 | 1.7 | 1.3 | 80.5 | 95.3 |
| 0.3 | 126.5 | 128.5 | 120.4 | 120.0 | 4.7 | 1.0 | 109.5 | 134.1 |
| 1 | 153.2 | 143.2 | 144.3 | 137.1 | 7.5 | 1.6 | 114.6 | 122.4 |
| 3 | 168.6 | 184.3 | 182.7 | 167.6 | 9.8 | 1.1 | 149.4 | 147.3 |
| 10 | 191.3 | 181.3 | 164.2 | 141.9 | 6.9 | 0.2 | 164.0 | 134.2 |

| Peptide Concentration (uM) | nM cGMP | | | |
|---|---|---|---|---|
| | SEQ ID NO: 12 | | SEQ ID NO: 13 | |
| 0.1 | 3.2 | 2.3 | 2.0 | 0.3 |
| 0.3 | 8.9 | 6.4 | 4.8 | 2.3 |
| 1 | 18.8 | 13.5 | 8.5 | 4.5 |
| 3 | 32.5 | 26.8 | 19.0 | 17.6 |
| 10 | 87.0 | 67.0 | 28.0 | 24.3 |

T84 Activity

T84 Activity 354.42.02= SEQ ID NO: 35; 354.42.03F1= SEQ ID NO: 36; 354.42.03F2= SEQ ID NO: 36; 354.42.04F1= SEQ ID NO: 37; 354.42.04F2= SEQ ID NO: 37; 354.42.11= SEQ ID NO: 44; 354.42.12= SEQ ID NO: 39

T84 Activity 354.41.10.1.1= SEQ ID NO: 40
354.41.10.1.2= SEQ ID NO: 40
354.41.10.2= SEQ ID NO: 41
354.44.1= SEQ ID NO: 2
354.44.8.1= SEQ ID NO: 42
354.44.8.2.1= SEQ ID NO: 42
354.44.8.2.2= SEQ ID NO: 42

T84 Activity 354.45.12.1= SEQ ID NO: 43
354.45.12.2= SEQ ID NO: 43

T84 Activity

T84 Activity

T84 Activity 354.44.12=SEQ ID NO:53; 354.43.11= SEQ ID NO: 47; 354.34.9= SEQ ID NO: 12; 354.34.10= SEQ ID NO: 13; 354.40.11= SEQ ID NO: 27; ST=ST Core T84 Activity T84 Activity 354.45.11= SEQ ID NO: 54; 354.45.3= SEQ ID NO: 55; 354.48.11.1= SEQ ID NO: 56; 354.48.11.2= SEQ ID NO: 57; 354.48.12= SEQ ID NO: 58; 354.50.1= SEQ ID NO: 59

T84 Activity 354.51.2= SEQ ID NO: 60; 354.51.4= SEQ ID NO: 61; 454.09.2= SEQ ID NO: 62; 454.09.3= SEQ ID NO: 63; 454.09.4= SEQ ID NO: 64

In Vivo Rat Duodenal Loops

Rat Duodenal Loop Volumes

ST=ST Core

Figure 17
Mouse Gut Transit
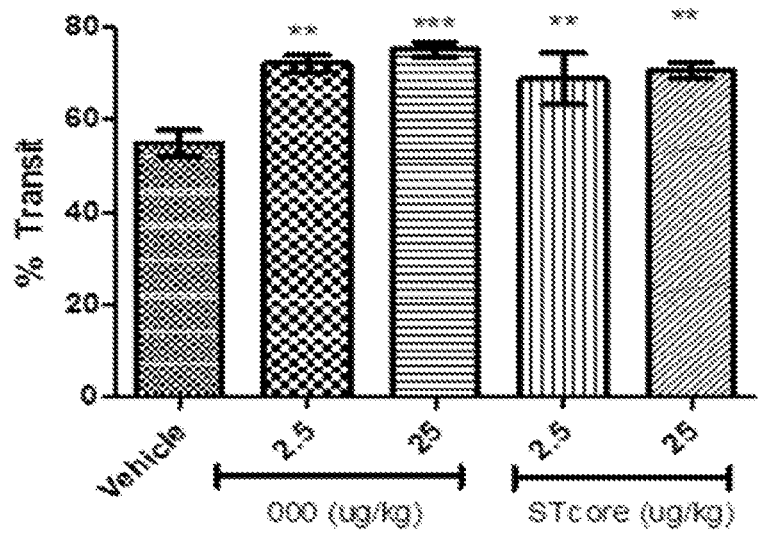
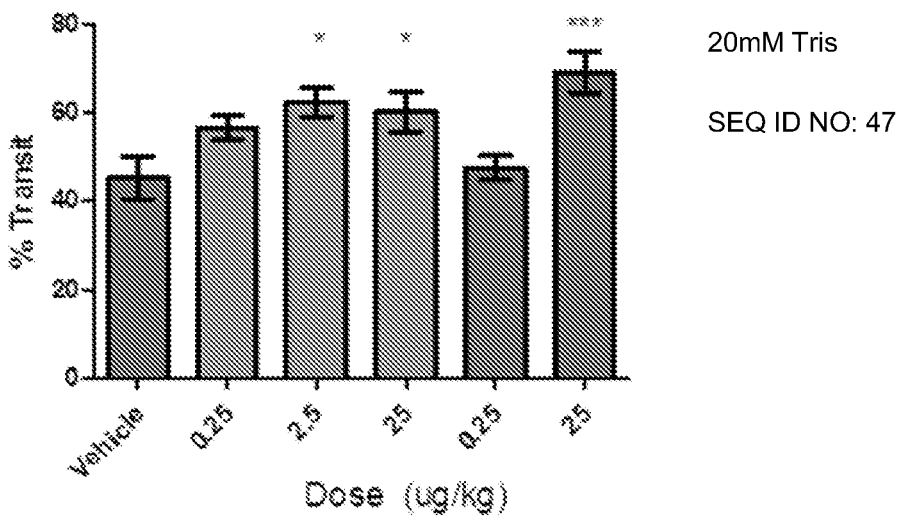

In Vivo Ligated Rat Loops 354.51.7.2= SEQ ID NO: 69
351.55.1= SEQ ID NO: 67

In Vivo Ligated Rat Loop Volumes

Figure 20

In Vitro Rat Intestinal Fluid Metabolism

% Remaining at 1 Hr

| SEQ ID NO: | $[M+2H]^{2+}$ | $[M + 2H]^{2+}$ Metabolite | % remaining of Parent |
|---|---|---|---|
| ST Core | 738.7135 | 657.1815 | 2% |
| SEQ ID NO: 26 | 750.2642 | 669.2245 | 21% |
| SEQ ID NO: 43 | 669.2245 | -- | 74% |
| SEQ ID NO: 53 | 720.2642 | 669.2245 | 3.5% |
| SEQ ID NO: 47 | 720.2642 | 669.2245 | 17% |
| SEQ ID NO: 2 | 719.2563 | 638.2167 | 30% |

Figure 21

In Vitro Rat Intestinal Fluid Metabolism

% Remaining at 1 Hr

| SEQ ID NO: | $[M +H]^{2+}$ | $[M +2H]^{2+}$ Metabolite | % remaining of Parent at 60 min. |
|---|---|---|---|
| ST Core | 738.7135 | 657.1815 | 3.5% |
| SEQ ID NO: 60 | 751.2725 | 670.2329 | 21% |
| SEQ ID NO: 61 | 670.2329 |  | 33% |
| SEQ ID NO: 62 | 760.7547 | 679.7150 | 93% |
| SEQ ID NO: 63 | 760.2508 | 679.2111 | 26% |
| SEQ ID NO: 64 | 679.2111 | -- | 70% |

| SEQ ID NO: | $[M +H]^{2+}$ | % remaining of Parent at 60 min. |
|---|---|---|
| ST Core | 738.7135 | 3.0% |
| SEQ ID NO: 65 | 761.2580 | 110% |
| SEQ ID NO: 66 | 730.2502 | 86% |
| SEQ ID NO: 62 | 760.2504 | 97% |

Figure 22

In Vivo Rat Duodenal Loop Metabolism

| SEQ ID NO: | [M +H]$^{2+}$ | [M +2H]$^{2+}$ Metabolite | % remaining of Parent at 60 min. | % remaining of Metabolite at 60 min. |
|---|---|---|---|---|
| ST Core | 738.7135 | 657.1815 | 0% | 0% |
| SEQ ID NO: 47 | 750.2642 | 669.2245 | 0% | 0% |
| SEQ ID NO: 62 | 760.2504 | 679.2106 | 8.4% | 16.2% |

| SEQ ID NO: | [M +H]$^{2+}$ | % remaining of Parent at 60 min. | % remaining of metabolite at 60 min. |
|---|---|---|---|
| ST Core | 738.7135 | 0% | 0% |
| SEQ ID NO: 67 | 751.2555 | 1.8% | 0.7% |
| SEQ ID NO: 69 | 701.2237 | 16.8% | -- |

Figure 23

| SEQ ID NO: | T84 activity (nM) EC50 ± SEM pH7 (unless stated otherwise) | T84 Binding (pH5,7,8) Ki ± SEM | Metabolism (RIF) @1hr | Metabolism (loops) |
|---|---|---|---|---|
| 2 | 101 ± 14 | pH 5: 3.7 ± 2.0  pH 8: 4.2 ± 2.2 | 30% | |
| 11 | 709 ± 143 | | | |
| 23 | | | 63% | |
| 26 | 62 ± 5 | | 21% | |
| 43 | 52 ± 7 | pH5: 2.9 ± 1.6,  pH7: 3.1 ± 0.27 pH8: 1.1 ± 0.5 | 74% | |
| 47 | 10 ± 1.1 | pH5: 3.4 ± 1.2 pH7: 2.1 ± 0.2  pH8: 1.9 ± 0.7 | 17% | 0% |
| 53 | 110 ± 31 | | 3.50% | |
| 60 | 46 ± 5 | pH 5: 8.6 ± 1.3 pH 8: 1.0 ± 0.8 | 21% | |
| 61 | | | 33% | |
| 62 | 147 ± 11, 87 ± 8 | pH 5: 26.1 ± 15.5 pH8: 4.5 ± 3.7 | 93%, 97.1% | 25% |
| 63 | | | 26% | |
| 64 | 87.5 ± 11 | pH 5: 19.2 ± 6.2  pH8: 2.1 ± 0.9 | 70% | |
| 65 | 141 ± 17 | | 111% | |
| 66 | 30 ± 4 | | 86% | |
| 67 | pH5: 26 ± 8  pH 7: 89 ± 13 pH8: 101 ± 17 | pH 5: 1.6 ± 0.1  pH 8: 1.6 ± 0.5 | 88% | 2.50% |
| 68 | 439 ± 37 | | 85% | |
| 69 | pH 5: 126 ± 32 pH7: 440 ± 146 pH8: 896 ± 99 | pH 5: 4.1 ± 0.4  pH 8: 6.4 ± 1.7 | 101% | 16.8% |
| 70 | 137 ± 33 | | 100% | |
| 71 | 342 ± 27 | | | |
| 75 | 90 | | | |
| 76 | 26 | | | |
| 77 | 27 | | | |
| 78 | 2400, 6400 | | | |
| 79 | 64.4 | | | |
| 80 | 360 | | | |
| 81 | 55 | | | |
| 82 | NA | | | |
| 83 | 574 | | | |
| 84 | 540 | | | |
| 85 | 107 | | | |
| 86 | 766 | | | |

Figure 24
T84 Activity

| Peptide (uM) | nM cGMP | | | | | | | |
|---|---|---|---|---|---|---|---|---|
| | SEQ ID NO:14 | | SEQ ID NO: 14 | | SEQ ID NO: 15 | | SEQ ID NO: 16 | |
| 0 | 3.52 | | 3.02 | | 2.45 | | 2.85 | |
| 0.1 | 13.37 | 12.43 | 4.40 | 3.61 | 5.81 | 7.41 | 9.03 | 12.99 |
| 0.3 | 28.87 | 24.09 | 7.71 | 6.59 | 10.74 | 8.60 | 22.59 | 22.42 |
| 1 | 40.13 | 39.44 | 15.49 | 10.24 | 21.67 | 20.30 | 35.49 | 37.21 |
| 3 | 47.53 | 49.01 | 25.45 | 23.83 | 31.87 | 30.48 | 44.99 | 42.44 |
| 10 | 55.38 | 50.56 | 37.33 | 38.77 | 40.63 | 39.99 | 49.03 | 48.85 |

| Peptide (uM) | nM cGMP | | | | | | | |
|---|---|---|---|---|---|---|---|---|
| | SEQ ID NO: 17 | | SEQ ID NO: 17 | | SEQ ID NO: 18 | | SEQ ID NO: 18 | |
| 0 | 2.64 | | 2.71 | | 3.78 | | 3.17 | |
| 0.1 | 9.48 | 5.98 | 2.91 | 1.97 | 15.37 | 18.81 | 6.46 | 5.99 |
| 0.3 | 20.12 | 12.87 | 3.88 | 3.10 | 20.56 | 27.13 | 13.01 | 9.81 |
| 1 | 21.98 | 26.53 | 6.03 | 7.16 | 26.61 | 35.53 | 21.09 | 21.52 |
| 3 | 34.72 | 32.38 | 12.07 | 10.07 | 34.46 | 35.25 | 32.35 | 29.64 |
| 10 | 39.75 | 41.77 | 19.17 | 22.82 | 34.04 | 43.14 | 36.78 | 27.50 |

| Peptide (uM) | nM cGMP | | | | | | | |
|---|---|---|---|---|---|---|---|---|
| | SEQ ID NO: 19 | | SEQ ID NO: 19 | | SEQ ID NO: 20 | | SEQ ID NO: 20 | |
| 0 | 2.44 | | 0.36 | | 1.39 | | 1.70 | |
| 0.1 | 6.49 | 5.78 | 1.41 | 1.44 | 4.49 | 4.45 | 2.26 | 3.26 |
| 0.3 | 14.41 | 13.44 | 1.72 | 1.97 | 12.81 | 12.63 | 4.63 | 4.84 |
| 1 | 20.46 | 26.43 | 4.02 | 3.83 | 24.47 | 24.71 | 9.63 | 11.92 |
| 3 | 26.52 | 36.77 | 11.32 | 8.76 | 32.01 | 32.42 | 21.21 | 14.73 |
| 10 | 41.07 | 46.15 | 23.18 | 19.98 | 42.60 | 46.61 | 35.77 | 32.19 |

| Peptide (uM) | nM cGMP | | | | | |
|---|---|---|---|---|---|---|
| | SEQ ID NO: 20 | | SEQ ID NO: 21 | | SEQ ID NO: 22 | |
| 0 | 1.76 | | 2.14 | | 5.06 | |
| 0.1 | 1.66 | 3.26 | 6.82 | 8.03 | 8.04 | 12.81 |
| 0.3 | 2.43 | 3.37 | 11.73 | 16.26 | 12.90 | 19.38 |
| 1 | 3.54 | 5.96 | 18.91 | 24.68 | 19.03 | 27.11 |
| 3 | 7.85 | 10.86 | 23.26 | 31.74 | 23.19 | 36.75 |
| 10 | 16.59 | 20.28 | 27.10 | 40.11 | 29.16 | 47.18 |

Figure 26
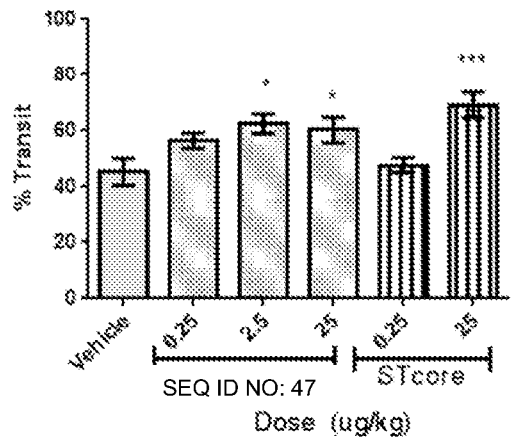
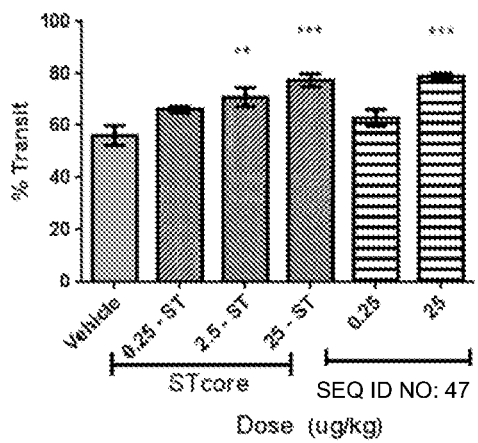

Figure 27
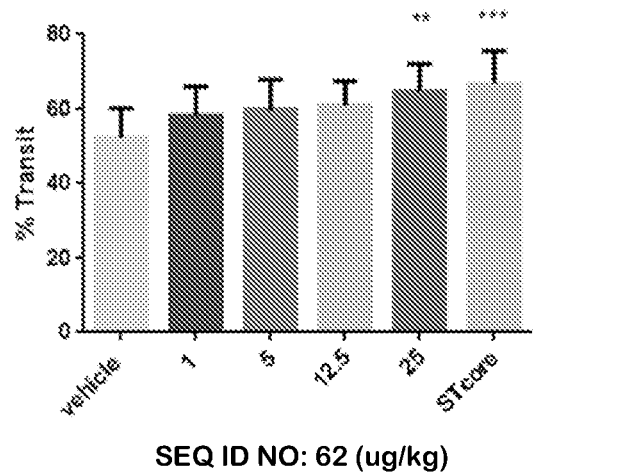
SEQ ID NO: 62 (ug/kg)
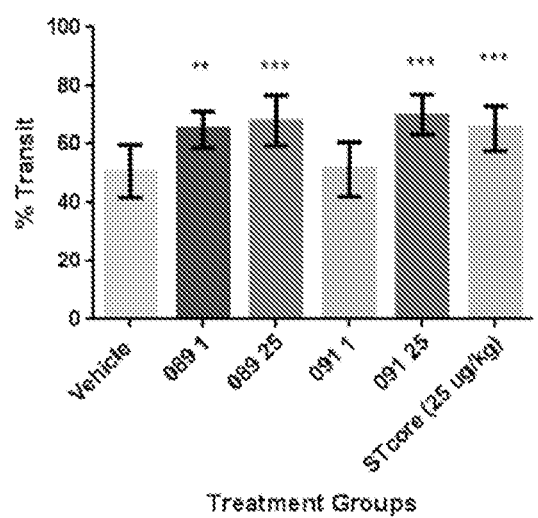
SEQ ID NO: 69 in mGIT Transit
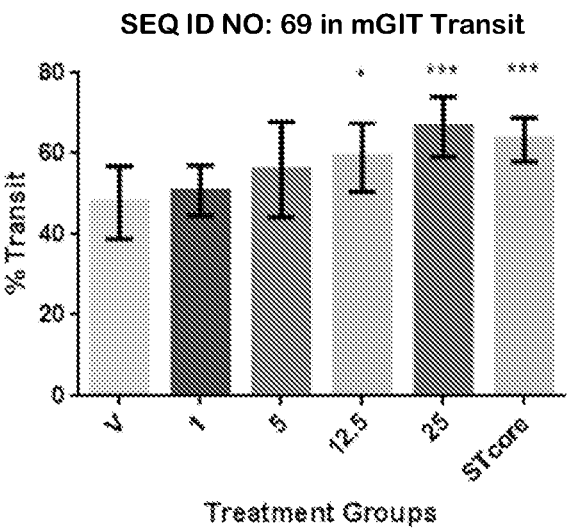

COMPOSITIONS FOR COLON CLEANSING AND THE TREATMENT OF GASTROINTESTINAL DISORDERS

PRIORITY CLAIM

This application is a national phase application of PCT/US2016/030061 filed on Apr. 29, 2016, which claims priority to U.S. Provisional Application Number 62/156,077 filed on May 1, 2015. The entire contents of the aforementioned applications are incorporated herein by reference.

FIELD OF THE INVENTION

This invention relates to peptides, compositions and methods for colon cleansing and treatments of disorders of the gastrointestinal tract and other visceral organs. hereby incorporated by reference.

SEQUENCE LISTING

This application incorporates by reference in its entirety the Sequence Listing entitled "IW154PCT1Sequence_ST25.txt" (45.1 kilobytes) which was created Apr. 28, 2016 and filed electronically herewith.

BACKGROUND

Approximately 15 million colonoscopies are performed annually in the United States, all of which require adequate colon preparation. Inadequate bowel preparation has been reported in about 20% of colonoscopies. Inadequate bowel preparation may result in lower adenoma detection, longer procedural time, and shorter intervals between examinations. As a result, there is a need for safe, effective, and well tolerated colon preparations that allow a broad population of patients to reliably and effectively under go colonoscopies in order to reduce the risk of colon cancer.

SUMMARY

The present invention features peptides, compositions, and related methods for colon cleansing treatments as well as other conditions and disorders are described herein. In one embodiment, the peptides may be used to prepare subjects for colonoscopy treatment. In some embodiments, the peptides or pharmaceutically acceptable salts may be used to prepare subjects for surgery, such as bowel surgery. In other embodiments, the peptides may be used to treat colon cancer, Hereditary Nonpolyposis Colorectal Cancer (HNPCC), i.e. Lynch syndrome, gastroparesis (GP), polyps, pain, general abdominal pain, post-operative ileus, opioid-induced constipation, functional dyspepsia, diverticular disease including but not limited to SUDD (symptomatic uncomplicated diverticular disease) and SCAD (segmental colitis associated with diverticulosis), diverticulosis, diarrhea-predominant irritable bowel syndrome, pain associated with irritable bowel syndrome (IBS), ulcerative colitis, ulcerative proctitis, Crohn's Disease, inflammatory bowel disease (IBD), chronic or acute radiation protopathy, rectal pain, chronic proctalgia, proctalgia fugax, anal pain, chronic anal fissure, post-operative anal pain, overactive bladder syndrome, stress incontinence, interstitial cystitis, bladder pain syndrome, colorectal cancer, pain associated with cancer, general pelvic pain, endometriosis, orchialgia, chronic prostatitis, prostatodynia, vulvodynia, urethral syndrome, penile pain, perianal pain and other gastrointestinal and visceral disorders.

One aspect of the present invention provides a peptide or a pharmaceutically acceptable salt thereof, wherein the peptide comprises the amino acid sequence:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Ala_{15}$ $Xaa_{16}$ $Xaa_{17}$ $Gly_{18}$ $Xaa_{19}$ $Xaa_{20}$ $Xaa_{21}$ (SEQ ID NO: 1), or a pharmaceutically acceptable salt thereof; wherein $Xaa_1$ is BE or is absent;
$Xaa_2$ is BK, Asn or is absent;
$Xaa_3$ is Asn, Ser or is absent;
$Xaa_4$ is Ser or is absent;
$Xaa_5$ is Ser, Asn, Ile, BE or is absent;
$Xaa_6$ is Tyr, Asp, 4-fluorophenylalanine ((4-F)Phe), BK or is absent;
$Xaa_7$ is Cys, cystathionine (Cth), allylglycine (Ag), Hag, or Asp;
$Xaa_8$ is Cys, cystathionine (Cth), penicillamine (Pen), or allylglycine (Ag);
$Xaa_9$ is Glu, Asp, Ser, Thr, or Gln;
$Xaa_{10}$ is Leu, cyclohexylalanine (Cha), Phe, or 4-fluorophenylalanine ((4-F)Phe);
$Xaa_{11}$ is Cys, Ag, or penicillamine (Pen);
$Xaa_{12}$ is Cys, allylglycine (Ag), Hag, Cth, Dpr, or Val;
$Xaa_{13}$ is Asn or Leu;
$Xaa_{14}$ is Pro, Val, sarcosine (Sar), Leu, or Hydroxyproline (OH-Pro);
$Xaa_{16}$ is Cys, Ag, Pen or Cth;
$Xaa_{17}$ is Tyr, Thr, cyclohexylalanine (Cha), 4-fluorophenylalanine ((4-F)Phe), Phe, Ser, or Ala;
$Xaa_{19}$ is Cys, Ag or Pen;
$Xaa_{20}$ is Tyr, Leu, 4-fluorophenylalanine ((4-F)Phe), cyclohexylalanine (Cha), D-Tyr, N-Methyl Tyr (Nme-Tyr) or is absent;
$Xaa_{21}$ is absent or Asn;
wherein at least one Xaa is BE, BK, (4-F)Phe, Cth, Ag, Hag, Pen, Cha, Sar, Dpr, or OH-Pro; and
wherein the peptide contains a covalent bond between $Xaa_7$ and $Xaa_{12}$, $Xaa_8$ and $Xaa_{16}$, and $Xaa_{11}$ and $Xaa_{19}$.

A second aspect of the present invention provides pharmaceutical compositions comprising a peptide of the present invention.

A third aspect of the present invention provides methods for treating a gastrointestinal disorder, which include administering a pharmaceutical composition according to the present invention. The pharmaceutical compositions according to the present invention may be used as a preparation for a colonoscopy, or treatment of gastrointestinal disorders and pain. In some embodiments, the composition is a solid, oral composition.

The details of one or more embodiments of the invention are set forth in the accompanying description.

BRIEF DESCRIPTION OF THE FIGURES

FIG. 1 illustrates the activity and stability results for representative peptides.

FIG. 4 presents the results of a cGMP accumulation in T84 cell assay for analysis of GC-C activity for SEQ ID NOs 12-13 and 23-27.

FIG. 17 illustrates the results of a mouse gut transit (mGIT) assay for SEQ ID NOs 2 and 47 in comparison with the ST Core.

FIG. 20 presents the results of an in vitro rat intestinal fluid (RIF) assay for SEQ ID NOs 2, 26, 43, 47 and 53.

FIG. 21 presents the results of an in vitro RIF assay for SEQ ID NOs 60-66.

FIG. 22 presents the results of an in vivo RIF assay for SEQ ID NOs 47, 62, 67 and 69.

FIG. 23 presents the results of differing assays performed on representative peptides.

FIG. 24 presents the results of a cGMP accumulation in T84 cell assay for SEQ ID NOs 14-22.

FIG. 26 illustrates the results of a mouse gut transit assay for SEQ ID NO 47.

FIG. 27 illustrates the results of a mouse gut transit assay for SEQ ID NOs 62, 67 and 69.

Figure 2:
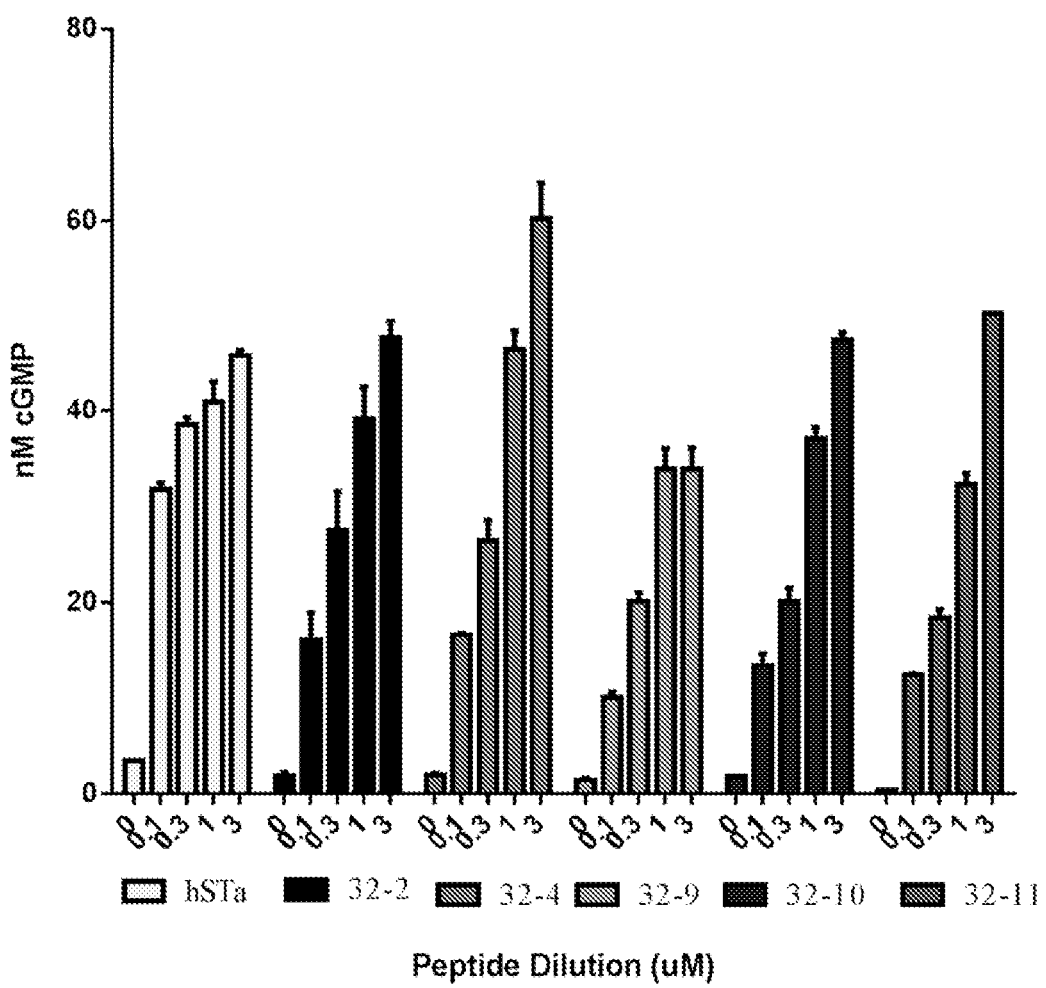
FIG. 2 illustrates the results of a cGMP accumulation in T84 cell assay for analysis of GC-C activity for SEQ ID NOs: 3-7.

These figures are provided by way of example and are not intended to limit the scope of the present invention.

DETAILED DESCRIPTION

Guanylate cyclase C (GC-C) is a transmembrane receptor that is located on the apical surface of epithelial cells in the stomach and intestine. The receptor has an extracellular ligand-binding domain, a single transmembrane region and a C-terminal guanylyl cyclase domain. When a ligand binds to the extracellular domain of GC-C, the intracellular catalytic domain catalyzes the production of cGMP from GTP. In vivo, this increase in intracellular cGMP initiates a cascade of events that leads to increased secretion of chloride and bicarbonate into the intestinal lumen, increased luminal pH, decreased luminal sodium absorption, increased fluid secretion, and acceleration of intestinal transit. cGMP, which is secreted bidirectionally from the epithelium into the mucosa and lumen, has also been shown to dampen afferent C fiber firing, suggesting a potential mechanism for the observed analgesic effects of GC-C agonists on visceral pain.

Linaclotide, a peptide GC-C agonist that is orally administered and currently approved in the United States for the treatment of irritable bowel syndrome with constipation (IBS-c) and chronic idiopatheic constipation (CIC), has numerous effects on lower GI physiology including: (1) reduced visceral pain, (2) reduced bloating, and (3) increased GI transit, which can lead to increased stool frequency and improved stool consistency. Orally administered linaclotide acts locally by activating GC-C receptors at the luminal surface. Thus, the results from clinical trials of linaclotide, as well as preclinical studies that have been done with linaclotide and related peptides, suggest that GC-C peptide agonists may be used therapeutically. The peptides described and claimed herein may bind and activate the GC-C receptor or may be characterized as GC-C peptide agonists.

Definitions

As used herein, C12 is C12 alkyl carboxylic acid, C14 is C14 alkyl carboxylic acid, C16 is C16 alkyl carboxylic acid, C18 is C18 alkyl carboxylic acid, (4-F)Phe is 4-fluorophenylalanine, Cth is cystathionine, Ag is allylglycine, Hag is allylglycine with a reduced dicarba bond, Pent is pentenoic acid, Pen is penicillamine, Cha is cyclohexylalanine, Sar is sarcosine, OH-Pro is hydroxyproline, Nme-Tyr is N-methyl tyrosine, 4-Mepip is 1-methyl-piperidine-4-carboxylic acid, Dpr is di-aminopropionic acid, BE is glutamic acid wherein the side chain carboxylic acid forms the peptide linkage, and BK is lysine wherein the side chain amine forms the peptide linkage. An example of a BE BK bonding pattern would be:

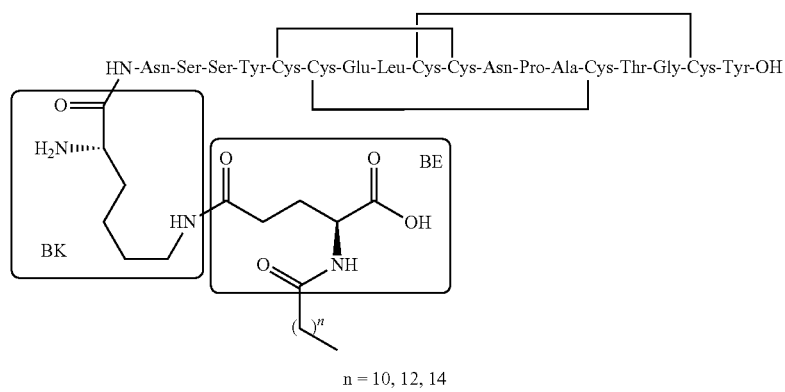
Additional examples of peptide bonding include without limitation:
I.
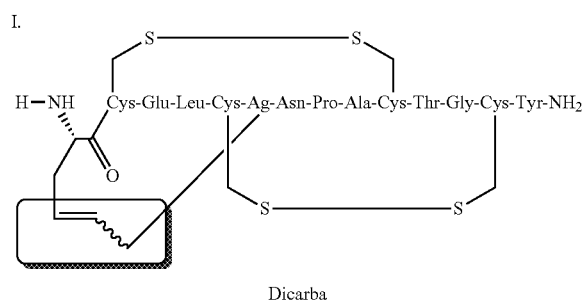
Dicarba
II.
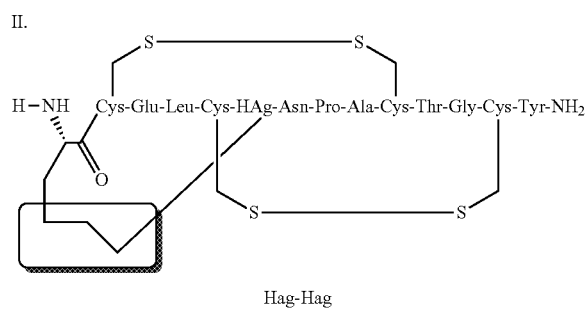
Hag-Hag
III.
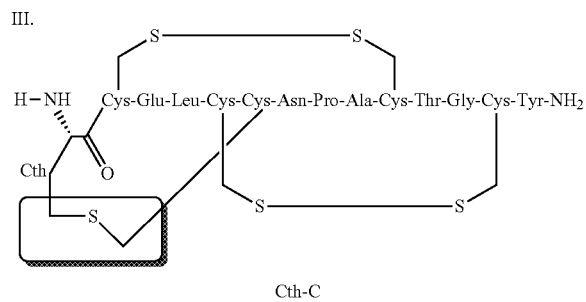
Cth-C IV.
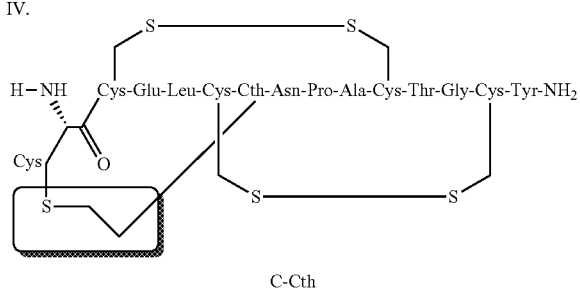
C-Cth
V.
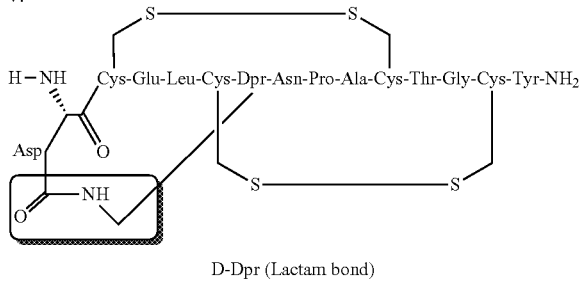
D-Dpr (Lactam bond)
VI.
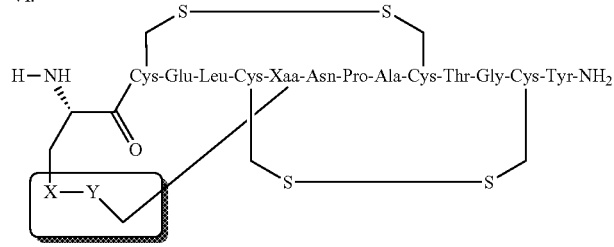
X = CH, Y = CH
X = CH$_2$, Y = CH$_2$
X = CH$_2$, Y = S
X = S, Y = CH$_2$
X = CO, Y = NH
others
X = Se, Y = Se
X = CH$_2$, Y = Se
X = Se, Y = CH$_2$
X = CH$_2$, Y = O
X = O, Y = CH$_2$
X = NH, Y = CO
VII.
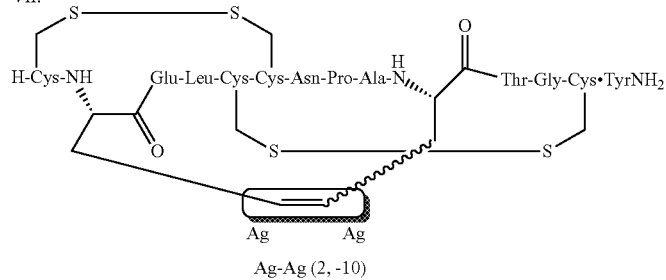
Ag-Ag (2, -10)

-continued
VIII.
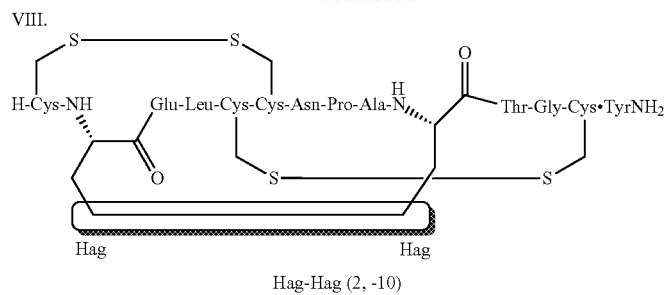
Hag-Hag (2, -10)
IX.
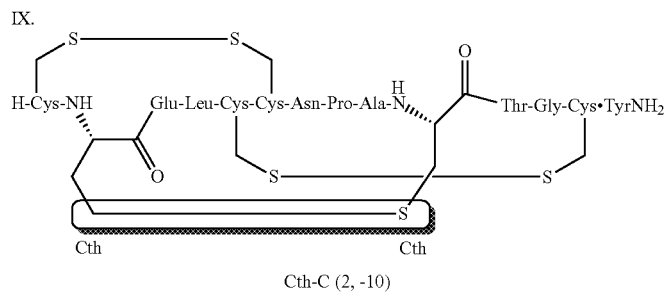
Cth-C (2, -10)
X.
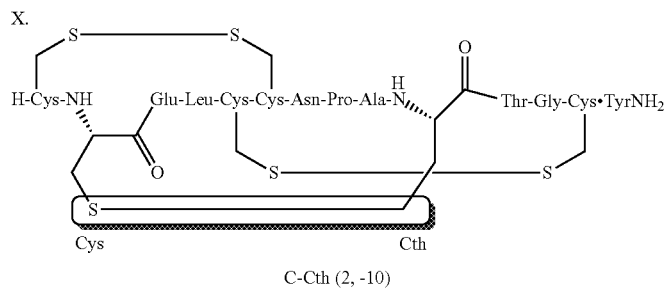
C-Cth (2, -10)
XI.
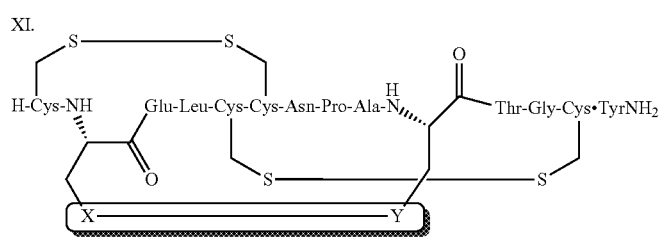
(2, -10)
X = CH, Y = CH
X = CH$_2$, Y = CH$_2$
X = CH$_2$, Y = S
X = S, Y = CH$_2$
others
X = Se, Y = Se
X = CH$_2$, Y = Se
X = Se, Y = CH$_2$
X = CH$_2$, Y = O
X = O, Y = CH$_2$
X = CO, Y = NH
X = NH, Y = CO
XII.
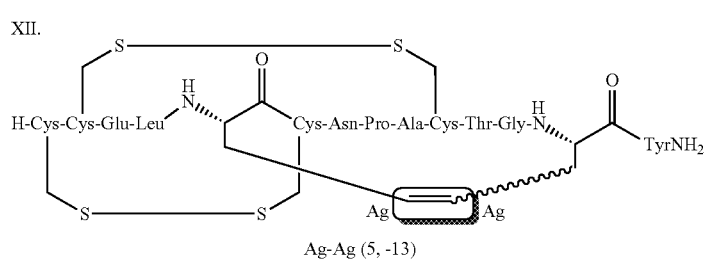
Ag-Ag (5, -13)

XIII.

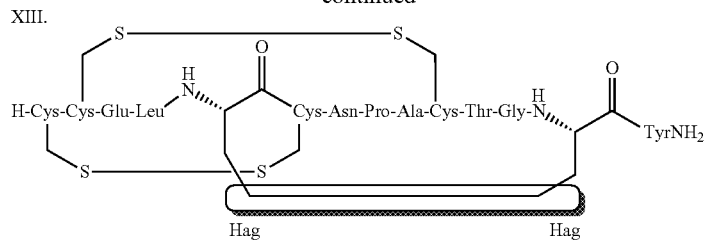

Hag-Hag (5, -13)

XIV.

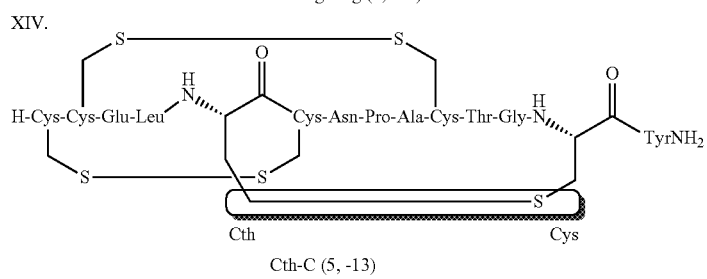

Cth-C (5, -13)

XV.

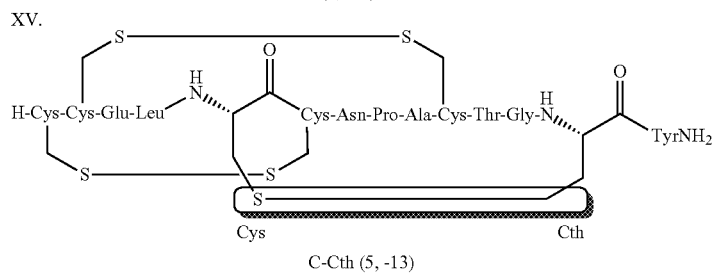

C-Cth (5, -13)

XVI.

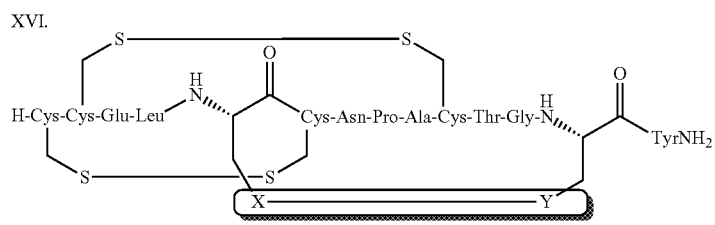

(5, -13)
X = CH, Y = CH
X = CH$_2$, Y = CH$_2$
X = CH$_2$, Y = S
X = S, Y = CH$_2$
others
X = Se, Y = Se
X = CH$_2$, Y = Se
X = Se, Y = CH$_2$
X = CH$_2$, Y = O
X = O, Y = CH$_2$
X = CO, Y = NH
X = NH, Y = CO Peptides In one aspect, the present invention provides a peptide or a pharmaceutically acceptable salt thereof useful for the methods described herein, wherein the peptide comprises the amino acid sequence:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Ala$_{15}$ Xaa$_{16}$ Xaa$_{17}$ Gly$_{18}$ Xaa$_{19}$ Xaa$_{20}$ Xaa$_{21}$ (SEQ ID NO: 1), or a pharmaceutically acceptable salt thereof; wherein Xaa$_1$ is BE or is absent;
Xaa$_2$ is BK, Asn or is absent;
Xaa$_3$ is Asn, Ser or is absent;
Xaa$_4$ is Ser or is absent;
Xaa$_5$ is Ser, Asn, Ile, BE or is absent;
Xaa$_6$ is Tyr, Asp, 4-fluorophenylalanine ((4-F)Phe), BK or is absent;
Xaa$_7$ is Cys, cystathionine (Cth), allylglycine (Ag), Hag, or Asp;
Xaa$_8$ is Cys, cystathionine (Cth), penicillamine (Pen), or allylglycine (Ag);
Xaa$_9$ is Glu, Asp, Ser, Thr, or Gln;
Xaa$_{10}$ is Leu, cyclohexylalanine (Cha), Phe, or 4-fluorophenylalanine ((4-F)Phe);
Xaa$_{11}$ is Cys, Ag, or penicillamine (Pen);

Xaa$_{12}$ is Cys, allylglycine (Ag), Hag, Cth, Dpr, or Val;
Xaa$_{13}$ is Asn or Leu;
Xaa$_{14}$ is Pro, Val, sarcosine (Sar), Leu, or Hydroxyproline (OH-Pro);
Xaa$_{16}$ is Cys, Ag, Pen or Cth;
Xaa$_{17}$ is Tyr, Thr, cyclohexylalanine (Cha), 4-fluorophenylalanine ((4-F)Phe), Phe, Ser, or Ala;
Xaa$_{19}$ is Cys, Ag or Pen;
Xaa$_{20}$ is Tyr, Leu, 4-fluorophenylalanine ((4-F)Phe), cyclohexylalanine (Cha), D-Tyr, N-Methyl Tyr (Nme-Tyr) or is absent;
Xaa$_{21}$ is absent or Asn;
wherein at least one Xaa is BE, BK, (4-F)Phe, Cth, Ag, Hag, Pen, Cha, Sar, Dpr, or OH-Pro; and
wherein the peptide contains a covalent bond between Xaa$_7$ and Xaa$_{12}$, Xaa$_8$ and Xaa$_{16}$, and Xaa$_{11}$ and Xaa$_{19}$.

In some embodiments, the N-terminus of the peptide is acetylated or modified at the N-terminus to provide added stability to the peptide. In other embodiments, the N-terminus is capped with pentenoic acid, biotin, 4-Mepip (1-methyl-4-carboxylic acid), C12 alkyl carboxylic acid, C14 alkyl carboxylic acid, C16 alkyl carboxylic acid, or C18 alkyl carboxylic acid. In some embodiments, the C=C double bond of the pentenoic acid may be cyclized with another C=C double bond to form a dicarba bond.

In some embodiments, the C-terminus of the peptide is amidated or modified at the C-terminus to provide added stability to the peptide.

In yet another embodiment, the N-terminus of the peptide is acetylated or capped and the C-terminus is amidated.

In some embodiments, dicarba bonds (CH$_2$—CH=CH—CH$_2$) or other covalent bonds described herein between peptide residues may be useful in stabilizing the peptide. The dicarba bond and other covalent bonds described herein may in some instances provide greater stability of the peptide than a disulfide bond. In some embodiments, the dicarba bonds may be reduced (CH$_2$—CH$_2$—CH$_2$—CH$_2$).

In some embodiments, the enhanced stability of the peptides allows for storage at room temperature for extended periods of time.

In some embodiments, Xaa$_7$ and Xaa$_{12}$ are both Ag and a dicarba bond is present between Ag$_7$ and Ag$_{12}$; Xaa$_7$ and Xaa$_{12}$ are both Cys and a disulfide bond is present between Cys$_7$ and Cys$_{12}$; Xaa$_8$ and Xaa$_{16}$ are both Cys and a disulfide bond is present between Cys$_8$ and Cys$_{16}$; Xaa$_{11}$ and Xaa$_{19}$ are both Cys and a disulfide bond is present between Cys$_{11}$ and Cys$_{19}$; or any combination thereof.

In other embodiments, Xaa$_7$ is Cth, Xaa$_{12}$ is Cys and a bond is present between Cth$_7$ and Cys$_{12}$; Xaa$_8$ is Cth, Xaa$_{16}$ is Cys and a bond is present between Cth$_8$ and Cys$_{16}$; or any combination thereof.

In some embodiments, Xaa$_7$ is allylglycine or Cys.
In some embodiments, Xaa$_8$ is Cys or cystathionine.
In some embodiments, Xaa$_9$ is Glu.
In some embodiments, Xaa$_{10}$ is Leu.
In some embodiments, Xaa$_{12}$ is Cys or allylglycine.
In some embodiments, Xaa$_{14}$ is Val or Pro.
In some embodiments, Xaa$_{17}$ is Tyr or Thr.
In some embodiments, Xaa$_{20}$ is Tyr or is absent.
In some embodiments, Xaa$_{21}$ is absent.
In some embodiments, Xaa$_1$ is absent; Xaa$_2$ is absent; Xaa$_3$ is absent; Xaa$_4$ is absent; Xaa$_5$ is absent; Xaa$_6$ is absent; Xaa$_7$ is Ag, Cys, or Cth; Xaa$_8$ is Cys or Cth; Xaa$_9$ is Glu; Xaa$_{10}$ is Leu; Xaa$_{12}$ is Ag or Cys; Xaa$_{14}$ is Val or Pro; Xaa$_{17}$ is Tyr or Thr; and Xaa$_{20}$ is Tyr or is absent.
In some embodiments, Xaa$_{14}$ is not Pro.
In some embodiments, Xaa$_{17}$ is not Phe.

In some embodiments, a peptide or pharmaceutically acceptable salt thereof is provided, wherein the peptide comprises the amino acid sequence:

(SEQ ID NO: 2)
H-Ag Cys Glu Leu Cys Ag Asn Pro Ala Cys Thr Gly Cys Tyr-NH$_2$;

(SEQ ID NO: 3)
C12-BE BK Asn Ser Ser Tyr Cys Cys Glu Leu Cys Cys Asn Pro Ala Cys Thr Gly Cys Tyr-NH$_2$;

(SEQ ID NO: 4)
C16-BE BK Asn Ser Ser Tyr Cys Cys Glu Leu Cys Cys Asn Pro Ala Cys Thr Gly Cys Tyr-NH$_2$;

(SEQ ID NO: 5)
C12-BE BK Asn Ser Ser Tyr Cys Cys Glu Leu Cys Cys Asn Pro Ala Cys Thr Gly Cys Tyr-COOH;

(SEQ ID NO: 6)
C14-BE BK Asn Ser Ser Tyr Cys Cys Glu Leu Cys Cys Asn Pro Ala Cys Thr Gly Cys Tyr-COOH;

(SEQ ID NO: 7)
C16-BE BK Asn Ser Ser Tyr Cys Cys Glu Leu Cys Cys Asn Pro Ala Cys Thr Gly Cys Tyr-COOH;

(SEQ ID NO: 8)
H-Cys Ag Glu Leu Cys Cys Asn Pro Ala Ag Thr Gly Cys Tyr-NH$_2$;

(SEQ ID NO: 9)
H-Asn Asp Asp Ag Glu Leu Cys Val Asn Val Ala Ag Thr Gly Cys Leu-NH$_2$;

(SEQ ID NO: 10)
H-Asn Asp Asp Cys Glu Leu Ag Val Asn Val Ala Cys Thr Gly Ag Leu-NH$_2$;

(SEQ ID NO: 11)
C18-BE BK Asn Ser Ser Tyr Cys Cys Glu Leu Cys Cys Asn Pro Ala Cys Thr Gly Cys Tyr-COOH;

(SEQ ID NO: 12)
H-Ag Cys Glu Leu Cys Ag Asn Pro Ala Cys Thr Gly Cys-NH$_2$;

(SEQ ID NO: 13)
H-Ag Cys Glu Leu Cys Ag Asn Pro Ala Cys Ala Gly Cys-NH$_2$;

(SEQ ID NO: 14)
H-Ag Cys Glu Phe Cys Ag Asn Pro Ala Cys Thr Gly Cys Tyr-NH$_2$;

(SEQ ID NO: 15)
H-Ag Cys Glu (4-F)Phe Cys Ag Asn Pro Ala Cys Thr Gly Cys-NH$_2$;

(SEQ ID NO: 16)
H-Ag Cys Glu (4-F)Phe Cys Ag Asn Pro Ala Cys Thr Gly Cys Tyr-NH$_2$;

-continued

```
                                        (SEQ ID NO: 17)
H-Ag Cys Glu (4-F)Phe Cys Ag Asn Pro Ala Cys

Thr Gly Cys (4-F)Phe-NH2;

(SEQ ID NO: 18)
H-Cys Cys Glu Leu Ag Cys Asn Pro Ala Cys Thr

Gly Ag Tyr-NH2;

(SEQ ID NO: 19)
H-Ag Cys Glu Phe Cys Ag Asn Pro Ala Cys Thr

Gly Cys-NH2;

(SEQ ID NO: 20)
H-Ag Cys Glu Phe Cys Ag Asn Pro Ala Cys Thr

Gly Cys (4-F)Phe-NH2;

(SEQ ID NO: 21)
H-Cys Cys Glu (4-F)Phe Cys Cys Asn Pro Ala Cys

Thr Gly Cys Tyr-NH2;

(SEQ ID NO: 22)
H-Cys Cys Glu (4-F)Phe Cys Cys Asn Pro Ala Cys

Thr Gly Cys (4-F)Phe-NH2;

(SEQ ID NO: 23)
H-Ag Cys Glu Leu Cys Ag Asn Pro Ala Cys Thr Gly

Cys (4-F)Phe-NH2;

(SEQ ID NO: 24)
H-(4-F)Phe Ag Cys Glu Leu Cys Ag Asn Pro Ala

Cys Thr Gly Cys (4-F)Phe-NH2;

(SEQ ID NO: 25)
H-Ag Cys Glu Leu Cys Ag Asn Pro Ala Cys Ala Gly

Cys Tyr-NH2;

(SEQ ID NO: 26)
H-Ag Cys Glu Leu Cys Ag Asn Pro Ala Cys Tyr

Gly Cys Tyr-NH2;

(SEQ ID NO: 27)
H-Ag Cys Glu Leu Cys Ag Asn Pro Ala Cys Phe

Gly Cys Tyr-NH2;

(SEQ ID NO: 28)
H-Ag Cys Glu Leu Cys Ag Asn Pro Ala Cys (4-F)Phe

Gly Cys Tyr-NH2;

(SEQ ID NO: 29)
H-Ag Cys Glu Leu Cys Ag Asn Pro Ala Cys Thr

Gly Cys Leu-NH2;

(SEQ ID NO: 30)
H-Ag Cys Glu Leu Cys Ag Asn Pro Ala Cys Thr

Gly Cys Cha-NH2;

(SEQ ID NO: 31)
H-Ag Cys Glu Cha Cys Ag Asn Pro Ala Cys Thr

Gly Cys Tyr-NH2;

(SEQ ID NO: 32)
H-Ag Cys Glu Leu Cys Ag Asn Pro Ala Cys Thr

Gly Cys D-Tyr-NH2;

(SEQ ID NO: 33)
H-Ag Pen Glu Leu Cys Ag Asn Pro Ala Pen Thr

Gly Cys Tyr-NH2;

(SEQ ID NO: 34)
H-Ag Cys Glu Leu Cys Ag Asn Pro Ala Cys Thr

Gly Cys Leu Asn-NH2;

(SEQ ID NO: 35)
H-Ag Cys Glu Leu Cys Ag Asn Pro Ala Cys Thr Gly

Cys Tyr Asn-NH2;

(SEQ ID NO: 36)
H-Asp Ag Cys Glu Leu Cys Ag Asn Pro Ala Cys

Thr Gly Cys Tyr-NH2;

(SEQ ID NO: 37)
H-Ile Asp Ag Cys Glu Leu Cys Ag Asn Pro Ala

Cys Thr Gly Cys Tyr-NH2;

(SEQ ID NO: 38)
H-Ag Cys Glu Leu Cys Ag Asn OH-Pro Ala Cys

Thr Gly Cys Tyr-NH2;

(SEQ ID NO: 39)
H-Ag Cys Glu Leu Cys Ag Asn OH-Pro Ala Cys

Thr Gly Cys-NH2;

(SEQ ID NO: 40)
H-Ag Cys Glu Leu Pen Ag Asn Pro Ala Cys Thr

Gly Pen Tyr-NH2;

(SEQ ID NO: 41)
H-Ag Cys Glu Leu Pen Ag Asn Pro Ala Cys Thr

Gly Pen Tyr-NH2;

(SEQ ID NO: 42)
H-Ag Cys Glu Leu Cys Ag Asn Pro Ala Cys Tyr Gly

Cys Nme-Tyr-NH2;

(SEQ ID NO: 43)
H-Ag Cys Glu Leu Cys Ag Asn Pro Ala Cys Tyr Gly

Cys-COOH;

(SEQ ID NO: 44)
H-Ag Cys Glu Leu Cys Ag Asn Pro Ala Cys Cha

Gly Cys Tyr-NH2;

(SEQ ID NO: 45)
H-Ag Cys Glu Leu Cys Ag Asn Leu Ala Cys Thr

Gly Cys Tyr-NH2;

(SEQ ID NO: 46)
H-Ag Cys Glu Leu Cys Ag Asn Sar Ala Cys Thr

Gly Cys Tyr-NH2;

(SEQ ID NO: 47)
H-Ag Cys Glu Leu Cys Ag Asn Val Ala Cys Thr

Gly Cys Tyr-NH2;

(SEQ ID NO: 48)
H-Ag Cys Glu Leu Cys Ag Asn Pro Ala Cys Tyr

Gly Cys Nme-Tyr-NH2;
```

-continued (SEQ ID NO: 49)
H-Ag Cys Glu Leu Cys Ag Leu Pro Ala Cys Tyr Gly Cys-COOH;

(SEQ ID NO: 50)
H-Ag Cys Asp Leu Cys Ag Asn Pro Ala Cys Tyr Gly Cys-COOH;

(SEQ ID NO: 51)
H-Ag Cys Ser Leu Cys Ag Asn Pro Ala Cys Tyr Gly Cys-COOH;

(SEQ ID NO: 52)
H-Ag Cys Thr Leu Cys Ag Asn Pro Ala Cys Tyr Gly Cys-COOH;

(SEQ ID NO: 53)
H-Hag Cys Glu Leu Cys Hag Asn Pro Ala Cys Thr Gly Cys Tyr-$NH_2$;

(SEQ ID NO: 54)
H-Ag Cys Gln Leu Cys Ag Asn Pro Ala Cys Tyr Gly Cys-COOH;

(SEQ ID NO: 55)
H-Ag Cys Glu Leu Cys Ag Leu Pro Ala Cys Thr Gly Cys Tyr-$NH_2$;

(SEQ ID NO: 56)
Pent-Cys Glu Leu Cys Ag Asn Pro Ala Cys Tyr Gly Cys Tyr-$NH_2$;

(SEQ ID NO: 57)
H-Cys Cys Glu Leu Cys Ag Asn Pro Ala Cys Tyr Gly Ag-COOH;

(SEQ ID NO: 58)
Pent-Cys Glu Leu Cys Ag Asn Pro Ala Cys Tyr Gly Cys-COOH;

(SEQ ID NO: 59)
H-Hag Cys Glu Leu Cys Hag Asn Pro Ala Cys Tyr Gly Cys-COOH;

(SEQ ID NO: 60)
H-Ag Cys Glu Leu Cys Ag Asn Val Ala Cys Tyr Gly Cys Tyr-$NH_2$;

(SEQ ID NO: 61)
H-Ag Cys Glu Leu Cys Ag Asn Val Ala Cys Tyr Gly Cys-COOH;

(SEQ ID NO: 62)
H-Cys Cth Glu Leu Cys Cys Asn Pro Ala Cys Tyr Gly Cys Tyr-$NH_2$;

(SEQ ID NO: 63)
H-Cth Cys Glu Leu Cys Cys Asn Pro Ala Cys Tyr Gly Cys Tyr-$NH_2$;

(SEQ ID NO: 64)
H-Cth Cys Glu Leu Cys Cys Asn Pro Ala Cys Tyr Gly Cys-COOH;

-continued (SEQ ID NO: 65)
H-Cys Cth Glu Leu Cys Cys Asn Val Ala Cys Tyr Gly Cys Tyr-$NH_2$;

(SEQ ID NO: 66)
H-Cys Cth Glu Leu Cys Cys Asn Val Ala Cys Thr Gly Cys Tyr-$NH_2$;

(SEQ ID NO: 67)
Ac-Cys Cth Glu Leu Cys Cys Asn Val Ala Cys Thr Gly Cys Tyr-$NH_2$;

(SEQ ID NO: 68)
Ac-Cys Cth Glu Leu Cys Cys Asn Pro Ala Cys Tyr Gly Cys Tyr-$NH_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;

(SEQ ID NO: 71)
Ac-Cys Cth Glu Leu Cys Cys Asn Pro Ala Cys Tyr Gly Cys-COOH;

(SEQ ID NO: 72)
H-Cys Cys Glu Leu Cys Asn Val Ala Cth Tyr Gly Cys-COOH;

(SEQ ID NO: 73)
H-Cys Cys Glu Leu Cys Cys Asn Val Ala Cth Tyr Gly Cys Tyr-$NH_2$;

(SEQ ID NO: 74)
H-Cys Cys Glu Leu Cys Cys Asn Val Ala Cth Thr Gly Cys Tyr-$NH_2$;

(SEQ ID NO: 75)
H-Cys Cys Glu Leu Cys Cth Asn Val Ala Cys Tyr Gly Cys-COOH;

(SEQ ID NO: 76)
H-Cys Cys Glu Leu Cys Cth Asn Val Ala Cys Tyr Gly Cys Tyr-$NH_2$;

(SEQ ID NO: 77)
H-Cys Cys Glu Leu Cys Cth Asn Val Ala Cys Thr Gly Cys Tyr-$NH_2$;

(SEQ ID NO: 78)
4-Mepip-Cys Cth Glu Leu Cys Cys Asn Val Ala Cys Tyr Gly Cys-COOH;

(SEQ ID NO: 79)
H-Cys Cth Glu Leu Cys Cys Asn Val Ala Cys Thr Gly Cys-COOH;

(SEQ ID NO: 80)
H-Cys Cth Glu Leu Cys Cys Asn Val Ala Cys Thr Gly Cys-$NH_2$;

-continued (SEQ ID NO: 81)
H-Cys Cth Glu Leu Cys Cys Asn Val Ala Cys
Phe Gly Cys-COOH;

(SEQ ID NO: 82)
H-Ag Ag Glu Leu Ag Ag Asn Pro Ala Ag Thr
Gly Ag Tyr-COOH;

(SEQ ID NO: 83)
H-Cys Cth Glu Leu Cys Cys Asn Ala Ala Cys
Thr Gly Cys Tyr-NH$_2$;

(SEQ ID NO: 84)
H-Asp Cys Glu Leu Cys Dpr Asn Val Ala Cys
Thr Gly Cys Tyr-NH$_2$;

(SEQ ID NO: 85)
H-Cys Cth Glu Leu Cys Cys Asn Val Ala Cys
Ser Gly Cys Tyr-NH$_2$;

(SEQ ID NO: 86)
H-Cth Glu Leu Cys Ag Asn Val Ala Cys Thr Gly
Cys Tyr-NH$_2$;

(SEQ ID NO: 87)
H-Ag Cys Glu Leu Cys Ag Asn Val Ala Cys Thr
Gly Cys Tyr-NH$_2$;

(SEQ ID NO: 88)
H-Ag Cys Glu Leu Cys Ag Asn Pro Ala Cys
Thr Gly Cys Tyr-NH$_2$;

(SEQ ID NO: 89)
H-Cth Cys Glu Leu Cys Cys Asn Val Ala Cys
Thr Gly Cys-COOH;

(SEQ ID NO: 90)
H-Cth Cys Glu Leu Cys Cys Asn Val Ala Cys
Thr Gly Cys Tyr-NH$_2$;

(SEQ ID NO: 91)
H-Cth Cys Glu Leu Cys Cys Asn Val Ala Cys
Tyr Gly Cys Tyr-NH$_2$;
or (SEQ ID NO: 92)
H-Cys Cys Glu Leu Cys Cys Asn Val Ala Cth
Tyr Gly Cys-COOH, wherein Ac—indicates an acetylated N-terminus, Pent—indicates an N-terminus capped with pentenoic acid, biotin—indicates an N-terminus capped with biotin, 4-Mepip indicates an N-terminus capped with 4-Mepip (1-methyl-piperidine-4-carboxylic acid), C12—indicates an N-terminus capped with C12 alkyl carboxylic acid, C14—indicates an N-terminus capped with C14 alkyl carboxylic acid, C16—indicates an N-terminus capped with C16 alkyl carboxylic acid, C18—indicates an N-terminus capped with C18 alkyl carboxylic acid, H—indicates an unmodified N-terminus, —NH$_2$ indicates an amidated C-terminus and —COOH indicates an unmodified C-terminus.

In further embodiments, dicarba bond between two Ag residues can be either the cis or trans isomer at the dicarba bond. As used herein, a cis isomer of a dicarba bond has both hydrogen atoms on the same side of the C═C double bond, and a trans isomer of a dicarba bond has hydrogen atoms on opposite sides of the C═C double bond.

In some embodiments, a peptide or pharmaceutically acceptable salt thereof is provided, wherein the peptide comprises peptide comprises no more than 50, 40, 30 or 20 amino acids. In further embodiments, the peptide comprises no more than 19, 18, 17, 16, 15 or 14 amino acids.

In another aspect, the present invention provides a peptide or a pharmaceutically acceptable salt thereof, wherein the peptide consists of the amino acid sequence Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Ala$_{15}$ Xaa$_{16}$ Xaa$_{17}$ Gly$_{18}$ Xaa$_{19}$ Xaa$_{20}$ Xaa$_{21}$ (SEQ ID NO: 1), or a pharmaceutically acceptable salt thereof; wherein Xaa$_1$ is BE or is absent;
Xaa$_2$ is BK, Asn or is absent;
Xaa$_3$ is Asn, Ser or is absent;
Xaa$_4$ is Ser or is absent;
Xaa$_5$ is Ser, Asn, Ile, BE or is absent;
Xaa$_6$ is Tyr, Asp, 4-fluorophenylalanine ((4-F)Phe), BK or is absent;
Xaa$_7$ is Cys, cystathionine (Cth), allylglycine (Ag), Hag, or Asp;
Xaa$_8$ is Cys, cystathionine (Cth), penicillamine (Pen), or allylglycine (Ag);
Xaa$_9$ is Glu, Asp, Ser, Thr, or Gln;
Xaa$_{10}$ is Leu, cyclohexylalanine (Cha), Phe, or 4-fluorophenylalanine ((4-F)Phe);
Xaa$_{11}$ is Cys, Ag, or penicillamine (Pen);
Xaa$_{12}$ is Cys, allylglycine (Ag), Hag, Cth, Dpr, or Val;
Xaa$_{13}$ is Asn or Leu;
Xaa$_{14}$ is Pro, Val, sarcosine (Sar), Leu, or Hydroxyproline (OH-Pro);
Xaa$_{16}$ is Cys, Ag, Pen or Cth;
Xaa$_{17}$ is Tyr, Thr, cyclohexylalanine (Cha), 4-fluorophenylalanine ((4-F)Phe), Phe, Ser, or Ala;
Xaa$_{19}$ is Cys, Ag or Pen;
Xaa$_{20}$ is Tyr, Leu, 4-fluorophenylalanine ((4-F)Phe), cyclohexylalanine (Cha), D-Tyr, N-Methyl Tyr (Nme-Tyr) or is absent;
Xaa$_{21}$ is absent or Asn;
wherein at least one Xaa is BE, BK, (4-F)Phe, Cth, Ag, Hag, Pen, Cha, Sar, Dpr, or OH-Pro
and wherein the peptide contains a covalent bond between Xaa$_7$ and Xaa$_{12}$, Xaa$_8$ and Xaa$_{16}$ and Xaa$_{11}$ and Xaa$_{19}$.

In some embodiments, the N-terminus of the peptide is acetylated to provide added stability to the peptide. In other embodiments, the N-terminus is capped with pentenoic acid, biotin, 4-Mepip (1-methyl-piperidine-4-carboxylic acid), C12 alkyl carboxylic acid, C14 alkyl carboxylic acid, C16 alkyl carboxylic acid, or C18 alkyl carboxylic acid. In some embodiments, the C═C double bond of the pentenoic acid may be cyclized with another C═C double bond to form a dicarba bond.

In some embodiments, the C-terminus of the peptide is amidated to provide added stability to the peptide.

In some embodiments, $Xaa_7$ and $Xaa_{12}$ are both Ag and a dicarba bond is present between $Ag_7$ and $Ag_{12}$; $Xaa_7$ and $Xaa_{12}$ are both Cys and a disulfide bond is present between $Cys_7$ and $Cys_{12}$; $Xaa_8$ and $Xaa_{16}$ are both Cys and a disulfide bond is present between $Cys_8$ and $Cys_{16}$; $Xaa_{11}$ and $Xaa_{19}$ are both Cys, and a disulfide bond is present between $Cys_{11}$ and $Cys_{19}$; or any combination thereof.

In some embodiments, $Xaa_7$ is allylglycine or Cys.

In some embodiments, $Xaa_8$ is Cys or cystathionine.

In some embodiments, $Xaa_9$ is Glu.

In some embodiments, $Xaa_{10}$ is Leu.

In some embodiments, Xaa$_{12}$ is Cys or allylglycine.

In some embodiments, Xaa$_{14}$ is Val or Pro.

In some embodiments, Xaa$_{17}$ is Tyr or Thr.

In some embodiments, Xaa$_{20}$ is Tyr or is absent.

In some embodiments, Xaa$_{21}$ is absent.

In some embodiments, Xaa$_1$ is absent; Xaa$_2$ is absent; Xaa$_3$ is absent; Xaa$_4$ is absent; Xaa$_5$ is absent; Xaa$_6$ is absent; Xaa$_7$ is Ag, Cys, or Cth; Xaa$_8$ is Cys or Cth; Xaa$_9$ is Glu; Xaa$_{10}$ is Leu; Xaa$_{12}$ is Ag or Cys; Xaa$_{14}$ is Val or Pro; Xaa$_{17}$ is Tyr or Thr; and Xaa$_{20}$ is Tyr or is absent.

In some embodiments, a peptide or pharmaceutically acceptable salt thereof is provided, wherein the peptide consists of the amino acid sequence:

```
                                              (SEQ ID NO: 2)
H-Ag Cys Glu Leu Cys Ag Asn Pro Ala Cys Thr

Gly Cys Tyr-NH2;
                                              (SEQ ID NO: 3)
C12-BE BK Asn Ser Ser Tyr Cys Cys Glu Leu Cys

Cys Asn Pro Ala Cys Thr Gly Cys Tyr-NH2;
                                              (SEQ ID NO: 4)
C16-BE BK Asn Ser Ser Tyr Cys Cys Glu Leu Cys

Cys Asn Pro Ala Cys Thr Gly Cys Tyr-NH2;
                                              (SEQ ID NO: 5)
C12-BE BK Asn Ser Ser Tyr Cys Cys Glu Leu Cys

Cys Asn Pro Ala Cys Thr Gly Cys Tyr-COOH;
                                              (SEQ ID NO: 6)
C14-BE BK Asn Ser Ser Tyr Cys Cys Glu Leu Cys

Cys Asn Pro Ala Cys Thr Gly Cys Tyr-COOH;
                                              (SEQ ID NO: 7)
C16-BE BK Asn Ser Ser Tyr Cys Cys Glu Leu Cys

Cys Asn Pro Ala Cys Thr Gly Cys Tyr-COOH;
                                              (SEQ ID NO: 8)
H-Cys Ag Glu Leu Cys Cys Asn Pro Ala Ag Thr Gly

Cys Tyr-NH2;
                                              (SEQ ID NO: 9)
H-Asn Asp Asp Ag Glu Leu Cys Val Asn Val Ala Ag

Thr Gly Cys Leu-NH2;
                                              (SEQ ID NO: 10)
H-Asn Asp Asp Cys Glu Leu Ag Val Asn Val Ala

Cys Thr Gly Ag Leu-NH2;
                                              (SEQ ID NO: 11)
C18-BE BK Asn Ser Ser Tyr Cys Cys Glu Leu Cys

Cys Asn Pro Ala Cys Thr Gly Cys Tyr-COOH;
                                              (SEQ ID NO: 12)
H-Ag Cys Glu Leu Cys Ag Asn Pro Ala Cys Thr Gly

Cys-NH2;
                                              (SEQ ID NO: 13)
H-Ag Cys Glu Leu Cys Ag Asn Pro Ala Cys Ala Gly

Cys-NH2;
                                              (SEQ ID NO: 14)
H-Ag Cys Glu Phe Cys Ag Asn Pro Ala Cys Thr Gly

Cys Tyr-NH2;
                                              (SEQ ID NO: 15)
H-Ag Cys Glu (4-F)Phe Cys Ag Asn Pro Ala Cys Thr

Gly Cys-NH2;
                                              (SEQ ID NO: 16)
H-Ag Cys Glu (4-F)Phe Cys Ag Asn Pro Ala Cys Thr

Gly Cys Tyr-NH2;
                                              (SEQ ID NO: 17)
H-Ag Cys Glu (4-F)Phe Cys Ag Asn Pro Ala Cys Thr

Gly Cys (4-F)Phe-NH2;
                                              (SEQ ID NO: 18)
H-Cys Cys Glu Leu Ag Cys Asn Pro Ala Cys Thr Gly

Ag Tyr-NH2;
                                              (SEQ ID NO: 19)
H-Ag Cys Glu Phe Cys Ag Asn Pro Ala Cys Thr Gly

Cys-NH2;
                                              (SEQ ID NO: 20)
H-Ag Cys Glu Phe Cys Ag Asn Pro Ala Cys Thr Gly

Cys (4-F)Phe-NH2;
                                              (SEQ ID NO: 21)
H-Cys Cys Glu (4-F)Phe Cys Cys Asn Pro Ala Cys

Thr Gly Cys Tyr-NH2;
                                              (SEQ ID NO: 22)
H-Cys Cys Glu (4-F)Phe Cys Cys Asn Pro Ala Cys

Thr Gly Cys (4-F)Phe-NH2;
                                              (SEQ ID NO: 23)
H-Ag Cys Glu Leu Cys Ag Asn Pro Ala Cys Thr Gly

Cys (4-F)Phe-NH2;
                                              (SEQ ID NO: 24)
H-(4-F)Phe Ag Cys Glu Leu Cys Ag Asn Pro Ala

Cys Thr Gly Cys (4-F)Phe-NH2;
                                              (SEQ ID NO: 25)
H-Ag Cys Glu Leu Cys Ag Asn Pro Ala Cys Ala

Gly Cys Tyr-NH2;
                                              (SEQ ID NO: 26)
H-Ag Cys Glu Leu Cys Ag Asn Pro Ala Cys Tyr

Gly Cys Tyr-NH2;
                                              (SEQ ID NO: 27)
H-Ag Cys Glu Leu Cys Ag Asn Pro Ala Cys Phe

Gly Cys Tyr-NH2;
                                              (SEQ ID NO: 28)
H-Ag Cys Glu Leu Cys Ag Asn Pro Ala Cys (4-F)Phe

Gly Cys Tyr-NH2;
                                              (SEQ ID NO: 29)
H-Ag Cys Glu Leu Cys Ag Asn Pro Ala Cys Thr Gly

Cys Leu-NH2;
```

(SEQ ID NO: 30)
H-Ag Cys Glu Leu Cys Ag Asn Pro Ala Cys Thr Gly Cys Cha-NH$_2$;

(SEQ ID NO: 31)
H-Ag Cys Glu Cha Cys Ag Asn Pro Ala Cys Thr Gly Cys Tyr-NH$_2$;

(SEQ ID NO: 32)
H-Ag Cys Glu Leu Cys Ag Asn Pro Ala Cys Thr Gly Cys D-Tyr-NH$_2$;

(SEQ ID NO: 33)
H-Ag Pen Glu Leu Cys Ag Asn Pro Ala Pen Thr Gly Cys Tyr-NH$_2$;

(SEQ ID NO: 34)
H-Ag Cys Glu Leu Cys Ag Asn Pro Ala Cys Thr Gly Cys Leu Asn-NH$_2$;

(SEQ ID NO: 35)
H-Ag Cys Glu Leu Cys Ag Asn Pro Ala Cys Thr Gly Cys Tyr Asn-NH$_2$;

(SEQ ID NO: 36)
H-Asp Ag Cys Glu Leu Cys Ag Asn Pro Ala Cys Thr Gly Cys Tyr-NH$_2$;

(SEQ ID NO: 37)
H-Ile Asp Ag Cys Glu Leu Cys Ag Asn Pro Ala Cys Thr Gly Cys Tyr-NH$_2$;

(SEQ ID NO: 38)
H-Ag Cys Glu Leu Cys Ag Asn OH-Pro Ala Cys Thr Gly Cys Tyr-NH$_2$;

(SEQ ID NO: 39)
H-Ag Cys Glu Leu Cys Ag Asn OH-Pro Ala Cys Thr Gly Cys-NH$_2$;

(SEQ ID NO: 40)
H-Ag Cys Glu Leu Pen Ag Asn Pro Ala Cys Thr Gly Pen Tyr-NH$_2$;

(SEQ ID NO: 41)
H-Ag Cys Glu Leu Pen Ag Asn Pro Ala Cys Thr Gly Pen Tyr-NH$_2$;

(SEQ ID NO: 42)
H-Ag Cys Glu Leu Cys Ag Asn Pro Ala Cys Tyr Gly Cys Nme-Tyr-NH$_2$;

(SEQ ID NO: 43)
H-Ag Cys Glu Leu Cys Ag Asn Pro Ala Cys Tyr Gly Cys-COOH;

(SEQ ID NO: 44)
H-Ag Cys Glu Leu Cys Ag Asn Pro Ala Cys Cha Gly Cys Tyr-NH$_2$;

(SEQ ID NO: 45)
H-Ag Cys Glu Leu Cys Ag Asn Leu Ala Cys Thr Gly Cys Tyr-NH$_2$;

(SEQ ID NO: 46)
H-Ag Cys Glu Leu Cys Ag Asn Sar Ala Cys Thr Gly Cys Tyr-NH$_2$;

(SEQ ID NO: 47)
H-Ag Cys Glu Leu Cys Ag Asn Val Ala Cys Thr Gly Cys Tyr-NH$_2$;

(SEQ ID NO: 48)
H-Ag Cys Glu Leu Cys Ag Asn Pro Ala Cys Tyr Gly Cys Nme-Tyr-NH$_2$;

(SEQ ID NO: 49)
H-Ag Cys Glu Leu Cys Ag Leu Pro Ala Cys Tyr Gly Cys-COOH;

(SEQ ID NO: 50)
H-Ag Cys Asp Leu Cys Ag Asn Pro Ala Cys Tyr Gly Cys-COOH;

(SEQ ID NO: 51)
H-Ag Cys Ser Leu Cys Ag Asn Pro Ala Cys Tyr Gly Cys-COOH;

(SEQ ID NO: 52)
H-Ag Cys Thr Leu Cys Ag Asn Pro Ala Cys Tyr Gly Cys-COOH;

(SEQ ID NO: 53)
H-Hag Cys Glu Leu Cys Hag Asn Pro Ala Cys Thr Gly Cys Tyr-$NH_2$;

(SEQ ID NO: 54)
H-Ag Cys Gln Leu Cys Ag Asn Pro Ala Cys Tyr Gly Cys-COOH;

(SEQ ID NO: 55)
H-Ag Cys Glu Leu Cys Ag Leu Pro Ala Cys Thr Gly Cys Tyr-$NH_2$;

(SEQ ID NO: 56)
Pent-Cys Glu Leu Cys Ag Asn Pro Ala Cys Tyr Gly Cys Tyr-$NH_2$;

(SEQ ID NO: 57)
H-Cys Cys Glu Leu Cys Ag Asn Pro Ala Cys Tyr Gly Ag-COOH;

(SEQ ID NO: 58)
Pent-Cys Glu Leu Cys Ag Asn Pro Ala Cys Tyr Gly Cys-COOH;

(SEQ ID NO: 59)
H-Hag Cys Glu Leu Cys Hag Asn Pro Ala Cys Tyr Gly Cys-COOH;

(SEQ ID NO: 60)
H-Ag Cys Glu Leu Cys Ag Asn Val Ala Cys Tyr Gly Cys Tyr-$NH_2$;

(SEQ ID NO: 61)
H-Ag Cys Glu Leu Cys Ag Asn Val Ala Cys Tyr Gly Cys-COOH;

(SEQ ID NO: 62)
H-Cys Cth Glu Leu Cys Cys Asn Pro Ala Cys Tyr Gly Cys Tyr-NH$_2$;

(SEQ ID NO: 63)
H-Cth Cys Glu Leu Cys Cys Asn Pro Ala Cys Tyr Gly Cys Tyr-NH$_2$;

(SEQ ID NO: 64)
H-Cth Cys Glu Leu Cys Cys Asn Pro Ala Cys Tyr Gly Cys-COOH;

(SEQ ID NO: 65)
H-Cys Cth Glu Leu Cys Cys Asn Val Ala Cys Tyr Gly Cys Tyr-NH$_2$;

(SEQ ID NO: 66)
H-Cys Cth Glu Leu Cys Cys Asn Val Ala Cys Thr Gly Cys Tyr-NH$_2$;

(SEQ ID NO: 67)
Ac-Cys Cth Glu Leu Cys Cys Asn Val Ala Cys Thr Gly Cys Tyr-NH$_2$;

(SEQ ID NO: 68)
Ac-Cys Cth Glu Leu Cys Cys Asn Pro Ala Cys Tyr Gly Cys Tyr-NH$_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;

(SEQ ID NO: 71)
Ac-Cys Cth Glu Leu Cys Cys Asn Pro Ala Cys Tyr Gly Cys-COOH;

(SEQ ID NO: 72)
H-Cys Cys Glu Leu Cys Asn Val Ala Cth Tyr Gly Cys-COOH;

(SEQ ID NO: 73)
H-Cys Cys Glu Leu Cys Cys Asn Val Ala Cth Tyr Gly Cys Tyr-NH$_2$;

(SEQ ID NO: 74)
H-Cys Cys Glu Leu Cys Cys Asn Val Ala Cth Thr Gly Cys Tyr-NH$_2$;

(SEQ ID NO: 75)
H-Cys Cys Glu Leu Cys Cth Asn Val Ala Cys Tyr Gly Cys-COOH;

(SEQ ID NO: 76)
H-Cys Cys Glu Leu Cys Cth Asn Val Ala Cys Tyr Gly Cys Tyr-NH$_2$;

(SEQ ID NO: 77)
H-Cys Cys Glu Leu Cys Cth Asn Val Ala Cys Thr Gly Cys Tyr-NH$_2$;

(SEQ ID NO: 78)
4-Mepip-Cys Cth Glu Leu Cys Cys Asn Val Ala Cys Tyr Gly Cys-COOH;

(SEQ ID NO: 79)
H-Cys Cth Glu Leu Cys Cys Asn Val Ala Cys Thr Gly Cys-COOH;

(SEQ ID NO: 80)
H-Cys Cth Glu Leu Cys Cys Asn Val Ala Cys Thr Gly Cys-NH$_2$;

(SEQ ID NO: 81)
H-Cys Cth Glu Leu Cys Cys Asn Val Ala Cys Phe Gly Cys-COOH;

(SEQ ID NO: 82)
H-Ag Ag Glu Leu Ag Ag Asn Pro Ala Ag Thr Gly Ag Tyr-COOH;

(SEQ ID NO: 83)
H-Cys Cth Glu Leu Cys Cys Asn Ala Ala Cys Thr Gly Cys Tyr-NH$_2$;

(SEQ ID NO: 84)
H-Asp Cys Glu Leu Cys Dpr Asn Val Ala Cys Thr Gly Cys Tyr-NH$_2$;

(SEQ ID NO: 85)
H-Cys Cth Glu Leu Cys Cys Asn Val Ala Cys Ser Gly Cys Tyr-NH$_2$;

(SEQ ID NO: 86)
H-Cth Glu Leu Cys Ag Asn Val Ala Cys Thr Gly Cys Tyr-NH$_2$;

(SEQ ID NO: 87)
H-Ag Cys Glu Leu Cys Ag Asn Val Ala Cys Thr Gly Cys Tyr-NH$_2$;

(SEQ ID NO: 88)
H-Ag Cys Glu Leu Cys Ag Asn Pro Ala Cys Thr Gly Cys Tyr-NH$_2$;

(SEQ ID NO: 89)
H-Cth Cys Glu Leu Cys Cys Asn Val Ala Cys Thr Gly Cys-COOH;

(SEQ ID NO: 90)
H-Cth Cys Glu Leu Cys Cys Asn Val Ala Cys Thr Gly Cys Tyr-NH$_2$;

(SEQ ID NO: 91)
H-Cth Cys Glu Leu Cys Cys Asn Val Ala Cys Tyr Gly Cys Tyr-NH$_2$;
or (SEQ ID NO: 92)
H-Cys Cys Glu Leu Cys Cys Asn Val Ala Cth Tyr Gly Cys-COOH.

In another embodiment, the present invention provides a peptide or a pharmaceutically acceptable salt thereof useful for the methods described herein, wherein the peptide comprises or consists of the amino acid sequence:

Xaa$_1$ Xaa$_2$ Xaa$_3$ Xaa$_4$ Xaa$_5$ Xaa$_6$ Xaa$_7$Xaa$_8$Xaa$_9$Xaa$_{10}$ Cys$_{11}$ Xaa$_{12}$ Asn$_{13}$ Xaa$_{14}$ Ala$_{15}$ Cys$_{16}$ Xaa$_{17}$ Gly$_{18}$ Cys$_{19}$ Xaa$_{20}$ Xaa$_{21}$ (SEQ ID NO: 93), or a pharmaceutically acceptable salt thereof; wherein Xaa$_1$ is BE or is absent;
Xaa$_2$ is BK or is absent;
Xaa$_3$ is Asn or is absent;
Xaa$_4$ is Ser or is absent;
Xaa$_5$ is Ser, Asn, Ile, or is absent;
Xaa$_6$ is Tyr, Asp, 4-fluorophenylalanine ((4-F)Phe), or is absent;
Xaa$_7$ is Cys, cystathionine (Cth), allylglycine (Ag), Hag, or Asp;
Xaa$_8$ is Cys, cystathionine (Cth), penicillamine (Pen), or allylglycine (Ag);
Xaa$_9$ is Glu, Asp, Ser, Thr, or Gln;
Xaa$_{10}$ is Leu, cyclohexylalanine (Cha), Phe, or 4-fluorophenylalanine ((4-F)Phe);
Xaa$_{12}$ is Cys, allylglycine (Ag), Hag, or Val;
Xaa$_{14}$ is Pro, Val, sarcosine (Sar), Leu, or Hydroxyproline (OH-Pro);
Xaa$_{17}$ is Tyr, Thr, cyclohexylalanine (Cha), 4-fluorophenylalanine ((4-F)Phe), Phe, or Ala;
Xaa$_{20}$ is Tyr, Leu, 4-fluorophenylalanine ((4-F)Phe), cyclohexylalanine (Cha), D-Tyr, N-Methyl Tyr (Nme-Tyr) or is absent;
Xaa$_{21}$ is absent or Asn;
wherein at least one Xaa is BE, BK, (4-F)Phe, Cth, Ag, Hag, Pen, Cha, Sar, or OH-Pro; and
wherein the peptide contains a covalent bond between Xaa$_7$ and Xaa$_{12}$, Xaa$_8$ and Cys$_{16}$ and Cys$_{11}$ and Cys$_{19}$.

In further embodiments, the peptide or a pharmaceutically acceptable salt thereof, wherein the peptide comprises or consists of the amino acid sequence:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Cys$_{11}$, Xaa$_{12}$ Asn$_{13}$ Xaa$_{14}$ Ala$_{15}$ Cys$_{16}$ Xaa$_{17}$ Gly$_8$ Cys$_{19}$ Xaa$_{20}$ Xaa$_{21}$ (SEQ ID NO:93), or a pharmaceutically acceptable salt thereof; wherein Xaa$_1$ is BE or is absent;
Xaa$_2$ is BK or is absent;
Xaa$_3$ is Asn or is absent;
Xaa$_4$ is Ser or is absent;
Xaa$_5$ is Ser, Asn, Ile, or is absent;
Xaa$_6$ is Tyr, Asp, 4-fluorophenylalanine ((4-F)Phe), or is absent;
Xaa$_7$ is Cys, cystathionine (Cth), allylglycine (Ag), Hag, or Asp;
Xaa$_8$ is Cys, cystathionine (Cth), penicillamine (Pen), or allylglycine (Ag);
Xaa$_9$ is Glu, Asp, Ser, Thr, or Gln;
Xaa$_{10}$ is Leu, cyclohexylalanine (Cha), Phe, or 4-fluorophenylalanine ((4-F)Phe);
Xaa$_{12}$ is Cys, allylglycine (Ag), Hag, or Val;
Xaa$_{14}$ is Pro, Val, sarcosine (Sar), Leu, or Hydroxyproline (OH-Pro);
Xaa$_{17}$ is Tyr, Thr, cyclohexylalanine (Cha), 4-fluorophenylalanine ((4-F)Phe), Phe, or Ala;
Xaa$_{20}$ is Tyr, Leu, 4-fluorophenylalanine ((4-F)Phe), cyclohexylalanine (Cha), D-Tyr, N-Methyl Tyr (Nme-Tyr) or is absent;
Xaa$_{21}$ is absent or Asn;
wherein at least one Xaa is BE, BK, (4-F)Phe, Cth, Ag, Hag, Pen, Cha, Sar, or OH-Pro; and
wherein Xaa$_7$ and Xaa$_{12}$ are both Ag and a dicarba bond is present between Ag$_7$ and Ag$_{12}$;
Xaa$_7$ and Xaa$_{12}$ are both Cys and a disulfide bond is present between Cys$_7$ and Cys$_{12}$;

Xaa$_8$ is Cys and a disulfide bond is present between Cys$_8$ and Cys$_{16}$;
Xaa$_7$ is Cth and a bond is present between Cth$_7$ and Cys$_{12}$;
Xaa$_8$ is Cth and a bond is present between Cth$_8$ and Cys$_{16}$;
a disulfide bond is present between Cys$_{11}$ and Cys$_{19}$; or any combination thereof.

In some embodiments, the peptide is isolated. In other embodiments, the peptide is purified.

In some embodiments, a pharmaceutically acceptable salt of the peptide is provided. In some instances, the pharmaceutically acceptable salt is a chloride, acetate, phosphate or sulfate salt.

In some embodiments, the N-terminus of the peptides described herein is acetylated or capped. This modification may provide enhanced stability to the peptide. In other embodiments, the N-terminal peptide is a cysteine residue that has been modified into an imidazolidinone derivative.

The peptides disclosed herein may also be used for detection opportunities or colon cancer treatment. In the case of using the peptides in detection situations, a linker is conjugated to the N-terminus. The linker may then be conjugated to a dye, or may be conjugated to a dye prior to bonding with the peptide. One skilled in the art would recognize a peptide conjugated dye would be useful in detection of peptide binding interactions.

Another embodiment includes conjugating the peptides disclosed herein to a toxin by way of a linker. A toxin conjugated and coated with a peptide or pharmaceutically acceptable salt as described herein would be useful as a colon cancer treatment. Such a formulation would result in systemic circulation for a long-acting treatment. One skilled in the art would recognize the use of a long-acting peptide or pharmaceutically acceptable salt thereof as described herein in the treatment of colon cancer.

Production of Peptides

In one embodiment, peptides or precursor peptides of the invention can be produced recombinantly in any known protein expression system, including, without limitation, bacteria (e.g., *E. coli* or *Bacillus subtilis*), insect cell systems (e.g., Drosophila Sf9 cell systems), yeast cell systems (e.g., *S. cerevisiae, S. saccharomyces*) or filamentous fungal expression systems, or animal cell expression systems (e.g., mammalian cell expression systems). If the peptide or variant peptide is to be produced recombinantly, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally-occurring bacterial heat-stable enterotoxin (ST) peptide. The secreted, mature peptide can be purified from the culture medium.

The sequence encoding a peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E coli, B. subtilis, Pseudomonas* and *Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

The protein coding sequence that includes a peptide described herein can also be fused to a nucleic acid encoding a peptide affinity tag, e.g., glutathione S-transferase (GST), maltose E binding protein, protein A, FLAG tag, hexahistidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the peptides and variants described herein in protein expression systems other than bacteria, and well known to those skilled in the art, can also be used to produce peptides in a biological system.

In some embodiments, peptides may be chemically produced. Peptides can be synthesized by a number of different methods including solution and solid phase synthesis using traditional BOC or FMOC protection. For example, the peptide can be synthesized on 2-Chlorotritylchloride or Wang resin using consecutive amino acid couplings. Various protecting groups can be used including, without limitation, the following protecting groups: Fluorenylmethyloxycarbonyl or tert-butyloxycarbonyl (alpha-amino groups, N-terminus); trityl or tent-butyl (thiol groups of Cys); tert-butyl (γ-carboxyl of glutamic acid and the hydroxyl group of threonine, if present); trityl (β-amid function of the asparagine side chain and the phenolic group of tyrosine, if present); trityl or tert-butyldimethylsilyl (hydroxygroup of serine, if present) and tert-Butyloxycarbonyl (N-terminus prior to subsequent side chain modifications). Coupling, deprotecting and cleavage can be effected through various methods. In some embodiments, coupling is effected with DIC and HOBt in the presence of a tertiary amine, and the peptide can be deprotected and cleaved from the solid support in using cocktail K (trifluoroacetic acid 81%, phenol 5%, thioanisole 5%, 1,2-ethanedithiol 2.5%, water 3%, dimethylsulphide 2%, ammonium iodide 1.5% w/w). The peptide can be isolated through various methods. In one embodiment, after removal of trifluoroacetic acid and other volatiles the peptide can be precipitated using an organic solvent. Disulfide bonds between Cys residues can be formed using various methods. In one embodiment, disulfide bonds between Cys residue can be formed using dimethyl sulfoxide (Tam et al. (1991) J. Am. Chem. Soc. 113:6657-62) or using an air oxidation strategy. The resulting peptide can be purified through various methods including, without limitation, by reverse-phase chromatography and lyophilized.

Peptides can be made, isolated or used either in form of the free base or as pharmaceutically acceptable salts thereof. Examples of salts include, without limitation, acetate, chloride, sulfate and phosphate salts of the peptide.

Compositions of Peptides and GC-C Receptor Agonists

In another aspect, compositions are provided wherein the peptides, alone or in combination, can be combined with any pharmaceutically acceptable carrier or medium. In some embodiments, the peptide or pharmaceutically acceptable salt thereof can be formulated into a pharmaceutically acceptable composition. In other embodiments, the peptide or pharmaceutically acceptable salt thereof can be formulated into a non-pharmaceutically acceptable composition. The peptides can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose (e.g., celphere, Celphere beads®), diluents, lubricants, binders, disintegrating agents, and the like), etc. If desired, tablet dosages of the disclosed compositions may be coated by standard aqueous or nonaqueous techniques.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

As used herein, the term "binder" refers to any pharmaceutically acceptable binder that may be used in the practice of the invention. Examples of pharmaceutically acceptable binders include, without limitation, a starch (e.g., corn starch, potato starch and pre-gelatinized starch (e.g., STARCH 1500® and STARCH 1500 LM®, sold by Colorcon, Ltd.) and other starches), maltodextrin, gelatin, natural and synthetic gums such as acacia, powdered tragacanth, guar gum, cellulose and its derivatives (e.g., methylcellulose, hydroxyethyl cellulose, hydroxyethyl methylcellulose, hydroxypropyl cellulose and hydroxypropyl methylcellulose (hypromellose), ethyl cellulose, cellulose acetate, carboxymethyl cellulose calcium, sodium carboxymethyl cellulose, carboxymethylcellulose, powdered cellulose, microfine cellulose, microcrystalline cellulose (e.g. AVICEL™, such as, AVICEL-PH-101™, -103™ and -105™, sold by FMC Corporation, Marcus Hook, Pa., USA)), polyvinyl alcohol, polyvinyl pyrrolidone (e.g., polyvinyl pyrrolidone K30), and mixtures thereof.

Examples of binders that may be particularly used in pharmaceutical compositions include polyvinyl alcohol, polyvinylpyrrolidone (povidone), a starch, maltodextrin or a cellulose ether (such as, for example, methylcellulose, ethylcellulose, carboxymethylcellulose, hydroxyethyl cellulose, hydroxyethyl methylcellulose, hydroxypropyl cellulose and hydroxypropyl methylcellulose).

As used herein, the term "filler" refers to any pharmaceutically acceptable filler that may be used in the practice of the invention. Examples of pharmaceutically acceptable fillers include, without limitation, talc, calcium carbonate (e.g., granules or powder), dibasic calcium phosphate, tribasic calcium phosphate, calcium sulfate (e.g., granules or powder), microcrystalline cellulose (e.g., Avicel PH101 or Celphere CP-305), microfine cellulose, powdered cellulose, dextrates, kaolin, mannitol, silicic acid, sorbitol, starch (e.g., Starch 1500), pre-gelatinized starch, lactose, glucose, fructose, galactose, trehalose, sucrose, maltose, isomalt, raffinose, maltitol, melezitose, stachyose, lactitol, palatinite, xylitol, myoinositol, and mixtures thereof.

Examples of pharmaceutically acceptable fillers that may be particularly used for coating the peptides include, without limitation, talc, microcrystalline cellulose (e.g., Avicel PH101 or Celphere CP-305), powdered cellulose, dextrates, kaolin, mannitol, silicic acid, sorbitol, starch, pre-gelatinized starch, lactose, glucose, fructose, galactose, trehalose, sucrose, maltose, isomalt, dibasic calcium phosphate, raffinose, maltitol, melezitose, stachyose, lactitol, palatinite, xylitol, mannitol, myoinositol, and mixtures thereof.

As used herein, the term "additives" refers to any pharmaceutically acceptable additive. Pharmaceutically acceptable additives include, without limitation, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes. As used herein, an "excipient" is any pharmaceutically acceptable additive, filler, binder or agent.

Compositions of the present invention may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

The compositions can include, for example, various additional solvents, dispersants, coatings, absorption promoting additives, controlled release additives, and one or more inert additives (which include, for example, starches, polyols, granulating additives, microcrystalline cellulose, diluents, lubricants, binders, disintegrating additives, and the like), etc. If desired, tablet dosages of the disclosed compositions may be coated by standard aqueous or non-aqueous techniques. Compositions can also include, for example, anti-caking additives, preservatives, sweetening additives, colorants, flavors, desiccants, plasticizers, dyes, and the like.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable glidants include, for example, leucine, colloidal silicon dioxide, magnesium trisilicate, powdered cellulose, starch, talc, and tribasic calcium phosphate.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the peptides compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable antioxidants include, for example, BHA (butylated hydroxyanisole), BHT (butylated hydroxytoluene), vitamin E, propyl gallate, ascorbic acid and salts or esters thereof, tocopherol and esters thereof, alpha-lipoic acid and beta-carotene.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. Suitable protective coatings include Aquacoat (e.g., Aquacoat Ethylcellulose Aqueous Dispersion, 15% w/w, FMC Biopolymer, ECD-30), Eudragit (e.g., Eudragit E PO PE-EL, Roehm Pharma Polymers) and Opadry (e.g Opadry AMB dispersion, 20% w/w, Colorcon).

In certain embodiments, suitable additives for the peptides composition include one or more of sucrose, talc, magnesium stearate, crospovidone or BHA.

The compositions of the present invention can also include other excipients, agents, and categories thereof including but not limited to L-histidine, Pluronic®, Poloxamers (such as Lutrol® and Poloxamer 188), ascorbic acid, glutathione, permeability enhancers (e.g., lipids, sodium cholate, acylcarnitine, salicylates, mixed bile salts, fatty acid micelles, chelators, fatty acid, surfactants, medium chain glycerides), protease inhibitors (e.g., soybean trypsin inhibitor, organic acids), pH lowering agents and absorption enhancers effective to promote bioavailability (including but not limited to those described in U.S. Pat. Nos. 6,086,918 and 5,912,014), materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No.3, FD&C Red No. 40, FD&C Yellow No. 6 Aluminum Lake, FD&C Yellow No. 6, FD&C Yellow No.10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

In some embodiments, there is provided a pharmaceutical composition comprising a peptide described herein and one or more stabilizing agents selected from $Mg^{2+}$, $Ca^{2+}$, $Zn^{2+}$, $Mn^{2+}$, $K^+$, $Na^+$ or $Al^{3+}$, a combination thereof, and/or a sterically hindered primary amine. In further embodiments, the agent is $Mg^{2+}$, $Ca^{2+}$ or $Zn^{2+}$ or a combination thereof In some embodiments, the cation is provided, without limitation, as magnesium acetate, magnesium chloride, magnesium phosphate, magnesium sulfate, calcium acetate, calcium chloride, calcium phosphate, calcium sulfate, zinc acetate, zinc chloride, zinc phosphate, zinc sulfate, manganese acetate, manganese chloride, manganese phosphate, manganese sulfate, potassium acetate, potassium chloride, potassium phosphate, potassium sulfate, sodium acetate, sodium chloride, sodium phosphate, sodium sulfate, aluminum acetate, aluminum chloride, aluminum phosphate or aluminum sulfate. In further embodiments, the cation is provided as magnesium chloride, calcium chloride, calcium phosphate, calcium sulfate, zinc acetate, manganese chloride, potassium chloride, sodium chloride or aluminum chloride. In other embodiments, the cation is provided as calcium chloride, magnesium chloride or zinc acetate.

In another embodiment, the stabilizing agent is a sterically hindered primary amine. In a further embodiment, the sterically hindered primary amine is an amino acid. In yet a further embodiment, the amino acid is a naturally-occurring amino acid. In a still further embodiment, the naturally-occurring amino acid is selected from the group consisting of: histidine, phenylalanine, alanine, glutamic acid, aspartic acid, glutamine, leucine, methionine, asparagine, tyrosine, threonine, isoleucine, tryptophan, glycine and valine; yet further, the naturally-occurring amino acid is leucine, isoleucine, alanine or methionine. In another embodiment, the sterically hindered primary amine is a non-naturally occurring amino acid (e.g., 1-aminocyclohexane carboxylic acid). In a further embodiment, the sterically hindered primary amine is cyclohexylamine, 2-methylbutylamine or a polymeric amine such as chitosan. In another embodiment, one or more sterically hindered primary amines may be used in a composition.

In some cases, the sterically hindered primary amine has the formula:

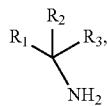

wherein $R_1$, $R_2$ and $R_3$ are independently selected from: H, C(O)OH, $C_1$-$C_6$ alkyl, $C_1$-$C_6$ alkylether, $C_1$-$C_6$ alkylthioether, $C_1$-$C_6$ alkyl carboxylic acid, $C_1$-$C_6$ alkyl carboxylamide and alkylaryl, wherein any group can be singly or multiply substituted with: halogen or amino, and provided that no more than two of $R_1$, $R_2$ and $R_3$ are H. In another embodiment, no more than one of $R_1$, $R_2$ and $R_3$ is H.

In other embodiments, there is provided a pharmaceutical composition comprising a pharmaceutically acceptable carrier, peptide, a cation selected from $Mg^{2+}$, $Ca^{2+}$, $Zn^{2+}$, $Mn^{2+}$, $K^+$, $Na^+$ or $Al^{3+}$, or a mixture thereof, and a sterically hindered primary amine. In one embodiment, the cation is $Mg^{2+}$, $Ca^{2+}$ or $Zn^{2+}$ or a mixture thereof. In a further embodiment, the pharmaceutical composition further comprises a pharmaceutically acceptable binder and/or a pharmaceutically acceptable glidant, lubricant or additive that acts as both a glidant and lubricant and/or an antioxidant. In some embodiments, the pharmaceutical composition is applied to a carrier. In some embodiments, the carrier is a filler.

In some cases the molar ratio of cation: sterically hindered primary amine: peptide in the aqueous solution applied to the carrier is 5-100:5-50:1. In some cases, the molar ratio of cation: sterically hindered primary amine may be equal to or greater than 2:1 (e.g., between 5:1 and 2:1). Thus, in some cases the molar ratio of cation:sterically hindered primary amine: peptide applied to the carrier is 100:50:1, 100:30:1, 80:40:1, 80:30:1, 80:20:1, 60:30:1, 60:20:1, 50:30:1, 50:20:1, 40:20:1, 20:20:1, 10:10:1, 10:5:1 or 5:10:1. When binder, e.g., methylcellulose, is present in the GC-C agonist peptide solution applied to the carrier it can be present at 0.5%-2.5% by weight (e.g., 0.7%-1.7% or 0.7%-1% or 1.5% or 0.7%).

It has been found that a cation selected from $Mg^{2+}$, $Ca^{2+}$, $Zn^{2+}$, $Mn^{2+}$, $K^+$, $Na^+$ and $Al^{3+}$ is useful for suppressing the formation of an oxidation product of GC-C receptor agonist polypeptides during storage. It has also been found that a sterically hindered primary amine is useful for suppressing the formation of a formaldehyde imine adduct ("formaldehyde imine product") of the GC-C receptor agonist polypeptides during storage. Thus, the GC-C receptor agonist polypeptide formulations comprising a cation selected from $Mg^{2+}$, $Ca^{2+}$, $Zn^{2+}$, $Mn^{2+}$, $K^+$, $Na^+$ or $Al^{3+}$—for example, a divalent cation selected from $Zn^{2+}$, $Mg^{2+}$ and $Ca^{2+}$—and/or a sterically hindered primary amine, such as an amino acid, have a sufficient shelf life (as measured by chromatographic purity and/or by a weight/weight assay) for manufacturing, storing and distributing the drug. Further, while the presence of a sterically hindered amine alone can increase the formation of a hydrolysis product of GC-C receptor agonist polypeptides during storage, the combination of a sterically hindered primary amine and a cation, e.g., but not limited to, the combination of leucine and $Ca^{2+}$, suppresses the formation of the hydrolysis product of the GC-C receptor agonist polypeptide as well as the oxidation product of GC-C receptor agonist polypeptide during storage, leading to an even greater overall stability as determined by a weight/weight assay and/or by chromatographic purity.

In a further embodiment, the pharmaceutical composition further comprises a pharmaceutically acceptable binder or additive, and/or a pharmaceutically acceptable glidant, lubricant or additive that acts as both a glidant and lubricant and/or an antioxidant.

Suitable pharmaceutical compositions in accordance with the invention will generally include an amount of the active compound(s) with an acceptable pharmaceutical diluent or excipient, such as a sterile aqueous solution, to give a range of final concentrations, depending on the intended use. The techniques of preparation are generally well known in the art, as exemplified by Remington's Pharmaceutical Sciences (18th Edition, Mack Publishing Company, 1995).

For treatment of gastrointestinal disorders, the peptides described herein are administered orally or rectally, e.g., as a tablet, capsule, sachet containing a predetermined amount of the active ingredient pellet, gel, paste, syrup, bolus, electuary, slurry, powder, lyophilized powder, granules, as a solution or a suspension in an aqueous liquid or a nonaqueous liquid; as an oil-in-water liquid emulsion or a water-in-oil liquid emulsion, via a liposomal formulation (see, e.g., EP 736299) or in some other form. Orally administered compositions can include binders, lubricants, inert diluents, lubricating, surface active or dispersing agents, flavoring agents, and humectants. Orally administered formulations such as tablets may optionally be coated or scored and may be formulated so as to provide sustained, delayed or controlled release of the active ingredient therein. The peptides can be co-administered with other agents used to treat gastrointestinal disorders including but not limited to the agents described herein.

In another aspect, suitable pharmaceutical compositions may comprise one or more other therapeutic agents. Such therapeutic agents include, without limitation, analgesic agents; anti-secretory agents, including proton pump inhibitors, acid pump antagonists, H2 receptor antagonists; PDE5 inhibitors; ODC inhibitors; GABA-B antagonists; bile acid sequestrants; prokinetic and promotility agents; antidepressants; antibiotics; antiemetics; opioids; and mucosal-protecting agents.

Methods of Treatment

In various embodiments, the peptides or the pharmaceutically acceptable salts thereof may be useful in methods for colon cleansing treatments or the treatment of gastrointestinal disorders. In some embodiments, the peptides or pharmaceutically acceptable salts thereof may be useful in a method for cleansing the colon prior to a colonoscopy or surgical procedure. In further embodiments, the peptides may be used to prepare subjects for colonoscopy treatment. In some embodiments, the peptides or pharmaceutically acceptable salts may be used to prepare subjects for surgery, such as bowel surgery. In other embodiments, the peptides may be used to treat gastrointestinal disorders, visceral disorders, colon cancer, Hereditary Nonpolyposis Colorectal Cancer (HNPCC), i.e. Lynch syndrome, gastroparesis (GP), polyps, pain, general abdominal pain, post-operative ileus, opioid-induced constipation, functional dyspepsia, diverticular disease including but not limited to SUDD (symptomatic uncomplicated diverticular disease) and SCAD (segmental colitis associated with diverticulosis), diverticulosis, diarrhea-predominant irritable bowel syndrome, pain associated with irritable bowel syndrome (IBS), ulcerative colitis, ulcerative proctitis, Crohn's Disease, inflammatory bowel disease (IBD), chronic or acute radiation protopathy, rectal pain, chronic proctalgia, proctalgia fugax, anal pain, chronic anal fissure, post-operative anal pain, overactive bladder syndrome, stress incontinence, interstitial cystitis, bladder pain syndrome, colorectal cancer, pain associated with cancer, general pelvic pain, endometriosis, orchialgia, chronic prostatitis, prostatodynia, vulvodynia, urethral syndrome, penile pain, perianal pain and other gastrointestinal and visceral disorders. In some embodiments of the invention, a method of treatment is provided for gastrointestinal disorders. In one embodiment, the gastrointestinal disorder is colon cancer or polyps. In another embodiment, the gastrointestinal disorder is Hereditary Nonpolyposis Colorectal Cancer (HNPCC), i.e. Lynch syndrome. In another embodiment, the gastrointestinal disorder is gastrointestinal pain. In a further embodiment, the gastrointestinal disorder is visceral or abdominal pain or pain associated with cancer. In another embodiment, the gastrointestinal disorder is rectal cancer. In another embodiment, the gastrointestinal disorder is functional dyspepsia.

In one embodiment, a method is provided for cleansing the colon of a subject in preparation for a colonoscopy procedure comprising administering to the subject an effective dose of a colon cleansing composition, wherein the colon cleansing composition comprises a pharmaceutically acceptable excipient, diluent or carrier, and a peptide or a pharmaceutically acceptable salt thereof, wherein the peptide or a pharmaceutically acceptable salt thereof comprises the amino acid sequence:

$Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Ala_{15}$ $Xaa_{16}$ $Xaa_{17}$ $Gly_{18}$ $Xaa_{19}$ $Xaa_{20}$ $X_{21}$ (SEQ ID NO: 1), or a pharmaceutically acceptable salt thereof; wherein $Xaa_1$ is BE or is absent;

$Xaa_2$ is BK, Asn or is absent;

$Xaa_3$ is Asn, Ser or is absent;

$Xaa_4$ is Ser or is absent;

$Xaa_5$ is Ser, Asn, Ile, BE or is absent;

$Xaa_6$ is Tyr, Asp, 4-fluorophenylalanine ((4-F)Phe), BK or is absent;

$Xaa_7$ is Cys, cystathionine (Cth), allylglycine (Ag), Hag, or Asp;

$Xaa_8$ is Cys, cystathionine (Cth), penicillamine (Pen), or allylglycine (Ag);

$Xaa_9$ is Glu, Asp, Ser, Thr, or Gln;

$Xaa_{10}$ is Leu, cyclohexylalanine (Cha), Phe, or 4-fluorophenylalanine ((4-F)Phe);

$Xaa_{11}$ is Cys, Ag, or penicillamine (Pen);

$Xaa_{12}$ is Cys, allylglycine (Ag), Hag, Cth, Dpr, or Val;

$Xaa_{13}$ is Asn or Leu;

$Xaa_{14}$ is Pro, Val, sarcosine (Sar), Leu, or Hydroxyproline (OH-Pro);

$Xaa_{16}$ is Cys, Ag, Pen or Cth;

$Xaa_{17}$ is Tyr, Thr, cyclohexylalanine (Cha), 4-fluorophenylalanine ((4-F)Phe), Phe, Ser, or Ala;

$Xaa_{19}$ is Cys, Ag or Pen;

$Xaa_{20}$ is Tyr, Leu, 4-fluorophenylalanine ((4-F)Phe), cyclohexylalanine (Cha), D-Tyr, N-Methyl Tyr (Nme-Tyr) or is absent;

$Xaa_{21}$ is absent or Asn;

wherein at least one Xaa is BE, BK, (4-F)Phe, Cth, Ag, Hag, Pen, Cha, Sar, Dpr, or OH-Pro and wherein the peptide contains a covalent bond between $Xaa_7$ and $Xaa_{12}$, $Xaa_8$ and $Xaa_{16}$, and $Xaa_{11}$ and $Xaa_{19}$.

In another embodiment, a method is provided for cleansing the colon of a subject in preparation for a colonoscopy procedure comprising administering to the subject an effective dose of a colon cleansing composition, wherein the colon cleansing composition comprises a pharmaceutically acceptable excipient, diluent or carrier, and a peptide or a pharmaceutically acceptable salt thereof, wherein the peptide or a pharmaceutically acceptable salt thereof comprises the amino acid sequence:

(SEQ ID NO: 2)
H-Ag Cys Glu Leu Cys Ag Asn Pro Ala Cys Thr Gly Cys Tyr-$NH_2$;

(SEQ ID NO: 3)
C12-BE BK Asn Ser Ser Tyr Cys Cys Glu Leu Cys Cys Asn Pro Ala Cys Thr Gly Cys Tyr-$NH_2$;

-continued

```
                                             (SEQ ID NO: 4)
C16-BE BK Asn Ser Ser Tyr Cys Cys Glu Leu Cys Cys Asn Pro Ala Cys

Thr Gly Cys Tyr-NH₂;

(SEQ ID NO: 5)
C12-BE BK Asn Ser Ser Tyr Cys Cys Glu Leu Cys Cys Asn Pro Ala Cys

Thr Gly Cys Tyr-COOH;

(SEQ ID NO: 6)
C14-BE BK Asn Ser Ser Tyr Cys Cys Glu Leu Cys Cys Asn Pro Ala Cys

Thr Gly Cys Tyr-COOH;

(SEQ ID NO: 7)
C16-BE BK Asn Ser Ser Tyr Cys Cys Glu Leu Cys Cys Asn Pro Ala Cys

Thr Gly Cys Tyr-COOH;

(SEQ ID NO: 8)
H-Cys Ag Glu Leu Cys Cys Asn Pro Ala Ag Thr Gly Cys Tyr-NH₂;

(SEQ ID NO: 9)
H-Asn Asp Asp Ag Glu Leu Cys Val Asn Val Ala Ag Thr Gly Cys Leu-

NH₂;

(SEQ ID NO: 10)
H-Asn Asp Asp Cys Glu Leu Ag Val Asn Val Ala Cys Thr Gly Ag Leu-

NH₂;

(SEQ ID NO: 11)
C18-BE BK Asn Ser Ser Tyr Cys Cys Glu Leu Cys Cys Asn Pro Ala Cys

Thr Gly Cys Tyr-COOH;

(SEQ ID NO: 12)
H-Ag Cys Glu Leu Cys Ag Asn Pro Ala Cys Thr Gly Cys-NH₂;

(SEQ ID NO: 13)
H-Ag Cys Glu Leu Cys Ag Asn Pro Ala Cys Ala Gly Cys-NH₂;

(SEQ ID NO: 14)
H-Ag Cys Glu Phe Cys Ag Asn Pro Ala Cys Thr Gly Cys Tyr-NH₂;

(SEQ ID NO: 15)
H-Ag Cys Glu (4-F)Phe Cys Ag Asn Pro Ala Cys Thr Gly Cys-NH₂;

(SEQ ID NO: 16)
H-Ag Cys Glu (4-F)Phe Cys Ag Asn Pro Ala Cys Thr Gly Cys Tyr-NH₂;

(SEQ ID NO: 17)
H-Ag Cys Glu (4-F)Phe Cys Ag Asn Pro Ala Cys Thr Gly Cys (4-F)Phe-

NH₂;

(SEQ ID NO: 18)
H-Cys Cys Glu Leu Ag Cys Asn Pro Ala Cys Thr Gly Ag Tyr-NH₂;

(SEQ ID NO: 19)
H-Ag Cys Glu Phe Cys Ag Asn Pro Ala Cys Thr Gly Cys-NH₂;

(SEQ ID NO: 20)
H-Ag Cys Glu Phe Cys Ag Asn Pro Ala Cys Thr Gly Cys (4-F)Phe-NH₂;

(SEQ ID NO: 21)
H-Cys Cys Glu (4-F)Phe Cys Cys Asn Pro Ala Cys Thr Gly Cys Tyr-NH₂;

(SEQ ID NO: 22)
H-Cys Cys Glu (4-F)Phe Cys Cys Asn Pro Ala Cys Thr Gly Cys (4-F)Phe-

NH₂;

(SEQ ID NO: 23)
H-Ag Cys Glu Leu Cys Ag Asn Pro Ala Cys Thr Gly Cys (4-F)Phe-NH₂;
```

-continued (SEQ ID NO: 24)
H-(4-F)Phe Ag Cys Glu Leu Cys Ag Asn Pro Ala Cys Thr Gly Cys (4-F)Phe-NH$_2$;

(SEQ ID NO: 25)
H-Ag Cys Glu Leu Cys Ag Asn Pro Ala Cys Ala Gly Cys Tyr-NH$_2$;

(SEQ ID NO: 26)
H-Ag Cys Glu Leu Cys Ag Asn Pro Ala Cys Tyr Gly Cys Tyr-NH$_2$;

(SEQ ID NO: 27)
H-Ag Cys Glu Leu Cys Ag Asn Pro Ala Cys Phe Gly Cys Tyr-NH$_2$;

(SEQ ID NO: 28)
H-Ag Cys Glu Leu Cys Ag Asn Pro Ala Cys (4-F)Phe Gly Cys Tyr-NH$_2$;

(SEQ ID NO: 29)
H-Ag Cys Glu Leu Cys Ag Asn Pro Ala Cys Thr Gly Cys Leu-NH$_2$;

(SEQ ID NO: 30)
H-Ag Cys Glu Leu Cys Ag Asn Pro Ala Cys Thr Gly Cys Cha-NH$_2$;

(SEQ ID NO: 31)
H-Ag Cys Glu Cha Cys Ag Asn Pro Ala Cys Thr Gly Cys Tyr-NH$_2$;

(SEQ ID NO: 32)
H-Ag Cys Glu Leu Cys Ag Asn Pro Ala Cys Thr Gly Cys D-Tyr-NH$_2$;

(SEQ ID NO: 33)
H-Ag Pen Glu Leu Cys Ag Asn Pro Ala Pen Thr Gly Cys Tyr-NH$_2$;

(SEQ ID NO: 34)
H-Ag Cys Glu Leu Cys Ag Asn Pro Ala Cys Thr Gly Cys Leu Asn-NH$_2$;

(SEQ ID NO: 35)
H-Ag Cys Glu Leu Cys Ag Asn Pro Ala Cys Thr Gly Cys Tyr Asn-NH$_2$;

(SEQ ID NO: 36)
H-Asp Ag Cys Glu Leu Cys Ag Asn Pro Ala Cys Thr Gly Cys Tyr-NH$_2$;

(SEQ ID NO: 37)
H-Ile Asp Ag Cys Glu Leu Cys Ag Asn Pro Ala Cys Thr Gly Cys Tyr-NH$_2$;

(SEQ ID NO: 38)
H-Ag Cys Glu Leu Cys Ag Asn OH-Pro Ala Cys Thr Gly Cys Tyr-NH$_2$;

(SEQ ID NO: 39)
H-Ag Cys Glu Leu Cys Ag Asn OH-Pro Ala Cys Thr Gly Cys-NH$_2$;

(SEQ ID NO: 40)
H-Ag Cys Glu Leu Pen Ag Asn Pro Ala Cys Thr Gly Pen Tyr-NH$_2$;

(SEQ ID NO: 41)
H-Ag Cys Glu Leu Pen Ag Asn Pro Ala Cys Thr Gly Pen Tyr-NH$_2$;

(SEQ ID NO: 42)
H-Ag Cys Glu Leu Cys Ag Asn Pro Ala Cys Tyr Gly Cys Nme-Tyr-NH$_2$;

(SEQ ID NO: 43)
H-Ag Cys Glu Leu Cys Ag Asn Pro Ala Cys Tyr Gly Cys-COOH;

(SEQ ID NO: 44)
H-Ag Cys Glu Leu Cys Ag Asn Pro Ala Cys Cha Gly Cys Tyr-NH$_2$;

(SEQ ID NO: 45)
H-Ag Cys Glu Leu Cys Ag Asn Leu Ala Cys Thr Gly Cys Tyr-NH$_2$;

(SEQ ID NO: 46)
H-Ag Cys Glu Leu Cys Ag Asn Sar Ala Cys Thr Gly Cys Tyr-NH$_2$;

(SEQ ID NO: 47)
H-Ag Cys Glu Leu Cys Ag Asn Val Ala Cys Thr Gly Cys Tyr-NH$_2$;

(SEQ ID NO: 48)
H-Ag Cys Glu Leu Cys Ag Asn Pro Ala Cys Tyr Gly Cys Nme-Tyr-NH$_2$;

```
                                                        (SEQ ID NO: 49)
H-Ag Cys Glu Leu Cys Ag Leu Pro Ala Cys Tyr Gly Cys-COOH;

(SEQ ID NO: 50)
H-Ag Cys Asp Leu Cys Ag Asn Pro Ala Cys Tyr Gly Cys-COOH;

(SEQ ID NO: 51)
H-Ag Cys Ser Leu Cys Ag Asn Pro Ala Cys Tyr Gly Cys-COOH;

(SEQ ID NO: 52)
H-Ag Cys Thr Leu Cys Ag Asn Pro Ala Cys Tyr Gly Cys-COOH;

(SEQ ID NO: 53)
H-Hag Cys Glu Leu Cys Hag Asn Pro Ala Cys Thr Gly Cys Tyr-NH₂;

(SEQ ID NO: 54)
H-Ag Cys Gln Leu Cys Ag Asn Pro Ala Cys Tyr Gly Cys-COOH;

(SEQ ID NO: 55)
H-Ag Cys Glu Leu Cys Ag Leu Pro Ala Cys Thr Gly Cys Tyr-NH₂;

(SEQ ID NO: 56)
Pent-Cys Glu Leu Cys Ag Asn Pro Ala Cys Tyr Gly Cys Tyr-NH₂;

(SEQ ID NO: 57)
H-Cys Cys Glu Leu Cys Ag Asn Pro Ala Cys Tyr Gly Ag-COOH;

(SEQ ID NO: 58)
Pent-Cys Glu Leu Cys Ag Asn Pro Ala Cys Tyr Gly Cys-COOH;

(SEQ ID NO: 59)
H-Hag Cys Glu Leu Cys Hag Asn Pro Ala Cys Tyr Gly Cys-COOH;

(SEQ ID NO: 60)
H-Ag Cys Glu Leu Cys Ag Asn Val Ala Cys Tyr Gly Cys Tyr-NH₂;

(SEQ ID NO: 61)
H-Ag Cys Glu Leu Cys Ag Asn Val Ala Cys Tyr Gly Cys-COOH;

(SEQ ID NO: 62)
H-Cys Cth Glu Leu Cys Cys Asn Pro Ala Cys Tyr Gly Cys Tyr-NH₂;

(SEQ ID NO: 63)
H-Cth Cys Glu Leu Cys Cys Asn Pro Ala Cys Tyr Gly Cys Tyr-NH₂;

(SEQ ID NO: 64)
H-Cth Cys Glu Leu Cys Cys Asn Pro Ala Cys Tyr Gly Cys-COOH;

(SEQ ID NO: 65)
H-Cys Cth Glu Leu Cys Cys Asn Val Ala Cys Tyr Gly Cys Tyr-NH₂;

(SEQ ID NO: 66)
H-Cys Cth Glu Leu Cys Cys Asn Val Ala Cys Thr Gly Cys Tyr-NH₂;

(SEQ ID NO: 67)
Ac-Cys Cth Glu Leu Cys Cys Asn Val Ala Cys Thr Gly Cys Tyr-NH₂;

(SEQ ID NO: 68)
Ac-Cys Cth Glu Leu Cys Cys Asn Pro Ala Cys Tyr Gly Cys Tyr-NH₂;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;

(SEQ ID NO: 71)
Ac-Cys Cth Glu Leu Cys Cys Asn Pro Ala Cys Tyr Gly Cys-COOH;

(SEQ ID NO: 72)
H-Cys Cys Glu Leu Cys Asn Val Ala Cth Tyr Gly Cys-COOH;

(SEQ ID NO: 73)
H-Cys Cys Glu Leu Cys Cys Asn Val Ala Cth Tyr Gly Cys Tyr-NH₂;

(SEQ ID NO: 74)
H-Cys Cys Glu Leu Cys Cys Asn Val Ala Cth Thr Gly Cys Tyr-NH₂;

(SEQ ID NO: 75)
H-Cys Cys Glu Leu Cys Cth Asn Val Ala Cys Tyr Gly Cys-COOH;
```

-continued

```
                                                     (SEQ ID NO: 76)
H-Cys Cys Glu Leu Cys Cth Asn Val Ala Cys Tyr Gly Cys Tyr-NH2;

(SEQ ID NO: 77)
H-Cys Cys Glu Leu Cys Cth Asn Val Ala Cys Thr Gly Cys Tyr-NH2;

(SEQ ID NO: 78)
4-Mepip-Cys Cth Glu Leu Cys Cys Asn Val Ala Cys Tyr Gly Cys-COOH;

(SEQ ID NO: 79)
H-Cys Cth Glu Leu Cys Cys Asn Val Ala Cys Thr Gly Cys-COOH;

(SEQ ID NO: 80)
H-Cys Cth Glu Leu Cys Cys Asn Val Ala Cys Thr Gly Cys-NH2;

(SEQ ID NO: 81)
H-Cys Cth Glu Leu Cys Cys Asn Val Ala Cys Phe Gly Cys-COOH;

(SEQ ID NO: 82)
H-Ag Ag Glu Leu Ag Ag Asn Pro Ala Ag Thr Gly Ag Tyr-COOH;

(SEQ ID NO: 83)
H-Cys Cth Glu Leu Cys Cys Asn Ala Ala Cys Thr Gly Cys Tyr-NH2;

(SEQ ID NO: 84)
H-Asp Cys Glu Leu Cys Dpr Asn Val Ala Cys Thr Gly Cys Tyr-NH2;

(SEQ ID NO: 85)
H-Cys Cth Glu Leu Cys Cys Asn Val Ala Cys Ser Gly Cys Tyr-NH2;

(SEQ ID NO: 86)
H-Cth Glu Leu Cys Ag Asn Val Ala Cys Thr Gly Cys Tyr-NH2;

(SEQ ID NO: 87)
H-Ag Cys Glu Leu Cys Ag Asn Val Ala Cys Thr Gly Cys Tyr-NH2;

(SEQ ID NO: 88)
H-Ag Cys Glu Leu Cys Ag Asn Pro Ala Cys Thr Gly Cys Tyr-NH2;

(SEQ ID NO: 89)
H-Cth Cys Glu Leu Cys Cys Asn Val Ala Cys Thr Gly Cys-COOH;

(SEQ ID NO: 90)
H-Cth Cys Glu Leu Cys Cys Asn Val Ala Cys Thr Gly Cys Tyr-NH2;

(SEQ ID NO: 91)
H-Cth Cys Glu Leu Cys Cys Asn Val Ala Cys Tyr Gly Cys Tyr-NH2;
or
                                                     (SEQ ID NO: 92)
H-Cys Cys Glu Leu Cys Cys Asn Val Ala Cth Tyr Gly Cys-COOH.
```

In one embodiment, the peptides and compositions described herein provide a treatment for preparing a patient prior to a colonoscopy.

In some embodiments, the peptides and pharmaceutically acceptable salts described herein may be used as a method for colon cleansing in preparation for a colonoscopy procedure. In some embodiments, the method for colon cleansing comprises administering an effective first dose, such as between 5 μg and 100 mg of the peptide or pharmaceutically acceptable salt. On the following morning, an effective second dose is administered, such as between 5 μg and 100 mg of the peptide or pharmaceutically acceptable salt to substantially cleanse the colon. In other embodiments, the peptide or pharmaceutically acceptable salt thereof is administered in a single dose of between 5 μg and 200 mg.

The peptides and pharmaceutically acceptable salts described herein can be used alone or in combination therapy for the treatment, prevention or reduction of visceral pain associated with a gastrointestinal disorder, cancer, general pelvic pain, bladder pain, overactive bladder, endometriosis, orchialgia, chronic prostatitis, prostatodynia, vulvodynia, urethral syndrome, penile pain, and perianal pain or pain associated with another disorder as described herein.

The peptides and pharmaceutically acceptable salts described herein can be administered in combination with other agents. For example, the peptides can be administered with an analgesic peptide, soluble guanylate cyclase (sGC) stimulator or compound. The analgesic peptide or compound can be covalently attached to a peptide described herein or it can be a separate agent that is administered together with or sequentially with a peptide described herein in a combination therapy. The peptides and pharmaceutically acceptable salts described herein may also be administered in combination with other agents used to treat GI disorders including antidepressants, promotility or prokinetic agents, antiemetics, antibiotics, proton pump inhibitors, acid blockers (e.g., histamine H2 receptor antagonists), acid pump antagonists, PDE5 inhibitors, ODC inhibitors, GABA-B agonists, bile acid sequestrants, COX-2 inhibitors, NSAIDS, corticosteroids, opioids, beta-3 adrenergic receptor agonists, anti-cholinergic agents including but not limited to muscarinic receptor antagonists, tricyclic antidepressants and mucosal protecting agents.

In other embodiments, the therapeutic combinations of the peptides include Celecoxib, other nonsteroidal antiinflammatory drugs (NSAIDS), including Sulidac and isomers, and phosphodiesterase (PDE) inhibitors and ornithine decarboxylase (ODC) inhibitors (e.g. d,l-α-difluoromethylornithine DFMO) for colon polyps-sporadic and Lynch syndrome; Mesalamine or 5-aminosalicylic acid (5-asa), or steroids, Budesonide for inflammatory bowel disease (e.g. Crohns disease and ulcerative colitis); opioids, tramadol, and tramadol isomers and analogs for chronic pain, including cancer pain; or Eluxalodine.

In some embodiments, useful analgesic agents that may be used with the peptides described herein include Ca channel blockers (e.g., ziconotide), 5HT receptor antagonists (e.g., 5HT3, 5HT4 and 5HT1 receptor antagonists), 5HT4 agonists (e.g., tegaserod (Zelnorm®), mosapride, metoclopramide, zacopride, cisapride, renzapride, benzimidazolone derivatives such as BIMU 1 and BIMU 8, and lirexapride), 5HT1 agonists (e.g., sumatriptan and buspirone), opioid receptor agonists (e.g., loperamide, fedotozine, enkephalin pentapeptide, morphine, diphenyloxylate, frakefamide, trimebutine and fentanyl), CCK receptor agonists (e.g., loxiglumide and dexloxiglumide), NK1 receptor antagonists (e.g., aprepitant, vofopitant, ezlopitant, R-673 (Hoffmann-La Roche Ltd), SR-48968 and SR-14033, (Sanofi Synthelabo), CP-122,721 (Pfizer, Inc.), GW679769 (Glaxo Smith Kline) and TAK-637 (Takeda/Abbot)), NK2 receptor antagonists (e.g., nepadutant, saredutant, GW597599 (Glaxo Smith Kline), SR-144190 (Sanofi-Synthelabo) and UK-290795 (Pfizer Inc)), NK3 receptor antagonists (e.g., osanetant (SR-142801; Sanofi-Synthelabo), SR-241586 and talnetant), norepinephrine-serotonin reuptake inhibitors (NSRI) (e.g., milnacipran), vanilloid and cannabanoid receptor agonists, sialorphin and sialorphin-related peptides. Analgesic agents in the various classes are described in the literature.

In some embodiments, one or more other therapeutic agents may be used in combination with the peptides described herein. Such agents include antidepressants, promotility or prokinetic agents, antiemetics, antibiotics, proton pump inhibitors, acid blockers (e.g., histamine H2 receptor antagonists), acid pump antagonists, PDE5 inhibitors, ODC inhibitors, GABA-B agonists, bile acid sequestrants, opioids and mucosal protecting agents.

Examples of antidepressants include, without limitation, tricyclic antidepressants such as amitriptyline (Elavil®), desipramine (Norpramin®), imipramine (Tofranil®), amoxapine (Asendin®), nortriptyline; the selective serotonin reuptake inhibitors (SSRI's) such as paroxetine (Paxil®), fluoxetine (Prozac®), sertraline (Zoloft®), and citralopram (Celexa®); and others such as doxepin (Sinequan®) and trazodone (Desyrel®).

Examples of promotility and prokinetic agents include, without limitation, itopride, octreotide, bethanechol, metoclopramide (Reglan®), domperidone (Motilium®), erythromycin (and derivatives thereof) and cisapride (Propulsid®). An example of antiemetics includes, without limitation, prochlorperazine.

Examples of antibiotics that may be used include those that may be used to treat *Heliobacter pylori* infections, such as amoxicillin, tetracycline, metronidazole, or clarithromycin. Other antibiotics such as erythromycin and derivatives thereof may also be used in combination with the peptides described herein.

Examples of proton pump inhibitors include, without limitation, omeprazole (Prilosec®), esomeprazole (Nexium®), lansoprazole (Prevacid®), pantoprazole (Protonix®) and rabeprazole (Aciphex®). Examples of H2 receptor blockers include, without limitation, including cimetidine, ranitidine, famotidine and nizatidine. Examples of acid pump antagonists include, without limitation, revaprazan, CS-526 (J. Pharmacol. Exp. Ther. (2007) 323: 308-317), PF-03716556 (J. Pharmacol. Exp. Ther. (2009) 328(2):671-9), and YH1885 (Drug Metab. Dispos. (2001) 29(1):54-9).

Examples of PDE5 inhibitors include, without limitation, avanafil, lodenafil, mirodenafil, sildenafil citrate, tadalafil, vardenafil and udenafil. GABA-B agonists include, without limitation, baclofen and XP19986 (CAS Registry No. 847353-30-4). Examples of bile acid sequestrants include, without limitation, GT102-279, cholestyramine, colesevelam, colesevelam hydrochloride, ursodeoxycholic acid, colestipol, colestilan, sevelamer, polydiallylamine cross-linked with epichlorohydrin, dialkylaminoalkyl derivatives of a cross-linked dextran, and N-(cycloalkyl)alkylamines. Examples of mucosal protecting agents include, without limitation, sucralfate (Carafate), teprenone, polaprezinc, cetraxate and bismuth subsalicylate.

Combination therapy can be achieved by administering two or more active agents, e.g., a peptide or pharmaceutically acceptable salt described herein and another therapeutic peptide or compound, each of which is formulated and administered separately, or by administering two or more active agents in a single formulation. Other combinations are also encompassed by combination therapy. For example, two active agents can be formulated together and administered in conjunction with a separate formulation containing a third active agent. While the two or more active agents in the combination therapy can be administered simultaneously, they need not be. For example, administration of a first active agent (or combination of active agents) can precede administration of a second agent (or combination of agents) by minutes, hours, days, or weeks. Thus, the two or more active agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more active agents used in a combination therapy be present in within the patient's body at the same time, this need not be so.

Dosage

The dose range for adult humans may be generally from 5µg to 100 mg/day orally or rectally for the peptides and pharmaceutically acceptable salts described herein. Tablets, capsules, or other forms of presentation provided in discrete units may conveniently contain an amount of compound described herein which is effective at such dosage or as a multiple of the same, for instance, units containing 25 µg to 2 mg or around 100 µg to 1 mg. The precise amount of compound prescribed to a patient will be the responsibility of the attendant physician. However, the dose employed will depend on a number of factors, including the age and sex of the patient, the precise disorder being treated, and its severity.

In various embodiments, the dosage unit is administered with food at anytime of the day, without food at anytime of the day, with food after an overnight fast (e.g. with breakfast), at bedtime after a low fat snack. In one particular embodiment, the dosage unit is administered prior to or subsequent to food consumption (e.g., a meal). In a further embodiment, the dosage unit is administered approximately 15 minutes to 1 hour prior to food consumption. In various embodiments, the dosage unit is administered once a day, twice a day, three times a day, four times a day, five times a day or six times a day. In certain embodiments the dosage unit and daily dose are equivalent.

In some embodiments, a composition containing the peptides described herein is provided in a split dose. The split dose is administered the night before and the day of the colonoscopy. In other embodiments, the dosage is provided in a single dose the night or day before or on the day of the colonoscopy.

In combination therapy embodiments of the present invention, the precise amount of each of the two or more active ingredients in a dosage unit will depend on the desired dosage of each component. Thus, it can be useful to create a dosage unit that will, when administered according to a particular dosage schedule (e.g., a dosage schedule specifying a certain number of units and a particular timing for administration), deliver the same dosage of each component as would be administered if the patient was being treated with only a single component. In other circumstances, it might be desirable to create a dosage unit that will deliver a dosage of one or more components that is less than that which would be administered if the patient was being treated only with a single component. Finally, it might be desirable to create a dosage unit that will deliver a dosage of one or more components that is greater than that which would be administered if the patient was being treated only with a single component.

The pharmaceutical composition can include additional ingredients including but not limited to the active ingredients and excipients described herein. In certain embodiments, one or more therapeutic agents of the dosage unit may exist in an extended or control release formulation and additional therapeutic agents may not exist in extended release formulation. For example, a peptide or agonist described herein may exist in a controlled release formulation or extended release formulation in the same dosage unit with another agent that may or may not be in either a controlled release or extended release formulation. Thus, in certain embodiments, it may be desirable to provide for the immediate release of one or more of the agents described herein, and the controlled release of one or more other agents.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

EXAMPLES

Example 1 cGMP Accumulation in T84 Cells for Analysis of GC-C Activity

For the cGMP assay, $2.0 \times 10^5$ cells/mL of T84 cells were grown overnight in 96 well tissue culture plates. On the next day, the T84 cells were washed twice with 200 μL of DMEM+20 mM MES (pH 5) or DMEM+50 mM sodium bicarbonate (pH8) pr DMEM with no additive for pH 7. These buffers do not contain serum. After the second wash, the cells were incubated with 180 82 L of 1 mM isobutylmethylxanthine (IBMX) in either the pH 5, 7 or 8 buffers for 10 minutes at 37° C. to inhibit any phosphodiesterase activity. The peptides were then diluted in either pH 5, 7 or 8 buffer to a 10× concentration. The peptide solution of 20 μL was diluted to a final volume of 200 μL with the T84 cells, bringing each peptide concentration to 1×. An eleven point curve analysis was conducted for each peptide, with final peptide concentrations tested in each assay, in nM: 10000, 3000, 1000, 300, 100, 30, 10, 3, 1, 0.3, 0.1.

Figure 3:
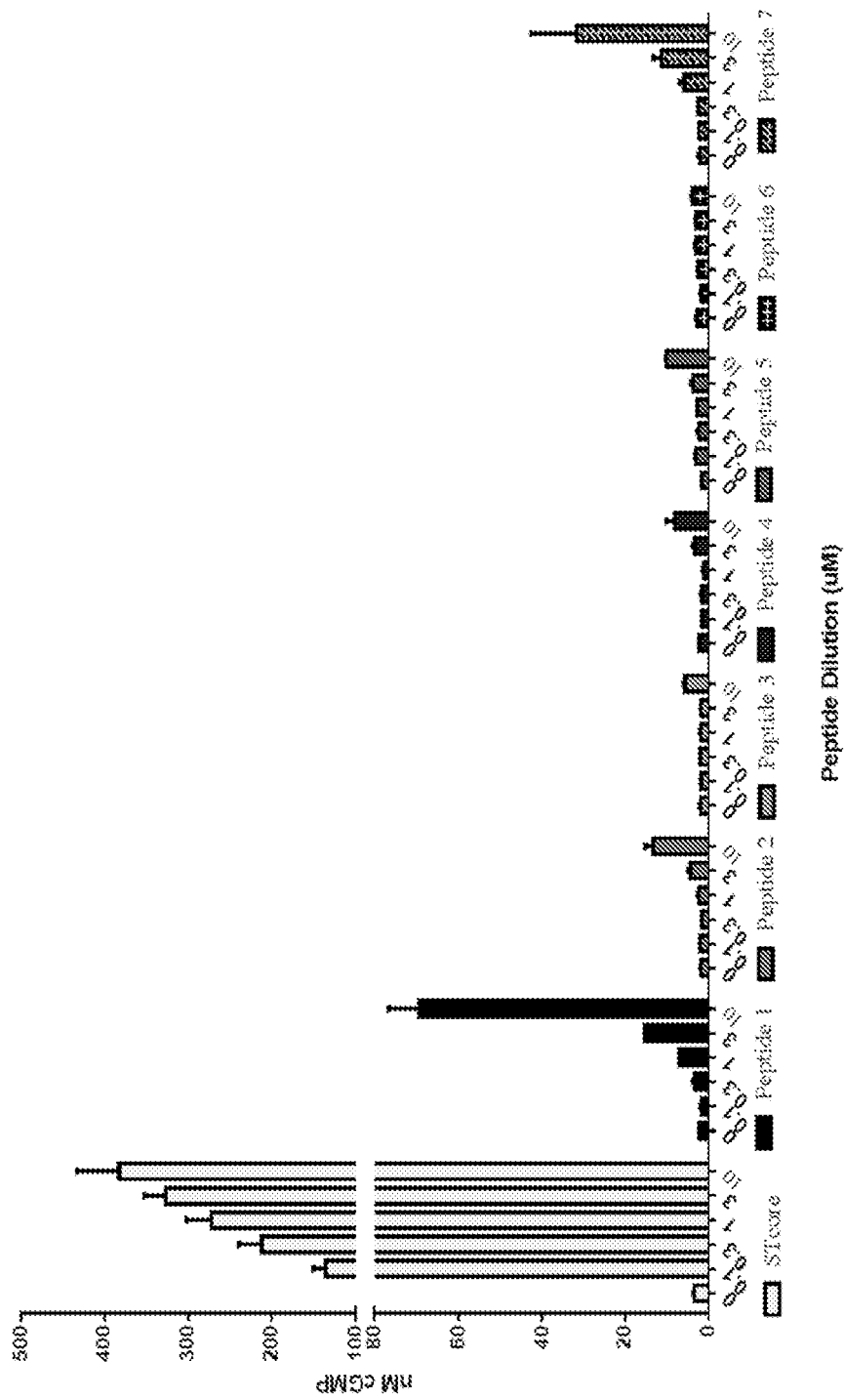
FIG. 3 illustrates the results of a cGMP accumulation in T84 cell assay for analysis of GC-C activity for SEQ ID NOs 8-10.
Figure 5:
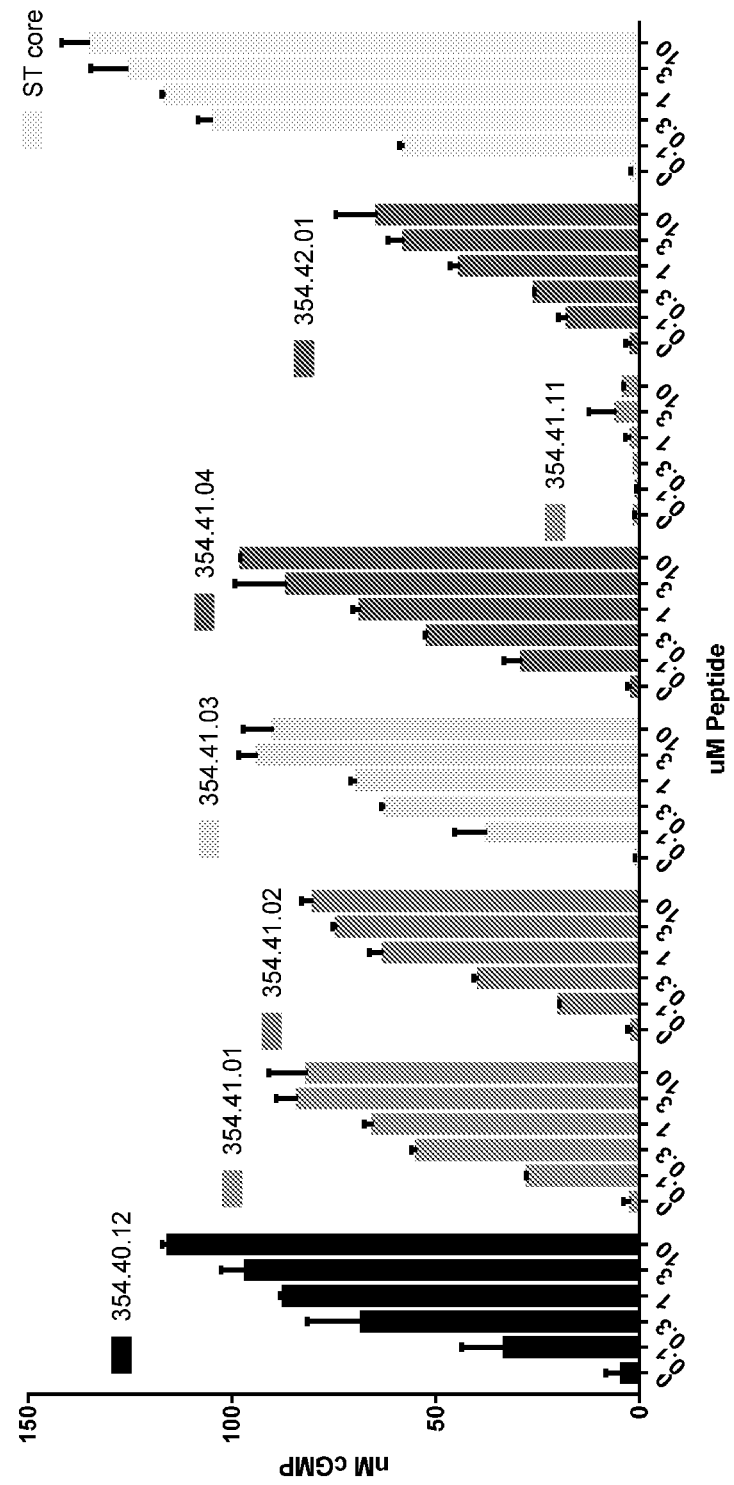
FIG. 5 illustrates the results of a cGMP accumulation in T84 cell assay for analysis of GC-C activity for SEQ ID NOs 28-34.
Figure 6:
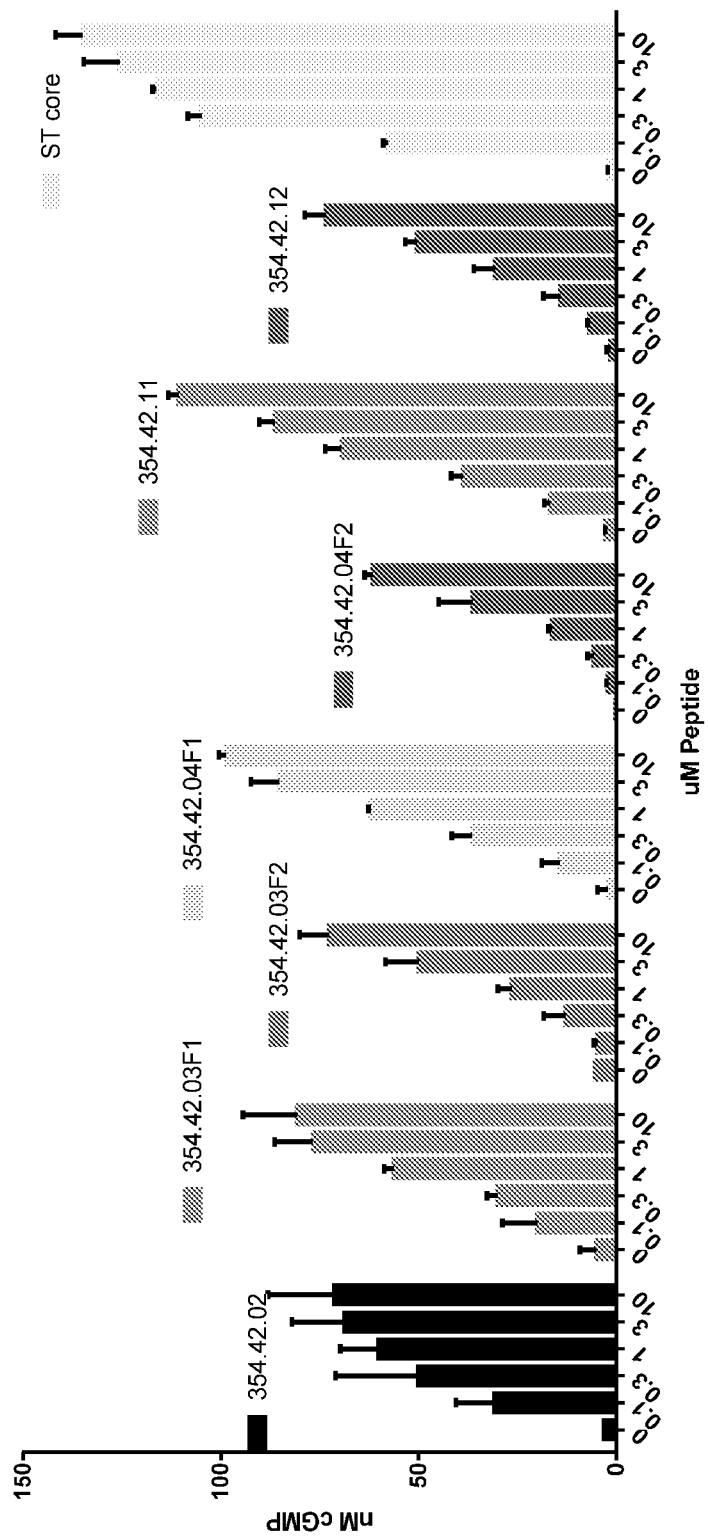
FIG. 6 illustrates the results of a cGMP accumulation in T84 cell assay for analysis of GC-C activity for SEQ ID NOs 35-37, 39 and 44.
Figure 7:
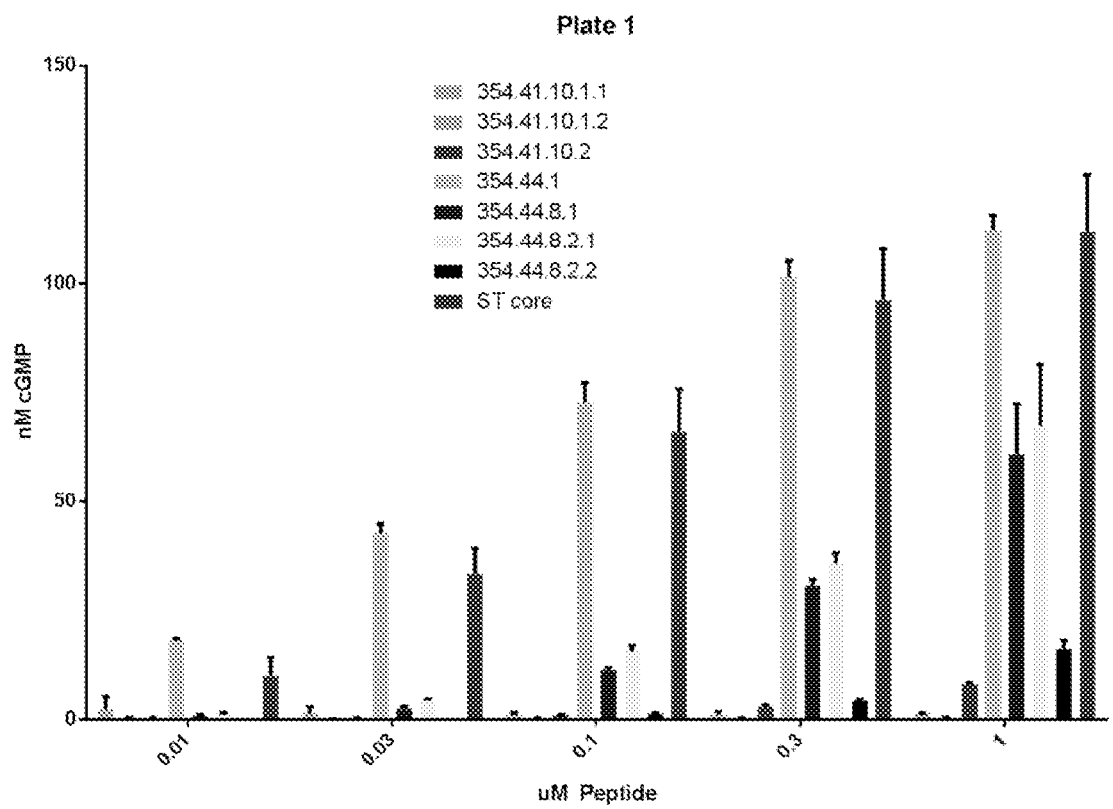
FIG. 7 illustrates the results of a cGMP accumulation in T84 cell assay for analysis of GC-C activity for SEQ ID NOs 2 and 40-42.
Figure 8:
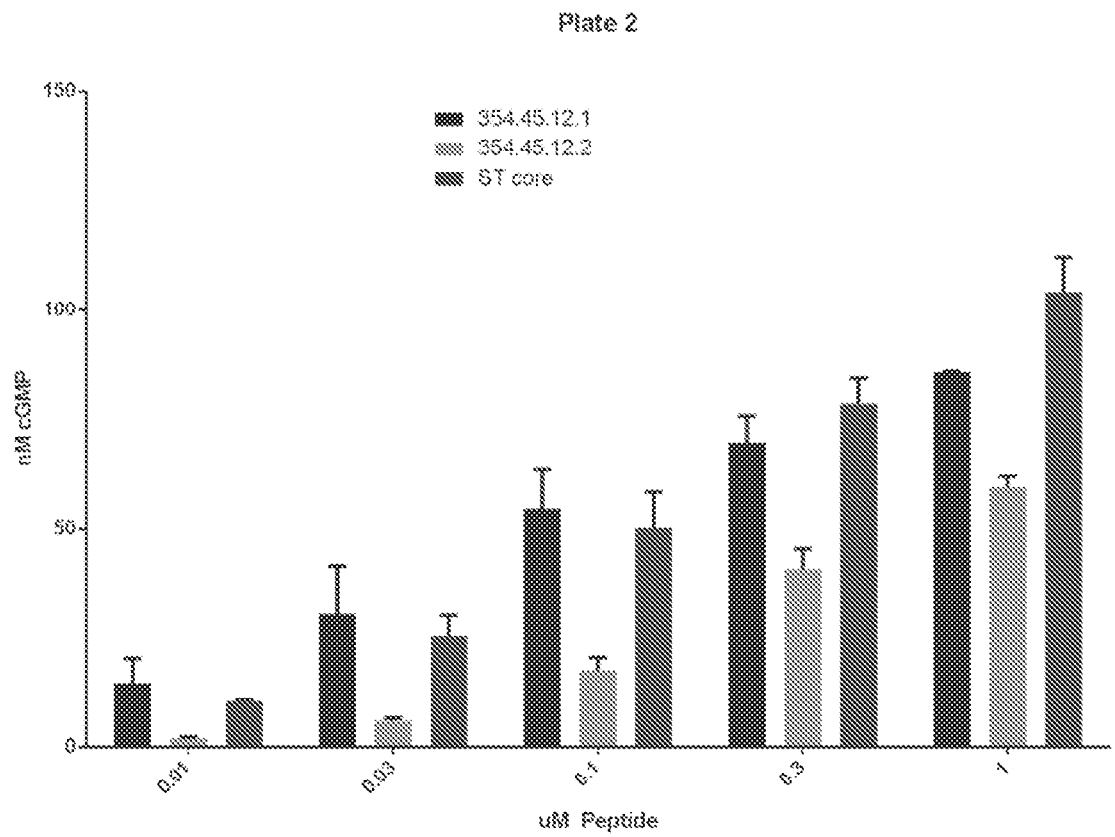
FIG. 8 illustrates the results of a cGMP accumulation in T84 cell assay for analysis of GC-C activity for SEQ ID NO 43.
Figure 9:
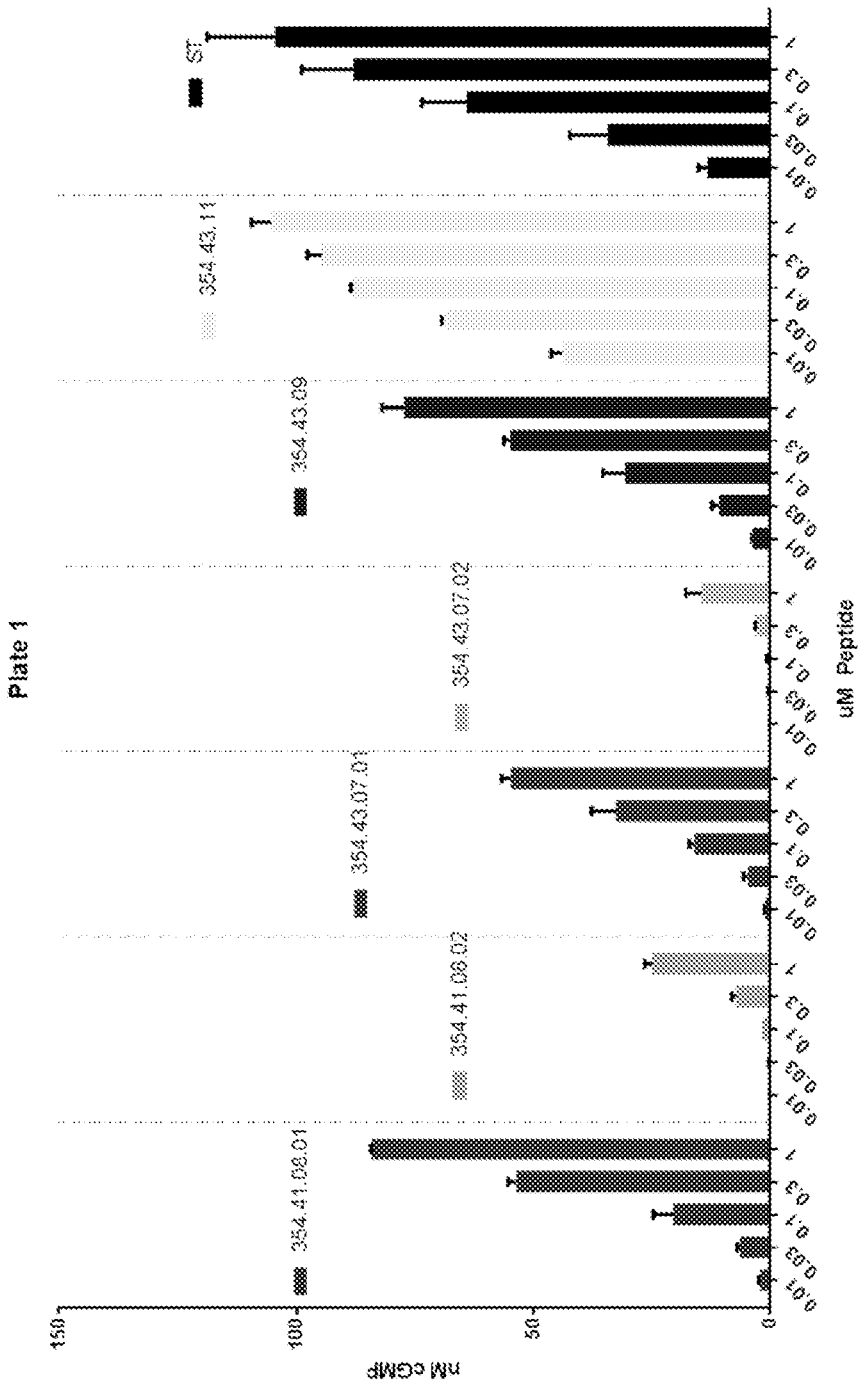
FIG. 9 illustrates the results of a cGMP accumulation in T84 cell assay for analysis of GC-C activity for SEQ ID NOs 44-47.
Figure 10:
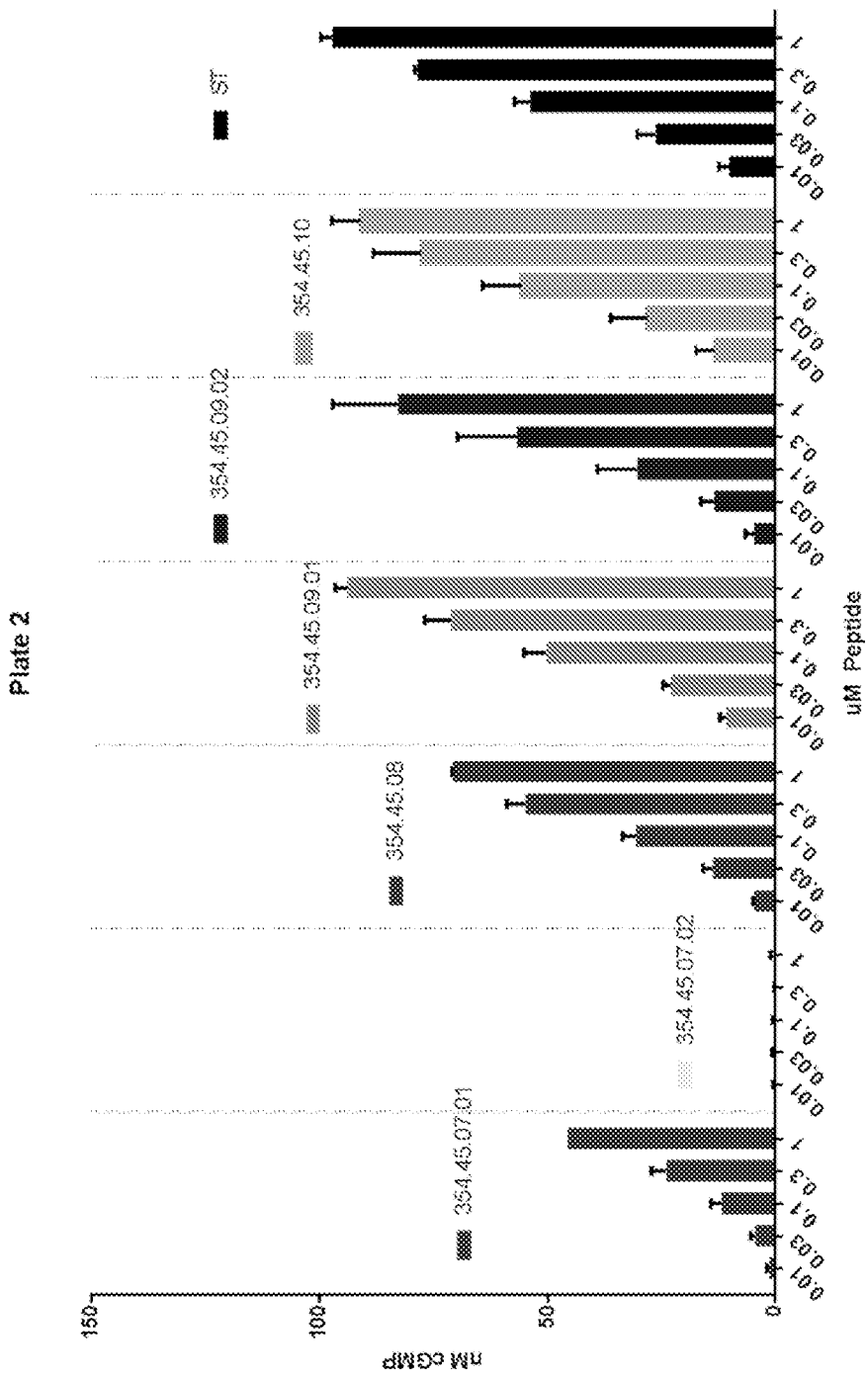
FIG. 10 illustrates the results of a cGMP accumulation in T84 cell assay for analysis of GC-C activity for SEQ ID NOs 45, 48 and 51-52.
Figure 11:
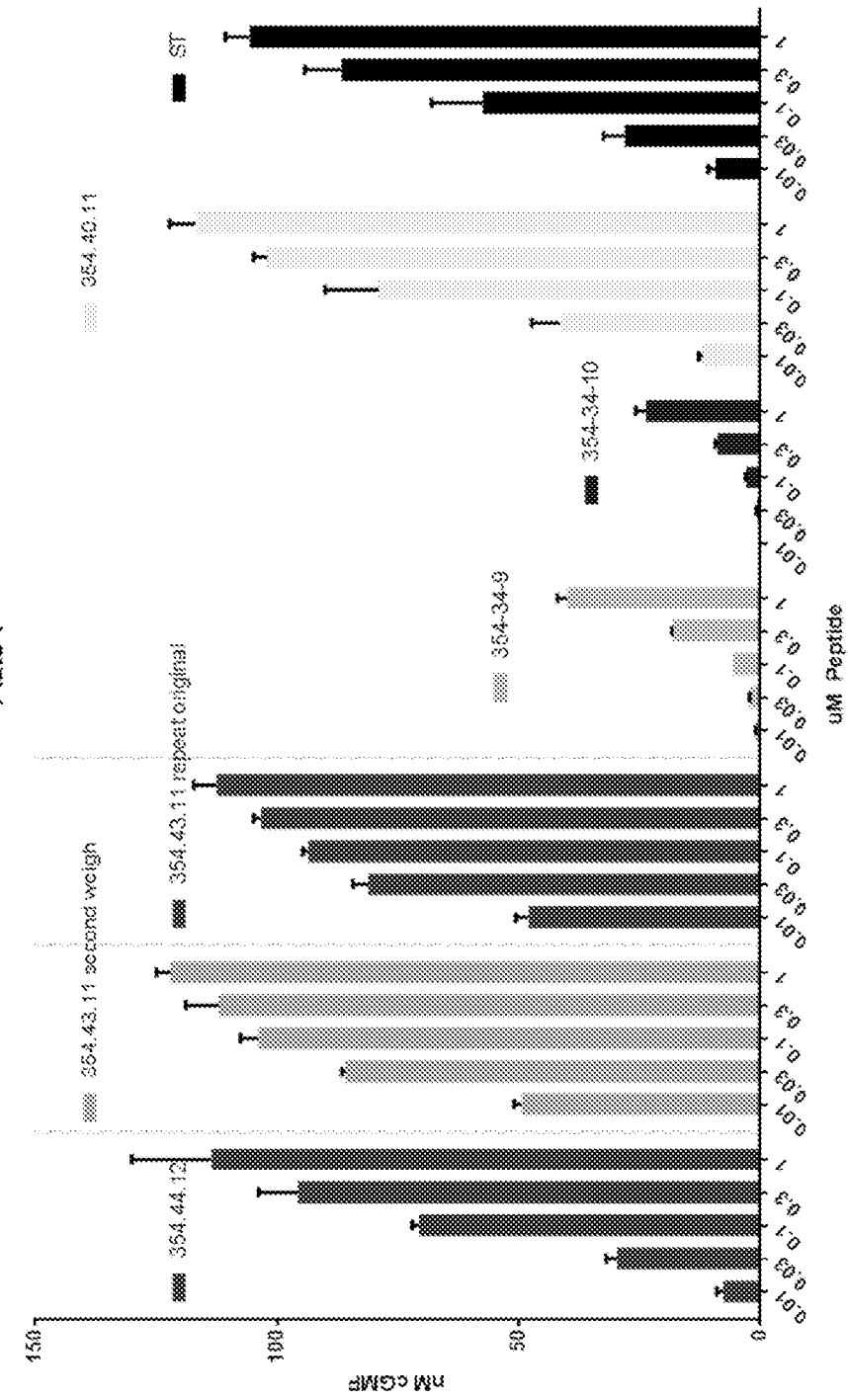
FIG. 11 illustrates the results of a cGMP accumulation in T84 cell assay for analysis of GC-C activity for SEQ ID NOs 12, 13, 27, 47 and 53.
Figure 12:
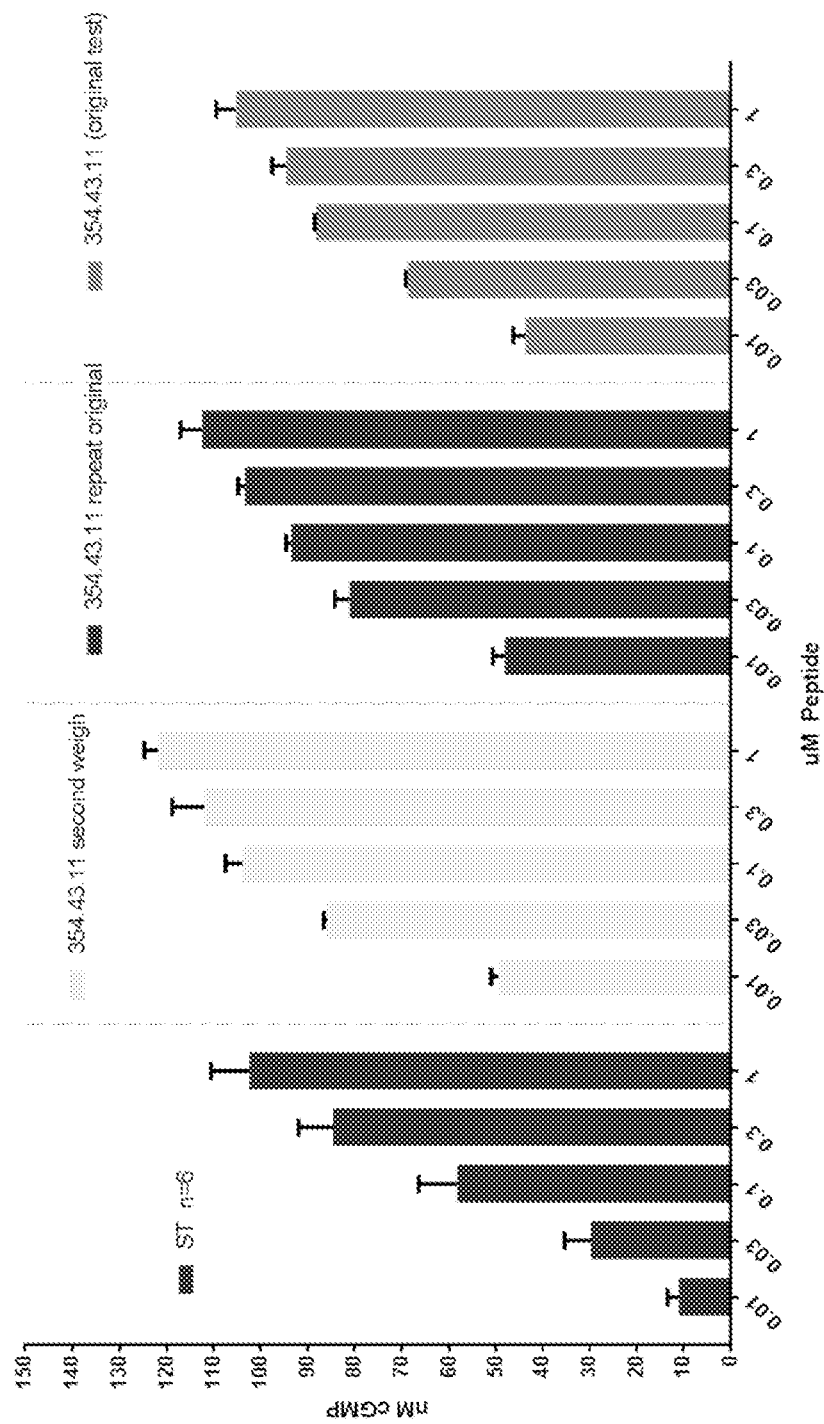
FIG. 12 illustrates the results of a cGMP accumulation in T84 cell assay for analysis of GC-C activity for SEQ ID NO 47 with an original test, a repetition of the original test, and a second weighing.
Figure 13:
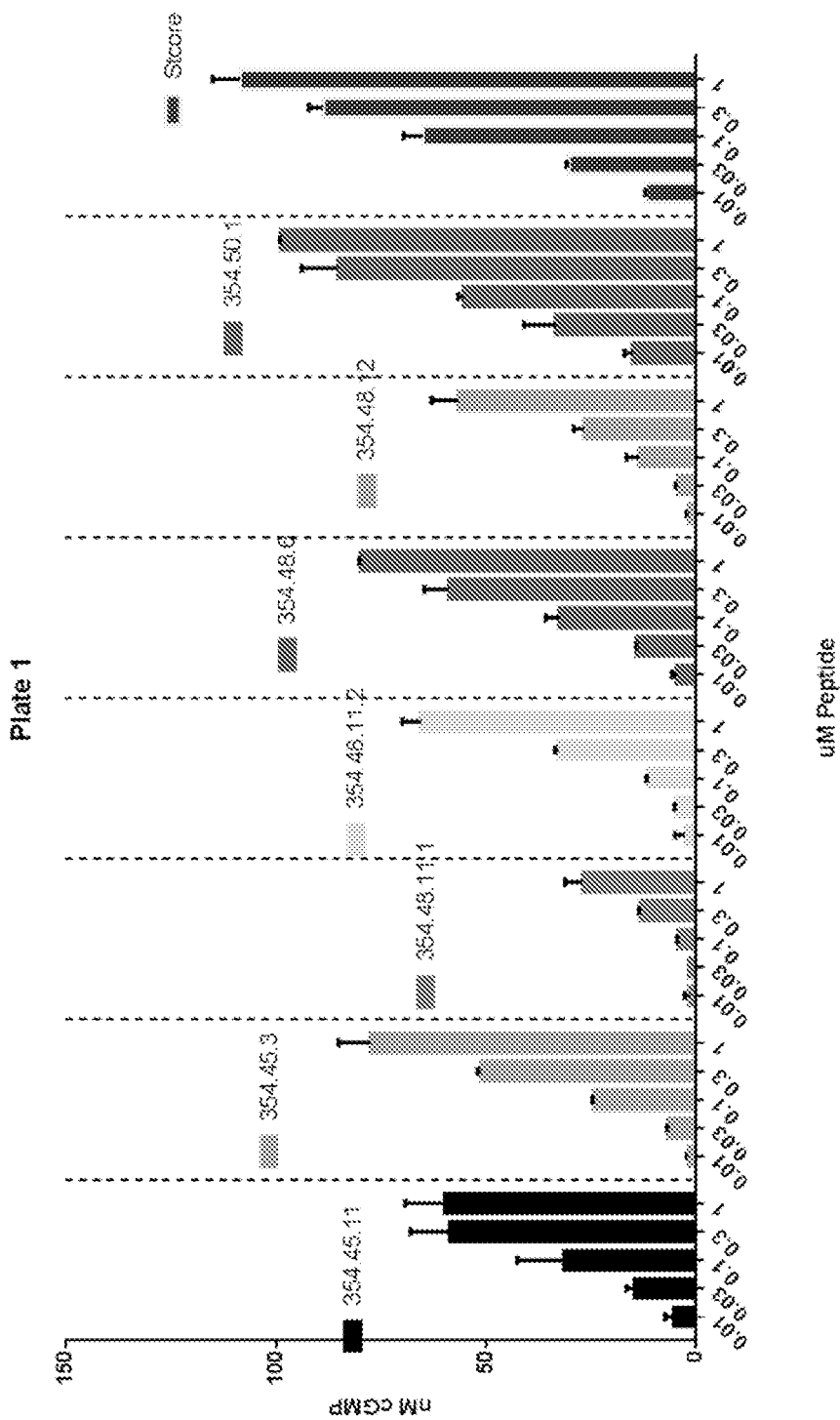
FIG. 13 illustrates the results of a cGMP accumulation in T84 cell assay for analysis of GC-C activity for SEQ ID NOs 54-59.
Figure 14:
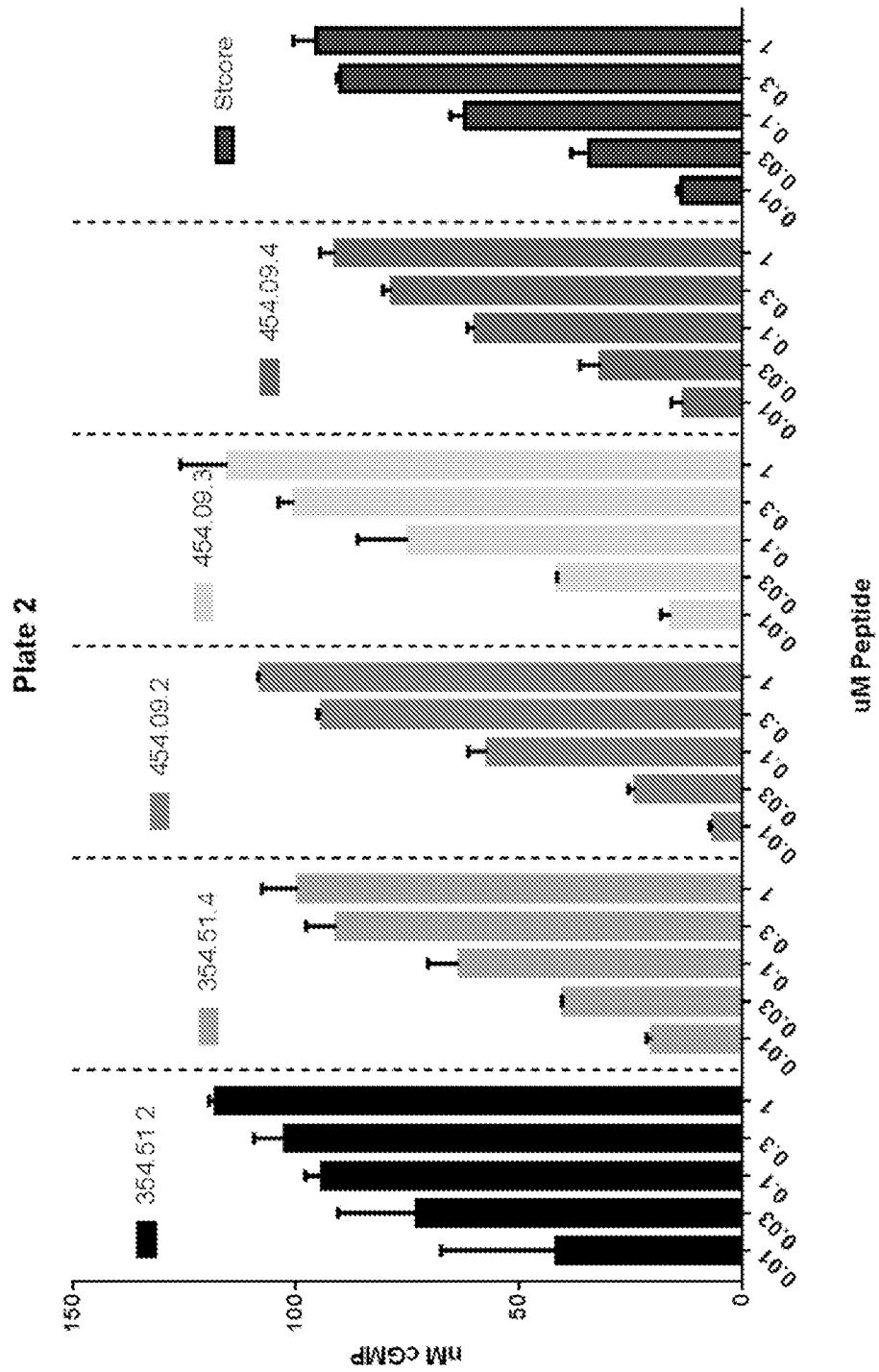
FIG. 14 illustrates the results of a cGMP accumulation in T84 cell assay for analysis of GC-C activity for SEQ ID NOs 60-64.

There was no peptide control used to determine endogenous levels of cGMP. Peptides were incubated for 30 minutes at 37° C. After 30 minutes, the supernatants were removed and the cells were lysed with 200 μL of 0.1 M HCl. The cells were lysed for 30 minutes on ice. After 30 minutes, lysates were pipetted off and placed into a 96 well HPLC plate and spun at 10,000×G for 10 minutes to remove any cell debris. Supernatants from the previous spin were removed and placed into a fresh 96 well HPLC plate. Samples were diluted with an equal volume of 1 M ammonium acetate (pH 7) to neutralize samples for better chromatography. A 2× cGMP standard curve was prepared in 0.1 M HCl and then diluted with an equal volume of 1 M ammonium acetate, with the following final concentrations in ng/mL: 1000, 500, 250, 125, 50, 25, 5, 2.5, 0.5. The ST Core peptide (hereinafter ST Core) has the amino acid sequence: Cys Cys Glu Leu Cys Cys Asn Pro Ala Cys Thr Gly Cys Tyr (SEQ ID NO:94).

cGMP concentrations were determined from each sample using the LC/MS conditions in Table 4 and a calculated standard curve. $EC_{50}$ values were calculated from concentration-response curves generated with GraphPad Prism Software. Results for selected peptides may be found in FIGS. 1-14, 23 and 24.

TABLE 1

| LC/MS Conditions: | | | | | | |
|---|---|---|---|---|---|---|
| MS: | Thermo Quantum or Vantage | | | | | |
| Ion Mode: | Electrospray, positive mode (ESI[+]) | | | | | |
| Scan Type: | Multiple reaction monitoring (MRM) | | | | | |
| Compound: | Transition | Dwell Time (msec) | Collision Energy (V) | Tube Lens | Retention Time (min) | LLOQ (ng/mL) |
| cGMP | 346 > 152 | 100 | 37 | 139 | 0.6 | 0.5 |
| (+3) cGMP | 349 > 155 | 100 | 37 | 139 | 0.6 | — |
| HPLC: | Waters Acquity UPLC | | | | | |
| Column: | Hypersil Gold C18, 2.1 × 50 mm, 1.9 um | | | | | |
| Guard Column: | Hypersil Gold, 2.1 × 10 mm, 5 um | | | | | |
| Flow Rate: | 750 uL/min | | | | | |

TABLE 1-continued

| LC/MS Conditions: | |
|---|---|
| Column Temp: | Room Temperature |
| Autosampler Temp: | 6° C. |
| Injection Volume: | 20 uL |
| Mobile Phases: | A = 0.1% formic acid in 100% Water |
| | B = 0.1% formic acid in 100% acetonitrile |

| Gradient: | Time (min) | % A | % B |
|---|---|---|---|
| | 0 | 100 | 0 |
| | 0.2 | 100 | 0 |
| | 0.3 | 50 | 50 |
| | 0.7 | 50 | 50 |
| | 0.8 | 100 | 0 |

Example 2

GC-C Binding Assay

All GC-C binding was done in a final volume of 200 μL of media at pH 5, 7 or 8. Media at pH 5 was prepared using DMEM and 0.5% BSA and 20 mM of 2-(N-morpholino)ethanesulfonic acid (MES). Media at pH 7 was prepared using DMEM and 0.5% BSA. Media at pH 8 was prepared using DMEM and 0.5% BSA with 20 mM of sodium bicarbonate.

T84 cells were used at a rate of 250,000 cells per reaction. The cells were grown to confluence on T-150 flasks using DMEM-F12 50/50 media and 5 mM L-glutamine and 5% FBS. Cells were scraped off using DMEM and 0.5% BSA and counted to determine how much volume to add to give 250,000 cells per reaction in a final volume of 200 μL. Then 200,000 CPM per reaction of I125-STp, cold peptide competitor and then T84 cells to start the reaction. Samples were then incubated at 37° C. for 1 hour. After 1 hour the entire sample was added to the pre-blocked GF-C plates and suctioned through. Then each well was washed twice with 200 μL of cold PBS. The bottom of the filter plate was removed and the 96 well plate was placed at 50 degrees to dry. After drying, 100 μL of scintillation fluid was added to each well and gently vortexed before counting. Results for selected peptides may be found in FIGS. 1 and 23.

Example 3

Rat Intestinal Fluid (RIF) in vitro Metabolism Incubations

Rat intestinal fluid was obtained by adding PBS to ligated rat jejunal loops for thirty minutes. The fluid was then collected, pooled and kept on ice before centrifugation at 4° C. The supernatant was removed and flash frozen. Then 60 μM of peptide (100 μg/mL) was added to rat intestinal fluid along with PBS and 0.5% BSA. The control incubations were performed in PBS. Then 50 μL aliquots from all samples were taken in duplicate at 0, 10, 30 and 60 minutes and stopped with 12% trichloroacetic acid containing internal standard.

Samples were spun and the supernatant was removed for analysis by LC-MS using the calculated accurate mass of each peptide (or predicted metabolites) to generate extracted ion chromatograms. The relative response factor (analyte peak area/internal standard peak area) for each sample was used to construct a percent remaining relative to time=0. Results for selected peptides may be found in FIGS. 1, 20, 21 and 23.

Example 4

In Vivo Ligated Rat Loops

First 60 μM of peptide was prepared in 200 μL of PBS. This solution was injected into ligated rat duodenal loops, which were approximately 3-5 cm in length. Three animals per peptide, per time point were used. At 30 minutes and 60 minutes the loops were excised, measured and weighed. Then the fluid was collected and flash frozen in Eppendorf tubes and the loops were re-weighed to determine their empty weight. Samples were then thawed and spun and the supernatant was removed from each sample. Then 50 μL aliquots were removed and added to 12% trichloroacetic acid containing an internal standard.

Figure 15:
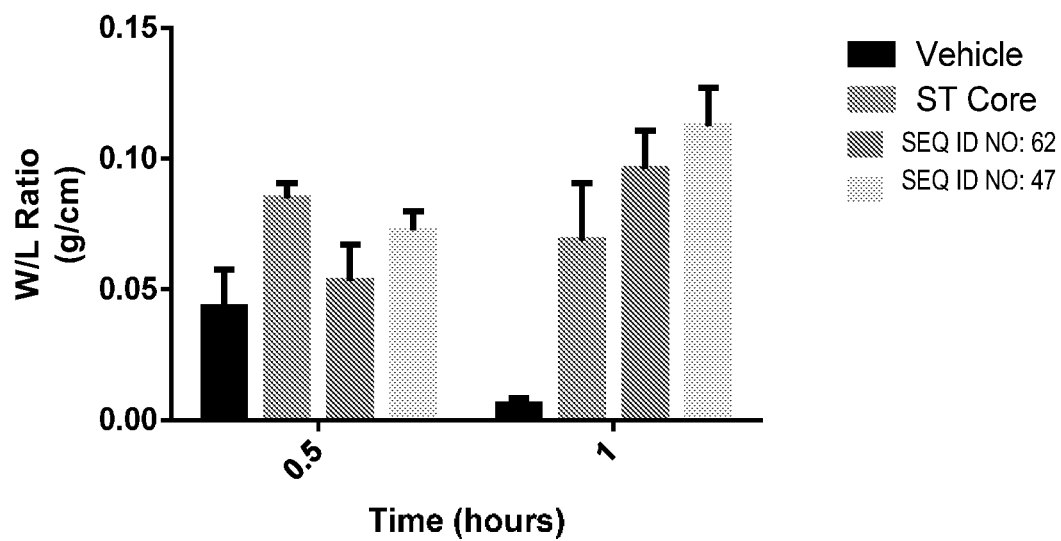
FIG. 15 illustrates the results of an in vivo rat duodenal loop assay for SEQ ID NOs 62 and 47.
Figure 16:
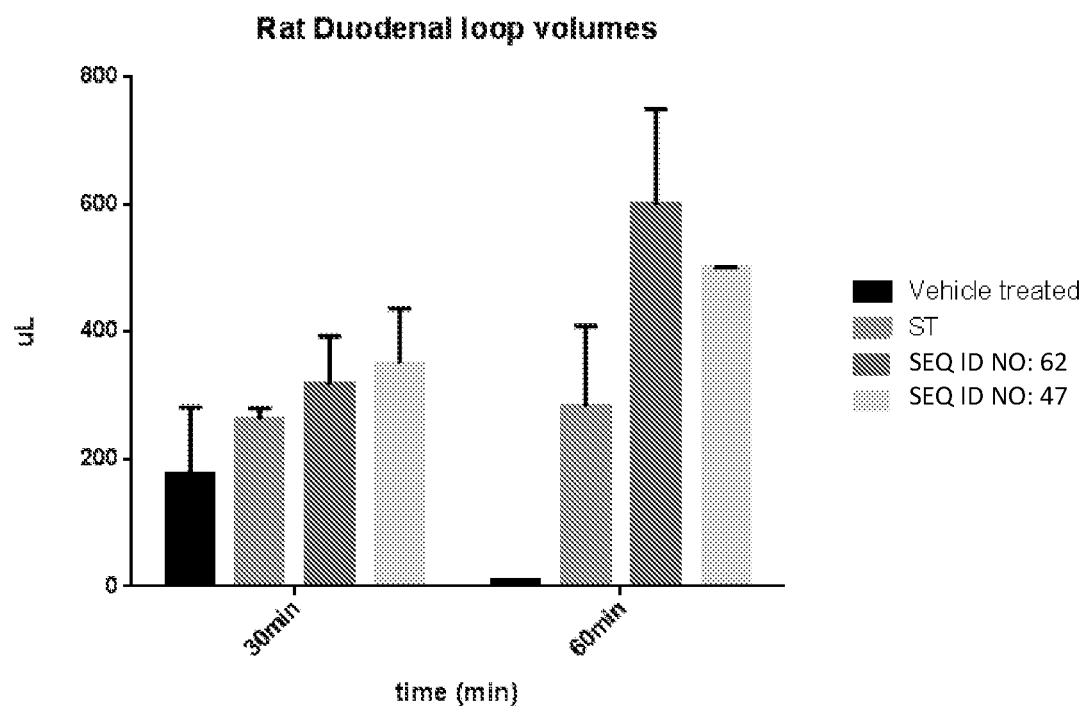
FIG. 16 illustrates the results of a rat duodenal loop volume test for SEQ ID NOs 62 and 47.
Figure 18:
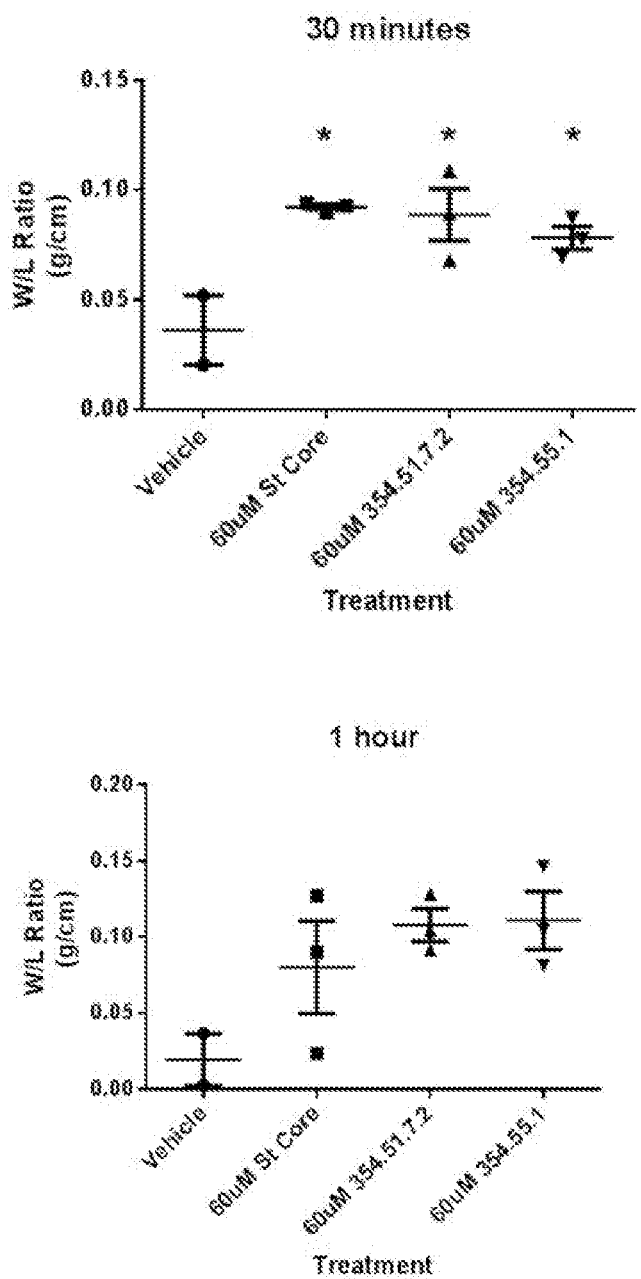
FIG. 18 illustrates the results of an in vivo ligated rat loop assay for SEQ ID NOs 67 and 69.
Figure 19:
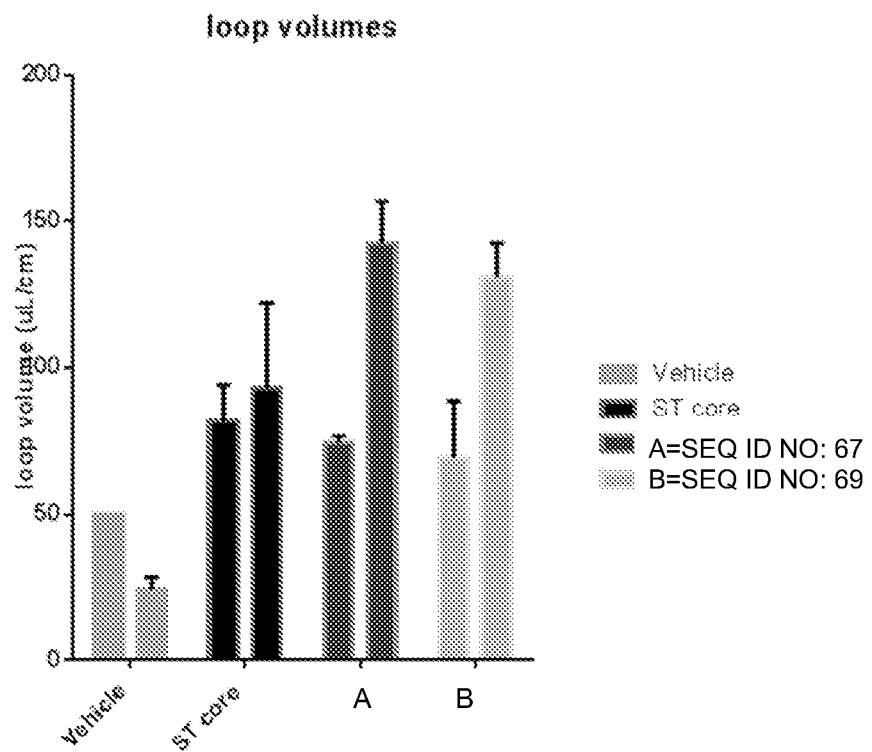
FIG. 19 illustrates the results of an in vivo ligated rat loop volume test for SEQ ID NOs 67 and 69.

Analysis was done by LC-MS using the calculated accurate mass of each peptide (or predicted metabolites) to generate extracted ion chromatograms. The relative response factor (analyte peak area/internal standard peak area) for each sample was used to construct a percent remaining relative to time=0. The amount of fluid secretion during the incubation was determined by the formula (fluid secretion=(loop full−loop empty)/length). This formula was used to calculate how much fluid was pulled into the loops at each time point. Results for selected peptides may be found in FIGS. 15, 16, 18, 19, 22 and 23.

Example 5

Preparation of Dicarba Peptides

Dicarba peptides were made using standard Fmoc-/Trt/Otbu protected amino acids. The dicarba peptides were synthesized on a Protein Technologies Symphony X® with the amino acids dissolved in dimethyl formamide (DMF) at a concentration of 0.5 M. The Fmoc-Cys(Trt)-OH was dissolved into a solution containing 0.5 M oxyma pure in DMF. Then HCTU was dissolved in NMP to 0.5 M, and a 1.0 M DIPEA in NMP was also used. DIC is dissolved in NMP to 0.5 M. Fmoc deprotection was performed using a solution containing 20% piperidine in DMF.

Fmoc-Cys(Trt)-O-Wang resin (0.2 mmol, 0.29 mmol/g) was treated with 20% piperidine in DMF (3×6 mL, 3 min, 1×6 mL, 10 min). The resulting resin was washed with DMF (6×10 mL, 30 s). A solution containing Fmoc-Xaa-OH, HCTU, and DIPEA in NMP that has been pre-mixed for 30 seconds was added and the mixture was agitated for 30 minutes. The resin was filtered and washed once with DMF. A second solution containing Fmoc-Xaa-OH, HCTU, and DIPEA in NMP that has been pre-mixed for 30 seconds was added and the mixture was agitated again for 30 minutes. In the case of Fmoc-Cys(Trt)-OH, the amino acid/oxyma solution was mixed with DIC in NMP for 5 min, added to the resin, and agitated for 45 min. The resin was filtered and washed once with DMF. The resulting resin was filtered and washed with DMF (6×10 mL). The material would be subjected to the aforementioned protocol and the peptide was elongated to the full sequence. To dry the resin before metathesis, the resin was washed with $CH_2Cl_2$ (3×10 mL) and hexanes (3×10 mL), and dried under diminished pressure overnight. The material was subjected to the aforementioned protocol and the peptide was elongated until macrocyclization.

To perform metathesis on the peptides, the following procedure was used. To 500 mg (0.1 mmol) of protected resin-bound peptide was added a 6 mg/mL solution of HGII in 5 mL of 4:1 1,2-dichloroethane-0.4 M LiCl in DMA. The resulting suspension was heated in a microwave with 200 W to 160° C. for 5 minutes. The suspension was cooled, filtered and washed with dichloromethane (3×10 mL) and NMP (3×10 mL). A small portion was cleaved to determine if the metathesis was complete. The resin was soaked in a 10% DMSO in NMP solution (10 mL) overnight to scavenge excess HGII catalyst. The resulting resin was washed with NMP (3×10 mL), and treated with 20% piperidine in DMF (3×15 mL, 10 min). The resin was washed with DMF (5×10 mL), $CH_2Cl_2$ (3×10 mL) and hexanes (3×10 mL), and dried under diminished pressure.

To cleave the peptide from the resin, the resin was treated with a solution containing 90:5:5 TFA-TIPS-$H_2O$ (20 mL). After 2 hours, the resin was filtered and washed with TFA (3 mL) and concentrated by 50%. Cold (−78° C.) ether was added to the solution (50 mL) and the resulting mixture was centrifuged @ 3500 rpm for 10 min. The ether was decanted and the solid was subjected to 2 additional washes and centrifuged with cold (−78° C.) ether. The resulting solid was dried under diminished pressure, dissolved into 1:1 $H_2O$-ACN, frozen and lyophilized.

The peptides were purified on a Waters Autopure® system using 0.1% TFA in water and 0.1% TFA in acetonitrile on a Waters PST C18 RP column (250×30 mm, 10 μ, 130 Å) at a flow rate of 40 mL/min. A linear gradient was used with 5-45% acetonitrile over 40 or 60 minutes. Fractions containing the desired product were pooled and oxidized.

To oxidize the cysteine residues for disulfide bond formation, the following procedure was used. To a solution containing 100 mL of 0.05 N $NH_4HCO_3$ (pH ~8) in 9:1 water-acetonitrile was added 5 mL of DMSO. After 72 hours, oxidation appeared complete by HPLC and the material was acidified with acetic acid, frozen and lyophilized. The peptides were purified on a Waters Autopure system using 0.1% TFA in Water and Acetonitrile on a Waters PST C18 RP column (250×30 mm, 10 μ, 130 A) at a flow rate of 40 mL/min. A linear gradient was used from 5-40% acetonitrile over 60 minutes. Fractions containing the desired product were pooled and lyophilized.

Example 6

Preparation of Cystathionine Containing Peptides

The material was synthesized on a Protein Technologies Symphony X® with amino acids dissolved in DMF at 0.5M. Fmoc-Cys(Trt)-OH was dissolved into a solution containing 0.5 M oxyma pure in DMF. HCTU was dissolved in NMP to 0.5 M, and a 1.0 M DIPEA in NMP was also used. DIC was dissolved in NMP to 0.5 M. Fmoc-deprotection was performed using a solution containing 20% piperidine in DMF.

To couple the peptide to the resin, Rink amide resin (0.2 mmol, 0.24 mmol/g) was treated with 20% piperidine in DMF (3×6 mL, 3 min, 1×6 mL, 10 min). The resulting resin was washed with DMF (6×10 mL, 30 s). A solution containing Fmoc-Xaa-OH, HCTU, and DIPEA in NMP that has been pre-mixed for 30 seconds was added and the mixture was agitated for 30 minutes. The resin was filtered and washed once with NMP. A second solution containing Fmoc-Xaa-OH, HCTU, and DIPEA in NMP that has been pre-mixed for 30 seconds was added and the mixture was agitated again for 30 minutes. In the case of Fmoc-Cys(Trt)-OH, the amino acid/oxyma pure solution was mixed with DIC in NMP for 5 minutes, added to the resin, and agitated for 45 min. The resin was filtered and washed once with DMF. The resulting resin was filtered and washed with DMF (6×10 mL). The material was subjected to the aforementioned protocol and the peptide was elongated until macrocyclization.

To couple the diamino acid, the resin was treated with 20% piperidine in DMF (3×6 mL, 3 min, 1×6 mL, 10 min). The resulting resin was washed with DMF (6×10 mL, 30 s). A solution containing alloc-HCys((Fmoc-Ala-OH)-3-yl)-all (227 mg, 0.4 mmol), PyAOP (209 mg 0.4 mmol) and DIPEA (139 μl, 125 mg, 0.8 mmol) in 5 mL of NMP was added to the resin. After 90 min, the resin was filtered and washed with DMF (6×10 mL). The peptide was then elongated using the aforementioned protocol.

To perform Allyl-Alloc deprotection, the resin (0.2 mmol) was suspended in 10 mL of DMF and a solution containing Pd(PPh3)4 (300 mg, 0.26 mmol) in 10 mL of CH2Cl2 was added followed by 0.25 mL (2 mmol) of phenyl silane. The resulting mixture was shaken in the absence of light for 2 hours. A small sample was cleaved to ensure complete deprotection. The resulting resin was filtered and washed with CH2Cl2 (3×10 mL) and DMF (3×10 mL). The resin was treated with a solution containing 0.5% sodium diethyldithiocarbamate in DMF (10 mL, 4×15 min), and washed with DMF (3×10 mL).

To perform macrocyclization, the resin was treated with a 20% piperidine in DMF solution (2×5 min, 1×10 min, 15 mL) and washed with DMF (6×15 mL). A solution containing 521 mg (1 mmol) of PyAOP in 15 mL of DMF was added and after 1 minute, 0.35 mL (2 mmol) of DIPEA was added and shaken for 60 minutes. A small sample was taken for analysis. The resulting resin was washed with DMF (3×15 mL) and placed back onto the Symphony X to complete the synthesis.

To cleave the peptide from the resin, the resin was treated with a solution containing 90:5:3:2 TFA-TIPS-DODT-$H_2O$ (20 mL). After 2 hours, the resin was filtered and washed with TFA (3 mL) and concentrated by 50%. Cold (−78° C.) ether was added to the solution (50 mL) and the resulting mixture was centrifuged @ 3500 rpm for 10 minutes. The ether was decanted and the solid was subject to 2 additional washes and centrifuged with cold (−78° C.) ether. The resulting solid was dried under diminished pressure, dissolved into 1:1 H2O-ACN, frozen and lyophilized. The peptides were then purified on a Waters autopure system using 0.1% TFA in water and 0.1% TFA in acetonitrile on a Waters PST C18 RP column (250×30 mm, 10 μ, 130 A) at a flow rate of 40 mL/min. A linear gradient was used 5-45% acetonitrile over 40 or 60 minutes. Fractions containing the desired product were pooled and oxidized.

Oxidation was performed adding 5 mL of DMSO to a solution containing 100 mL of 0.05 N NH$_4$HCO$_3$ (pH ~8) in 9:1 water-acetonitrile. After 72 hours, oxidation appeared complete by HPLC and the material was acidified with acetic acid, frozen and lyophilized. The peptides were purified on a Waters Autopure® system using 0.1% TFA in water and 0.1% TFA in acetonitrile on a Waters PST C18 RP column (250×30 mm, 10 μ, 130 Å) at a flow rate of 40 mL/min. A linear gradient was used from 5-40% acetonitrile over 60 minutes. Fractions containing the desired product were pooled and lyophilized.

Example 7

Production of Lactam Bond Containing Peptides

Peptides were synthesized using standard Fmoc-/Trt/Otbu protected amino acids. Material was synthesized on a Protein Technologies Symphony X® with amino acids dissolved in DMF at 0.5M. Fmoc-Cys(Trt)-OH was dissolved into a solution containing 0.5 M oxyma pure in DMF. HCTU was dissolved NMP to 0.5 M, and a 1.0 M DIEA in NMP was also used. DIC was dissolved in NMP to 0.5 M. Fmoc-deprotection was performed using a solution containing 20% piperidine in DMF. Uncommon amino acids were coupled manually as described below.

To incorporate Fmoc-Dpr(ivDde)-OH, a solution containing 533 mg (1.0 mmol) of Fmoc-Dpr(ivDde)-OH, 521 mg (1.0 mmol) of PyAOP and 348 μL (258 mg, 2.0 mmol) of DIPEA in 6 mL of DMF was added to the deprotected resin (0.2 mmol). After 90 min, the resin was filtered and washed with DMF (3×10 mL), CH$_2$Cl$_2$ (3×10 mL) and again with DMF (3×10 mL). The resin was placed back onto the synthesizer to continue the synthesis.

To incorporate Fmoc-Asp(ODmab)-OH, a solution containing 667 mg (1.0 mmol) of Fmoc-Asp(Odmab)-OH, 521 mg (1.0 mmol) of PyAOP and 348 μL (258 mg, 2.0 mmol) of DIPEA in 6 mL of DMF was added to the deprotected resin (0.2 mmol). After 90 min, the resin was filtered and washed with DMF (3×10 mL), CH$_2$Cl$_2$ (3×10 mL) and again with DMF (3×10 mL). The resin was placed back onto the synthesizer for final deprotection.

To Boc protect the N-terminus, the resin was treated with 218 mg (1.0 mmol) di-tert-butyl dicarbonate in 5 mL of DMF. After 4 h, a small sample (~10 mg) was removed and acetylated with 10 μL of acetic anhydride and 30 μL of DIPEA in DMF to check for completion. The resulting resin was washed with DMF (5×10 mL) and treated with 100 μL of acetic anhydride and 300 μL of DIPEA in DMF for 50 min. the resulting resin was washed with DMF (6×10 mL)

To remove ivDDE and Dmab, the protected resin was treated with a solution containing 2% hydrazine monohydrate in DMF (5×5 mL, 5 min). The resulting resin was washed with DMF (6×10 ml).

To form the lactam, the resin was treated with 521 mg (1.0 mmol) of PyAOP and 348 μL (258 mg, 2.0 mmol) of DIPEA in 5 mL of DMF. The resulting mixture was heated via microwave heating (200 W) to 100° C. for 10 min. The resulting resin was cooled, filtered and washed with DMF (6×10 mL) and CH$_2$Cl$_2$ (6×10 mL) and dried under diminished pressure.

To cleave the peptide from the resin, the resin was treated with a solution containing 90:5:3:2 TFA-TIPS-DODT-H2O (20 mL). After 2 h, the resin was filtered and washed with TFA (3 mL) and concentrated by 50%. Cold (−78° C.) either was added to the solution (50 mL) and the resulting mixture was centrifuged @ 3500 rpm for 10 min. The ether was decanted and the solid was subject to 2 addition washes/centrifuge with cold (−78° C.) ether. The resulting solid was dried under diminished pressure, dissolved into 1:1 H2O-ACN, frozen and lyophilized.

To oxidize the peptide, the crude peptide (280 mg) was dissolved in water and the mixture was treated with solid NH$_4$HCO$_3$ to adjust the pH to be >7. Afterwhich 20 mL of acetonitrile was added followed by 10 mL of DMSO. After 24 h, oxidation appeared complete by HPLC and the material was acidified to pH ~2 with trifluoroacetic acid, filtered, frozen and lyophilized.

The peptide was purified on a Waters Autopure® system using 0.1% TFA in water and 0.1% TFA in acetonitrile was used on a Waters PST C18 RP column (250×30 mm, 5 μ, 130 Å) at a flow rate of 40 mL/min. A linear gradient from 5% 0.1% TFA in acetonitrile to 25% 0.1% TFA in acetonitrile over 40 min was used Fractions containing desired product were pooled, frozen and lyophilized. The material was subjected to a second pass purification.

The peptide was purified on a Waters Autopure® system using 0.1% TFA in water and 0.1% TFA in acetonitrile was used on a Waters PST C18 RP column (250×19 mm, 5 u, 130 Å) at a flow rate of 20 mL/min. A linear gradient from 15% 0.1% TFA in acetonitrile to 25% 0.1% TFA in acetonitrile over 60 min was used. Fractions containing desired product were pooled, frozen and lyophilized to give a colorless solid.

Example 8

Gastrointestinal Transit in Mice

The purpose of the assay was to test the effect of the guanylate cyclase C agonist peptides on in vivo gastrointestinal transit in mice. Orally-dosed guanylate cyclase C agonists have been demonstrated to increase the % Distance Travelled by a charcoal meal in mice.

For the assay, female CD-1 mice (n=10 per group) weighing 25-30 g were fasted overnight and given access to water ad libitum. Activated charcoal (20 g; 100 mesh; Sigma cat# 242276) was suspended in 200 mL gum arabic (100 mg/mL), and stirred for at least one hour. Test peptides were prepared in a 20 mM Tris pH 6.9 vehicle.

Figure 25:
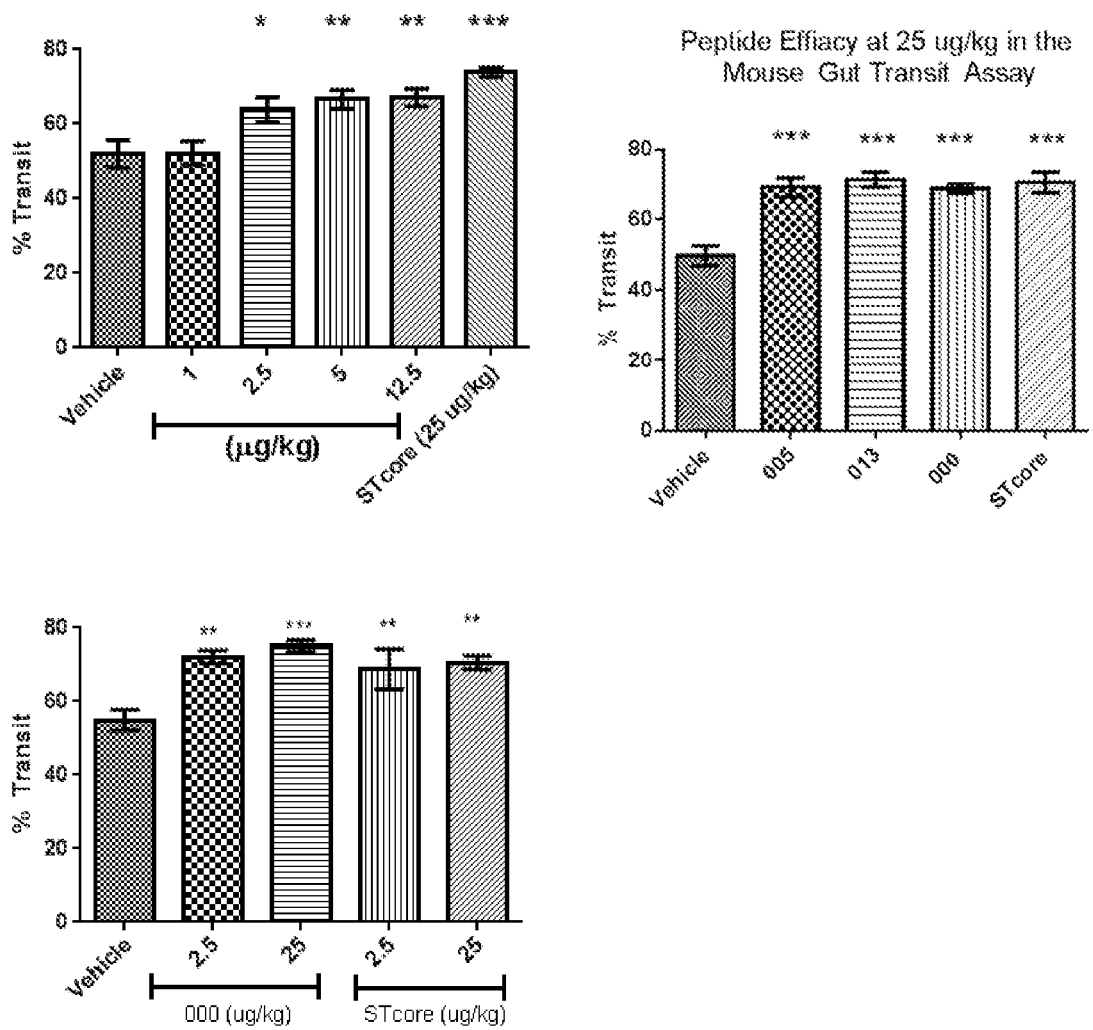
FIG. 25 illustrates the results of a mouse gut transit assay for SEQ ID NOs 2, 7 and 11.

Test peptide and vehicle were administered in 200 μL doses by oral gavage. Seven minutes after dosing the test peptides, 200 μL of the charcoal/gum arabic suspension was dosed by oral gavage. After 15 minutes, mice were sacrificed by CO$_2$ overdose. The gastrointestinal tract was removed from the esophagus to the caecum. The total length of the small intestine was measured from the pyloric junction to the ileocaecal junction. The distance travelled by the charcoal was measured from the pyloric junction to the charcoal front. The Distance Travelled (%) was determined as (distance travelled by charcoal/total length of the small intestine)×100. Data were entered into the GraphPad Prism software program and analyzed by ANOVA using a Bonferroni multiple comparison test post-hoc. Plots of data and ED$_{50}$ were also determined using the GraphPad Prism software package. Results for selected peptides may be found in FIGS. 17, 25, 26, and 27.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

```
                              SEQUENCE LISTING

<160> NUMBER OF SEQ ID NOS: 94

<210> SEQ ID NO 1
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is glutamic acid wherein the side chain
      carboxylic acid forms the peptide linkage or is absent
<220> FEATURE:
<221> NAME/KEY: VARIANT
<222> LOCATION: (2)..(2)
<223> OTHER INFORMATION: Xaa2 is lysine wherein the side chain amine
      forms the peptide linkage, Asn or is absent
<220> FEATURE:
<221> NAME/KEY: VARIANT
<222> LOCATION: (3)..(3)
<223> OTHER INFORMATION: Xaa3 is Asn, Ser or is absent
<220> FEATURE:
<221> NAME/KEY: VARIANT
<222> LOCATION: (4)..(4)
<223> OTHER INFORMATION: Xaa4 is Ser or is absent
<220> FEATURE:
<221> NAME/KEY: VARIANT
<222> LOCATION: (5)..(5)
<223> OTHER INFORMATION: Xaa5 is Ser, Asn, Ile, glutamic acid wherein
      the side chain carboxylic acid forms the peptide linkage or is
      absent
<220> FEATURE:
<221> NAME/KEY: VARIANT
<222> LOCATION: (6)..(6)
<223> OTHER INFORMATION: Xaa6 is Tyr, Asp, 4-fluorophenylalanine
      ((4-F)Phe), lysine wherein the side chain amine forms the peptide
      linkage or is absent
<220> FEATURE:
<221> NAME/KEY: VARIANT
<222> LOCATION: (7)..(7)
<223> OTHER INFORMATION: Xaa7 is Cys, cystathionine (Cth), allylglycine
      (Ag), allylglycine with a reduced dicarba bond (Hag), or Asp
<220> FEATURE:
<221> NAME/KEY: MISC_FEATURE
<222> LOCATION: (7)..(12)
<223> OTHER INFORMATION: covalent bond between Xaa7 and Xaa12
<220> FEATURE:
<221> NAME/KEY: VARIANT
<222> LOCATION: (8)..(8)
<223> OTHER INFORMATION: Xaa8 is Cys, cystathionine (Cth), penicillamine
      (Pen), or allylglycine (Ag)
<220> FEATURE:
<221> NAME/KEY: MISC_FEATURE
<222> LOCATION: (8)..(16)
<223> OTHER INFORMATION: covalent bond between Xaa8 and Xaa16
<220> FEATURE:
<221> NAME/KEY: VARIANT
<222> LOCATION: (9)..(9)
<223> OTHER INFORMATION: Xaa9 is Glu, Asp, Ser, Thr, or Gln
<220> FEATURE:
<221> NAME/KEY: VARIANT
<222> LOCATION: (10)..(10)
<223> OTHER INFORMATION: Xaa10 is Leu, cyclohexylalanine (Cha), Phe, or
      4-fluorophenylalanine ((4-F)Phe)
<220> FEATURE:
<221> NAME/KEY: VARIANT
<222> LOCATION: (11)..(11)
<223> OTHER INFORMATION: Xaa11 is Cys, allylglycine (Ag), or
      penicillamine (Pen)
```

```
<220> FEATURE:
<221> NAME/KEY: MISC_FEATURE
<222> LOCATION: (11)..(19)
<223> OTHER INFORMATION: covalent bond between Xaa11 and Xaa19
<220> FEATURE:
<221> NAME/KEY: VARIANT
<222> LOCATION: (12)..(12)
<223> OTHER INFORMATION: Xaa12 is Cys, allylglycine (Ag), allylglycine
      with a reduced dicarba bond (Hag), cystathionine (Cth),
      di-aminopropionic acid (Dpr), or Val
<220> FEATURE:
<221> NAME/KEY: VARIANT
<222> LOCATION: (13)..(13)
<223> OTHER INFORMATION: Xaa13 is Asn or Leu
<220> FEATURE:
<221> NAME/KEY: VARIANT
<222> LOCATION: (14)..(14)
<223> OTHER INFORMATION: Xaa14 is Pro, Val, sarcosine (Sar), Leu, or
      Hydroxyproline (OH-Pro)
<220> FEATURE:
<221> NAME/KEY: VARIANT
<222> LOCATION: (16)..(16)
<223> OTHER INFORMATION: Xaa16 is Cys, allylglycine (Ag), penicillamine
      (Pen) or cystathionine (Cth)
<220> FEATURE:
<221> NAME/KEY: VARIANT
<222> LOCATION: (17)..(17)
<223> OTHER INFORMATION: Xaa17 is Tyr, Thr, cyclohexylalanine (Cha),
      4-fluorophenylalanine ((4-F)Phe), Phe, Ser, or Ala
<220> FEATURE:
<221> NAME/KEY: VARIANT
<222> LOCATION: (19)..(19)
<223> OTHER INFORMATION: Xaa19 is Cys, Ag or Pen
<220> FEATURE:
<221> NAME/KEY: VARIANT
<222> LOCATION: (20)..(20)
<223> OTHER INFORMATION: Xaa20 is Tyr, Leu, 4-fluorophenylalanine
      ((4-F)Phe), cyclohexylalanine (Cha), D-Tyr, N-Methyl Tyr (Nme-Tyr)
      or is absent
<220> FEATURE:
<221> NAME/KEY: VARIANT
<222> LOCATION: (21)..(21)
<223> OTHER INFORMATION: Xaa21 is absent or Asn

<400> SEQUENCE: 1

Xaa Xaa Xaa Xaa Xaa Xaa Xaa Xaa Xaa Xaa Xaa Xaa Xaa Xaa Ala Xaa
1               5                   10                  15

Xaa Gly Xaa Xaa Xaa
            20

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 2

Gly Cys Glu Leu Cys Gly Asn Pro Ala Cys Thr Gly Cys Tyr
1               5                   10

<210> SEQ ID NO 3
```

```
<211> LENGTH: 20
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with C12 alkyl carboxylic
      acid
<220> FEATURE:
<221> NAME/KEY: MOD_RES
<222> LOCATION: (1)..(1)
<223> OTHER INFORMATION: glutamic acid wherein the side chain carboxylic
      acid forms the peptide linkage
<220> FEATURE:
<221> NAME/KEY: MOD_RES
<222> LOCATION: (2)..(2)
<223> OTHER INFORMATION: lysine wherein the side chain amine forms the
      peptide linkage
<220> FEATURE:
<221> NAME/KEY: MOD_RES
<222> LOCATION: (20)..(20)
<223> OTHER INFORMATION: AMIDATION

<400> SEQUENCE: 3

Glu Lys Asn Ser Ser Tyr Cys Cys Glu Leu Cys Cys Asn Pro Ala Cys
1               5                   10                  15

Thr Gly Cys Tyr
            20

<210> SEQ ID NO 4
<211> LENGTH: 20
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with C16 alkyl carboxylic
      acid
<220> FEATURE:
<221> NAME/KEY: MOD_RES
<222> LOCATION: (1)..(1)
<223> OTHER INFORMATION: glutamic acid wherein the side chain carboxylic
      acid forms the peptide linkage
<220> FEATURE:
<221> NAME/KEY: MOD_RES
<222> LOCATION: (2)..(2)
<223> OTHER INFORMATION: lysine wherein the side chain amine forms the
      peptide linkage
<220> FEATURE:
<221> NAME/KEY: MOD_RES
<222> LOCATION: (20)..(20)
<223> OTHER INFORMATION: AMIDATION

<400> SEQUENCE: 4

Glu Lys Asn Ser Ser Tyr Cys Cys Glu Leu Cys Cys Asn Pro Ala Cys
1               5                   10                  15

Thr Gly Cys Tyr
            20

<210> SEQ ID NO 5
<211> LENGTH: 20
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with C12 alkyl carboxylic
```

```
            acid
<220> FEATURE:
<221> NAME/KEY: MOD_RES
<222> LOCATION: (1)..(1)
<223> OTHER INFORMATION: glutamic acid wherein the side chain carboxylic
      acid forms the peptide linkage
<220> FEATURE:
<221> NAME/KEY: MOD_RES
<222> LOCATION: (2)..(2)
<223> OTHER INFORMATION: lysine wherein the side chain amine forms the
      peptide linkage

<400> SEQUENCE: 5

Glu Lys Asn Ser Ser Tyr Cys Cys Glu Leu Cys Cys Asn Pro Ala Cys
1               5                   10                  15

Thr Gly Cys Tyr
            20

<210> SEQ ID NO 6
<211> LENGTH: 20
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with C14 alkyl carboxylic
      acid
<220> FEATURE:
<221> NAME/KEY: MOD_RES
<222> LOCATION: (1)..(1)
<223> OTHER INFORMATION: glutamic acid wherein the side chain carboxylic
      acid forms the peptide linkage
<220> FEATURE:
<221> NAME/KEY: MOD_RES
<222> LOCATION: (2)..(2)
<223> OTHER INFORMATION: lysine wherein the side chain amine forms the
      peptide linkage

<400> SEQUENCE: 6

Glu Lys Asn Ser Ser Tyr Cys Cys Glu Leu Cys Cys Asn Pro Ala Cys
1               5                   10                  15

Thr Gly Cys Tyr
            20

<210> SEQ ID NO 7
<211> LENGTH: 20
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with C16 alkyl carboxylic
      acid
<220> FEATURE:
<221> NAME/KEY: MOD_RES
<222> LOCATION: (1)..(1)
<223> OTHER INFORMATION: glutamic acid wherein the side chain carboxylic
      acid forms the peptide linkage
<220> FEATURE:
<221> NAME/KEY: MOD_RES
<222> LOCATION: (2)..(2)
<223> OTHER INFORMATION: lysine wherein the side chain amine forms the
      peptide linkage

<400> SEQUENCE: 7

Glu Lys Asn Ser Ser Tyr Cys Cys Glu Leu Cys Cys Asn Pro Ala Cys
1               5                   10                  15
```

Thr Gly Cys Tyr
            20

<210> SEQ ID NO 8
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (2)..(2)
<223> OTHER INFORMATION: allylglycine
<220> FEATURE:
<221> NAME/KEY: MOD_RES
<222> LOCATION: (10)..(10)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 8

Cys Gly Glu Leu Cys Cys Asn Pro Ala Gly Thr Gly Cys Tyr
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (4)..(4)
<223> OTHER INFORMATION: allylglycine
<220> FEATURE:
<221> NAME/KEY: MOD_RES
<222> LOCATION: (12)..(12)
<223> OTHER INFORMATION: allylglycine
<220> FEATURE:
<221> NAME/KEY: MOD_RES
<222> LOCATION: (16)..(16)
<223> OTHER INFORMATION: AMIDATION

<400> SEQUENCE: 9

Asn Asp Asp Gly Glu Leu Cys Val Asn Val Ala Gly Thr Gly Cys Leu
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (7)..(7)
<223> OTHER INFORMATION: allylglycine
<220> FEATURE:
<221> NAME/KEY: MOD_RES
<222> LOCATION: (15)..(15)
<223> OTHER INFORMATION: allylglycine
<220> FEATURE:
<221> NAME/KEY: MOD_RES
<222> LOCATION: (16)..(16)
<223> OTHER INFORMATION: AMIDATION

<400> SEQUENCE: 10

Asn Asp Asp Cys Glu Leu Gly Val Asn Val Ala Cys Thr Gly Gly Leu
1               5                   10                  15

```
<210> SEQ ID NO 11
<211> LENGTH: 20
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with C18 alkyl carboxylic
      acid
<220> FEATURE:
<221> NAME/KEY: MOD_RES
<222> LOCATION: (1)..(1)
<223> OTHER INFORMATION: glutamic acid wherein the side chain carboxylic
      acid forms the peptide linkage
<220> FEATURE:
<221> NAME/KEY: MOD_RES
<222> LOCATION: (2)..(2)
<223> OTHER INFORMATION: lysine wherein the side chain amine forms the
      peptide linkage

<400> SEQUENCE: 11

Glu Lys Asn Ser Ser Tyr Cys Cys Glu Leu Cys Asn Pro Ala Cys
1               5                   10                  15

Thr Gly Cys Tyr
            20

<210> SEQ ID NO 12
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (13)..(13)
<223> OTHER INFORMATION: AMIDATION

<400> SEQUENCE: 12

Gly Cys Glu Leu Cys Gly Asn Pro Ala Cys Thr Gly Cys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (13)..(13)
<223> OTHER INFORMATION: AMIDATION

<400> SEQUENCE: 13

Gly Cys Glu Leu Cys Gly Asn Pro Ala Cys Ala Gly Cys
1               5                   10
```

```
<210> SEQ ID NO 14
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 14

Gly Cys Glu Phe Cys Gly Asn Pro Ala Cys Thr Gly Cys Tyr
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (4)..(4)
<223> OTHER INFORMATION: 4-fluorophenylalanine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (13)..(13)
<223> OTHER INFORMATION: AMIDATION

<400> SEQUENCE: 15

Gly Cys Glu Phe Cys Gly Asn Pro Ala Cys Thr Gly Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (4)..(4)
<223> OTHER INFORMATION: 4-fluorophenylalanine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION
```

```
<400> SEQUENCE: 16

Gly Cys Glu Phe Cys Gly Asn Pro Ala Cys Thr Gly Cys Tyr
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (4)..(4)
<223> OTHER INFORMATION: 4-fluorophenylalanine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: 4-fluorophenylalanine
<220> FEATURE:
<221> NAME/KEY: MOD_RES
<222> LOCATION: (14)..(14)
<223> OTHER INFORMATION: AMIDATION

<400> SEQUENCE: 17

Gly Cys Glu Phe Cys Gly Asn Pro Ala Cys Thr Gly Cys Phe
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (5)..(5)
<223> OTHER INFORMATION: allylglycine
<220> FEATURE:
<221> NAME/KEY: MOD_RES
<222> LOCATION: (13)..(13)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 18

Cys Cys Glu Leu Gly Cys Asn Pro Ala Cys Thr Gly Gly Tyr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
```

```
<221> NAME/KEY: MOD_RES
<222> LOCATION: (13)..(13)
<223> OTHER INFORMATION: AMIDATION

<400> SEQUENCE: 19

Gly Cys Glu Phe Cys Gly Asn Pro Ala Cys Thr Gly Cys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: 4-fluorophenylalanine
<220> FEATURE:
<221> NAME/KEY: MOD_RES
<222> LOCATION: (14)..(14)
<223> OTHER INFORMATION: AMIDATION

<400> SEQUENCE: 20

Gly Cys Glu Phe Cys Gly Asn Pro Ala Cys Thr Gly Cys Phe
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (4)..(4)
<223> OTHER INFORMATION: 4-fluorophenylalanine
<220> FEATURE:
<221> NAME/KEY: MOD_RES
<222> LOCATION: (14)..(14)
<223> OTHER INFORMATION: AMIDATION

<400> SEQUENCE: 21

Cys Cys Glu Phe Cys Cys Asn Pro Ala Cys Thr Gly Cys Tyr
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (4)..(4)
<223> OTHER INFORMATION: 4-fluorophenylalanine
<220> FEATURE:
<221> NAME/KEY: MOD_RES
<222> LOCATION: (14)..(14)
<223> OTHER INFORMATION: 4-fluorophenylalanine
<220> FEATURE:
<221> NAME/KEY: MOD_RES
<222> LOCATION: (14)..(14)
<223> OTHER INFORMATION: AMIDATION
```

```
<400> SEQUENCE: 22

Cys Cys Glu Phe Cys Cys Asn Pro Ala Cys Thr Gly Cys Phe
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: 4-fluorophenylalanine
<220> FEATURE:
<221> NAME/KEY: MOD_RES
<222> LOCATION: (14)..(14)
<223> OTHER INFORMATION: AMIDATION

<400> SEQUENCE: 23

Gly Cys Glu Leu Cys Gly Asn Pro Ala Cys Thr Gly Cys Phe
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: 4-fluorophenylalanine
<220> FEATURE:
<221> NAME/KEY: MOD_RES
<222> LOCATION: (2)..(2)
<223> OTHER INFORMATION: allylglycine
<220> FEATURE:
<221> NAME/KEY: MOD_RES
<222> LOCATION: (7)..(7)
<223> OTHER INFORMATION: allylglycine
<220> FEATURE:
<221> NAME/KEY: MOD_RES
<222> LOCATION: (15)..(15)
<223> OTHER INFORMATION: 4-fluorophenylalanine
<220> FEATURE:
<221> NAME/KEY: MOD_RES
<222> LOCATION: (15)..(15)
<223> OTHER INFORMATION: AMIDATION

<400> SEQUENCE: 24

Phe Gly Cys Glu Leu Cys Gly Asn Pro Ala Cys Thr Gly Cys Phe
1               5                   10                  15

<210> SEQ ID NO 25
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
```

```
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 25

Gly Cys Glu Leu Cys Gly Asn Pro Ala Cys Ala Gly Cys Tyr
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 26

Gly Cys Glu Leu Cys Gly Asn Pro Ala Cys Tyr Gly Cys Tyr
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 27

Gly Cys Glu Leu Cys Gly Asn Pro Ala Cys Phe Gly Cys Tyr
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
```

```
<221> NAME/KEY: MOD_RES
<222> LOCATION: (11)..(11)
<223> OTHER INFORMATION: 4-fluorophenylalanine
<220> FEATURE:
<221> NAME/KEY: MOD_RES
<222> LOCATION: (14)..(14)
<223> OTHER INFORMATION: AMIDATION

<400> SEQUENCE: 28

Gly Cys Glu Leu Cys Gly Asn Pro Ala Cys Phe Gly Cys Tyr
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 29

Gly Cys Glu Leu Cys Gly Asn Pro Ala Cys Thr Gly Cys Leu
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: cyclohexylalanine
<220> FEATURE:
<221> NAME/KEY: MOD_RES
<222> LOCATION: (14)..(14)
<223> OTHER INFORMATION: AMIDATION

<400> SEQUENCE: 30

Gly Cys Glu Leu Cys Gly Asn Pro Ala Cys Thr Gly Cys Ala
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
```

```
<221> NAME/KEY: MOD_RES
<222> LOCATION: (4)..(4)
<223> OTHER INFORMATION: cyclohexylalanine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 31

Gly Cys Glu Ala Cys Gly Asn Pro Ala Cys Thr Gly Cys Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: D-Tyr
<220> FEATURE:
<221> NAME/KEY: MOD_RES
<222> LOCATION: (14)..(14)
<223> OTHER INFORMATION: AMIDATION

<400> SEQUENCE: 32

Gly Cys Glu Leu Cys Gly Asn Pro Ala Cys Thr Gly Cys Tyr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: VARIANT
<222> LOCATION: (2)..(2)
<223> OTHER INFORMATION: penicillamine
<220> FEATURE:
<221> NAME/KEY: MOD_RES
<222> LOCATION: (6)..(6)
<223> OTHER INFORMATION: allylglycine
<220> FEATURE:
<221> NAME/KEY: VARIANT
<222> LOCATION: (10)..(10)
<223> OTHER INFORMATION: penicillamine
<220> FEATURE:
<221> NAME/KEY: MOD_RES
<222> LOCATION: (14)..(14)
<223> OTHER INFORMATION: AMIDATION

<400> SEQUENCE: 33

Gly Xaa Glu Leu Cys Gly Asn Pro Ala Xaa Thr Gly Cys Tyr
1               5                   10
```

```
<210> SEQ ID NO 34
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (15)..(15)
<223> OTHER INFORMATION: AMIDATION

<400> SEQUENCE: 34

Gly Cys Glu Leu Cys Gly Asn Pro Ala Cys Thr Gly Cys Leu Asn
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (15)..(15)
<223> OTHER INFORMATION: AMIDATION

<400> SEQUENCE: 35

Gly Cys Glu Leu Cys Gly Asn Pro Ala Cys Thr Gly Cys Tyr Asn
1               5                   10                  15

<210> SEQ ID NO 36
<211> LENGTH: 15
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (2)..(2)
<223> OTHER INFORMATION: allylglycine
<220> FEATURE:
<221> NAME/KEY: MOD_RES
<222> LOCATION: (7)..(7)
<223> OTHER INFORMATION: allylglycine
<220> FEATURE:
<221> NAME/KEY: MOD_RES
<222> LOCATION: (15)..(15)
<223> OTHER INFORMATION: AMIDATION

<400> SEQUENCE: 36

Asp Gly Cys Glu Leu Cys Gly Asn Pro Ala Cys Thr Gly Cys Tyr
1               5                   10                  15

<210> SEQ ID NO 37
<211> LENGTH: 16
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (3)..(3)
<223> OTHER INFORMATION: allylglycine
<220> FEATURE:
<221> NAME/KEY: MOD_RES
<222> LOCATION: (8)..(8)
<223> OTHER INFORMATION: allylglycine
<220> FEATURE:
<221> NAME/KEY: MOD_RES
<222> LOCATION: (16)..(16)
<223> OTHER INFORMATION: AMIDATION

<400> SEQUENCE: 37

Ile Asp Gly Cys Glu Leu Cys Gly Asn Pro Ala Cys Thr Gly Cys Tyr
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (8)..(8)
<223> OTHER INFORMATION: hydroxyproline
<220> FEATURE:
<221> NAME/KEY: MOD_RES
<222> LOCATION: (14)..(14)
<223> OTHER INFORMATION: AMIDATION

<400> SEQUENCE: 38

Gly Cys Glu Leu Cys Gly Asn Pro Ala Cys Thr Gly Cys Tyr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (8)..(8)
<223> OTHER INFORMATION: hydroxyproline
<220> FEATURE:
<221> NAME/KEY: MOD_RES
<222> LOCATION: (13)..(13)
<223> OTHER INFORMATION: AMIDATION

<400> SEQUENCE: 39

Gly Cys Glu Leu Cys Gly Asn Pro Ala Cys Thr Gly Cys
1               5                   10
```

```
<210> SEQ ID NO 40
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: VARIANT
<222> LOCATION: (5)..(5)
<223> OTHER INFORMATION: penicillamine
<220> FEATURE:
<221> NAME/KEY: MOD_RES
<222> LOCATION: (6)..(6)
<223> OTHER INFORMATION: allylglycine
<220> FEATURE:
<221> NAME/KEY: VARIANT
<222> LOCATION: (13)..(13)
<223> OTHER INFORMATION: penicillamine
<220> FEATURE:
<221> NAME/KEY: MOD_RES
<222> LOCATION: (14)..(14)
<223> OTHER INFORMATION: AMIDATION

<400> SEQUENCE: 40

Gly Cys Glu Leu Xaa Gly Asn Pro Ala Cys Thr Gly Xaa Tyr
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: VARIANT
<222> LOCATION: (5)..(5)
<223> OTHER INFORMATION: penicillamine
<220> FEATURE:
<221> NAME/KEY: MOD_RES
<222> LOCATION: (6)..(6)
<223> OTHER INFORMATION: allylglycine
<220> FEATURE:
<221> NAME/KEY: VARIANT
<222> LOCATION: (13)..(13)
<223> OTHER INFORMATION: penicillamine
<220> FEATURE:
<221> NAME/KEY: MOD_RES
<222> LOCATION: (14)..(14)
<223> OTHER INFORMATION: AMIDATION

<400> SEQUENCE: 41

Gly Cys Glu Leu Xaa Gly Asn Pro Ala Cys Thr Gly Xaa Tyr
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
```

```
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: N-methyl tyrosine
<220> FEATURE:
<221> NAME/KEY: MOD_RES
<222> LOCATION: (14)..(14)
<223> OTHER INFORMATION: AMIDATION

<400> SEQUENCE: 42

Gly Cys Glu Leu Cys Gly Asn Pro Ala Cys Tyr Gly Cys Tyr
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 43

Gly Cys Glu Leu Cys Gly Asn Pro Ala Cys Tyr Gly Cys
1               5                   10

<210> SEQ ID NO 44
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (11)..(11)
<223> OTHER INFORMATION: cyclohexylalanine
<220> FEATURE:
<221> NAME/KEY: MOD_RES
<222> LOCATION: (14)..(14)
<223> OTHER INFORMATION: AMIDATION

<400> SEQUENCE: 44

Gly Cys Glu Leu Cys Gly Asn Pro Ala Cys Ala Gly Cys Tyr
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
```

```
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 45

Gly Cys Glu Leu Cys Gly Asn Leu Ala Cys Thr Gly Cys Tyr
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: VARIANT
<222> LOCATION: (8)..(8)
<223> OTHER INFORMATION: sarcosine
<220> FEATURE:
<221> NAME/KEY: MOD_RES
<222> LOCATION: (14)..(14)
<223> OTHER INFORMATION: AMIDATION

<400> SEQUENCE: 46

Gly Cys Glu Leu Cys Gly Asn Xaa Ala Cys Thr Gly Cys Tyr
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 47

Gly Cys Glu Leu Cys Gly Asn Val Ala Cys Thr Gly Cys Tyr
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
```

```
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: N-methyl tyrosine
<220> FEATURE:
<221> NAME/KEY: MOD_RES
<222> LOCATION: (14)..(14)
<223> OTHER INFORMATION: AMIDATION

<400> SEQUENCE: 48

Gly Cys Glu Leu Cys Gly Asn Pro Ala Cys Tyr Gly Cys Tyr
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 49

Gly Cys Glu Leu Cys Gly Leu Pro Ala Cys Tyr Gly Cys
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 50

Gly Cys Asp Leu Cys Gly Asn Pro Ala Cys Tyr Gly Cys
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 51

Gly Cys Ser Leu Cys Gly Asn Pro Ala Cys Tyr Gly Cys
1               5                   10
```

```
<210> SEQ ID NO 52
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 52

Gly Cys Thr Leu Cys Gly Asn Pro Ala Cys Tyr Gly Cys
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine with a reduced dicarba bond
<220> FEATURE:
<221> NAME/KEY: MOD_RES
<222> LOCATION: (6)..(6)
<223> OTHER INFORMATION: allylglycine with a reduced dicarba bond
<220> FEATURE:
<221> NAME/KEY: MOD_RES
<222> LOCATION: (14)..(14)
<223> OTHER INFORMATION: AMIDATION

<400> SEQUENCE: 53

Gly Cys Glu Leu Cys Gly Asn Pro Ala Cys Thr Gly Cys Tyr
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 54

Gly Cys Gln Leu Cys Gly Asn Pro Ala Cys Tyr Gly Cys
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
```

```
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 55

Gly Cys Glu Leu Cys Gly Leu Pro Ala Cys Thr Gly Cys Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with pentenoic acid
<220> FEATURE:
<221> NAME/KEY: MOD_RES
<222> LOCATION: (5)..(5)
<223> OTHER INFORMATION: allylglycine
<220> FEATURE:
<221> NAME/KEY: MOD_RES
<222> LOCATION: (13)..(13)
<223> OTHER INFORMATION: AMIDATION

<400> SEQUENCE: 56

Cys Glu Leu Cys Gly Asn Pro Ala Cys Tyr Gly Cys Tyr
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (13)..(13)
<223> OTHER INFORMATION: allylglycine

<400> SEQUENCE: 57

Cys Cys Glu Leu Cys Gly Asn Pro Ala Cys Tyr Gly Gly
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: N-terminus capped with pentenoic acid
<220> FEATURE:
<221> NAME/KEY: MOD_RES
<222> LOCATION: (5)..(5)
<223> OTHER INFORMATION: allylglycine

<400> SEQUENCE: 58

Cys Glu Leu Cys Gly Asn Pro Ala Cys Tyr Gly Cys
1               5                   10
```

```
<210> SEQ ID NO 59
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine with a reduced dicarba bond
<220> FEATURE:
<221> NAME/KEY: MOD_RES
<222> LOCATION: (6)..(6)
<223> OTHER INFORMATION: allylglycine with a reduced dicarba bond

<400> SEQUENCE: 59

Gly Cys Glu Leu Cys Gly Asn Pro Ala Cys Tyr Gly Cys
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 60

Gly Cys Glu Leu Cys Gly Asn Val Ala Cys Tyr Gly Cys Tyr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine

<400> SEQUENCE: 61

Gly Cys Glu Leu Cys Gly Asn Val Ala Cys Tyr Gly Cys
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
<223> OTHER INFORMATION: cystathionine
```

```
<220> FEATURE:
<221> NAME/KEY: MOD_RES
<222> LOCATION: (14)..(14)
<223> OTHER INFORMATION: AMIDATION

<400> SEQUENCE: 62

Cys Xaa Glu Leu Cys Cys Asn Pro Ala Cys Tyr Gly Cys Tyr
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 63

Xaa Cys Glu Leu Cys Cys Asn Pro Ala Cys Tyr Gly Cys Tyr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: cystathionine

<400> SEQUENCE: 64

Xaa Cys Glu Leu Cys Cys Asn Pro Ala Cys Tyr Gly Cys Tyr
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 65

Cys Xaa Glu Leu Cys Cys Asn Val Ala Cys Tyr Gly Cys Tyr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
```

```
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 66

Cys Xaa Glu Leu Cys Cys Asn Val Ala Cys Thr Gly Cys Tyr
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: acetylated N-terminus
<220> FEATURE:
<221> NAME/KEY: MOD_RES
<222> LOCATION: (2)..(2)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 67

Cys Xaa Glu Leu Cys Cys Asn Val Ala Cys Thr Gly Cys Tyr
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: acetylated N-terminus
<220> FEATURE:
<221> NAME/KEY: VARIANT
<222> LOCATION: (2)..(2)
<223> OTHER INFORMATION: cystathionine
<220> FEATURE:
<221> NAME/KEY: MOD_RES
<222> LOCATION: (14)..(14)
<223> OTHER INFORMATION: ACETYLATION

<400> SEQUENCE: 68

Cys Xaa Glu Leu Cys Cys Asn Pro Ala Cys Tyr Gly Cys Tyr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: acetylated N-terminus
<220> FEATURE:
<221> NAME/KEY: VARIANT
<222> LOCATION: (2)..(2)
<223> OTHER INFORMATION: cystathionine

<400> SEQUENCE: 69
```

Cys Xaa Glu Leu Cys Cys Asn Val Ala Cys Tyr Gly Cys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
<223> OTHER INFORMATION: cystathionine

<400> SEQUENCE: 70

Cys Xaa Glu Leu Cys Cys Asn Val Ala Cys Tyr Gly Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: acetylated N-terminus
<220> FEATURE:
<221> NAME/KEY: VARIANT
<222> LOCATION: (2)..(2)
<223> OTHER INFORMATION: cystathionine

<400> SEQUENCE: 71

Cys Xaa Glu Leu Cys Cys Asn Pro Ala Cys Tyr Gly Cys
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (9)..(9)
<223> OTHER INFORMATION: cystathionine

<400> SEQUENCE: 72

Cys Cys Glu Leu Cys Asn Val Ala Xaa Tyr Gly Cys
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (10)..(10)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 73

Cys Cys Glu Leu Cys Cys Asn Val Ala Xaa Tyr Gly Cys Tyr
1               5                   10

```
<210> SEQ ID NO 74
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (10)..(10)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 74

Cys Cys Glu Leu Cys Cys Asn Val Ala Xaa Thr Gly Cys Tyr
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (6)..(6)
<223> OTHER INFORMATION: cystathionine

<400> SEQUENCE: 75

Cys Cys Glu Leu Cys Xaa Asn Val Ala Cys Tyr Gly Cys
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (6)..(6)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 76

Cys Cys Glu Leu Cys Xaa Asn Val Ala Cys Tyr Gly Cys Tyr
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (6)..(6)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 77

Cys Cys Glu Leu Cys Xaa Asn Val Ala Cys Thr Gly Cys Tyr
1               5                   10
```

```
<210> SEQ ID NO 78
<211> LENGTH: 13
<212> TYPE: PRT
<213> ORGANISM: Artificial Sequence
<220> FEATURE:
<223> O -continued

```
<210> SEQ ID NO 82
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (2)..(2)
<223> OTHER INFORMATION: allylglycine
<220> FEATURE:
<221> NAME/KEY: MOD_RES
<222> LOCATION: (5)..(5)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (10)..(10)
<223> OTHER INFORMATION: allylglycine
<220> FEATURE:
<221> NAME/KEY: MOD_RES
<222> LOCATION: (13)..(13)
<223> OTHER INFORMATION: allylglycine

<400> SEQUENCE: 82

Gly Gly Glu Leu Gly Gly Asn Pro Ala Gly Thr Gly Gly Tyr
1               5                   10

<210> SEQ ID NO 83
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 83

Cys Xaa Glu Leu Cys Cys Asn Ala Ala Cys Thr Gly Cys Tyr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (6)..(6)
<223> OTHER INFORMATION: di-aminopropionic acid
<220> FEATURE:
<221> NAME/KEY: MOD_RES
<222> LOCATION: (14)..(14)
<223> OTHER INFORMATION: AMIDATION

<400> SEQUENCE: 84

Asp Cys Glu Leu Cys Xaa Asn Val Ala Cys Thr Gly Cys Tyr
1               5                   10
```

```
<210> SEQ ID NO 85
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (2)..(2)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 85

Cys Xaa Glu Leu Cys Cys Asn Val Ala Cys Ser Gly Cys Tyr
1               5                   10

<210> SEQ ID NO 86
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: cystathionine
<220> FEATURE:
<221> NAME/KEY: MOD_RES
<222> LOCATION: (5)..(5)
<223> OTHER INFORMATION: allylglycine
<220> FEATURE:
<221> NAME/KEY: MOD_RES
<222> LOCATION: (13)..(13)
<223> OTHER INFORMATION: AMIDATION

<400> SEQUENCE: 86

Xaa Glu Leu Cys Gly Asn Val Ala Cys Thr Gly Cys Tyr
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 87

Gly Cys Glu Leu Cys Gly Asn Val Ala Cys Thr Gly Cys Tyr
1               5                   10

<210> SEQ ID NO 88
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
```

```
<222> LOCATION: (1)..(1)
<223> OTHER INFORMATION: allylglycine
<220> FEATURE:
<221> NAME/KEY: MOD_RES
<222> LOCATION: (6)..(6)
<223> OTHER INFORMATION: allylglycine
<220> FEATURE:
<221> NAME/KEY: MOD_RES
<222> LOCATION: (14)..(14)
<223> OTHER INFORMATION: AMIDATION

<400> SEQUENCE: 88

Gly Cys Glu Leu Cys Gly Asn Pro Ala Cys Thr Gly Cys Tyr
1               5                   10

<210> SEQ ID NO 89
<211> LENGTH: 13
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: cystathionine

<400> SEQUENCE: 89

Xaa Cys Glu Leu Cys Cys Asn Val Ala Cys Thr Gly Cys
1               5                   10

<210> SEQ ID NO 90
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 90

Xaa Cys Glu Leu Cys Cys Asn Val Ala Cys Thr Gly Cys Tyr
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: cystathionine
<220> FEATURE:
<221> NAME/KEY: MOD_RES
<222> LOCATION: (14)..(14)
<223> OTHER INFORMATION: AMIDATION

<400> SEQUENCE: 91

Xaa Cys Glu Leu Cys Cys Asn Val Ala Cys Tyr Gly Cys Tyr
1               5                   10

<210> SEQ ID NO 92
<211> LENGTH: 13
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: VARIANT
<222> LOCATION: (13)..(13)
<223> OTHER INFORMATION: cystathionine

<400> SEQUENCE: 92

Cys Cys Glu Leu Cys Cys Asn Val Ala Xaa Tyr Gly Cys
1               5                   10

<210> SEQ ID NO 93
<211> LENGTH: 21
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
<223> OTHER INFORMATION: Xaa1 is glutamic acid wherein the side chain
      carboxylic acid forms the peptide linkage or is absent
<220> FEATURE:
<221> NAME/KEY: VARIANT
<222> LOCATION: (2)..(2)
<223> OTHER INFORMATION: Xaa1 is lysine wherein the side chain amine
      forms the peptide linkage or is absent
<220> FEATURE:
<221> NAME/KEY: VARIANT
<222> LOCATION: (3)..(3)
<223> OTHER INFORMATION: Xaa3 is Asn or is absent
<220> FEATURE:
<221> NAME/KEY: VARIANT
<222> LOCATION: (4)..(4)
<223> OTHER INFORMATION: Xaa4 is Ser or is absent
<220> FEATURE:
<221> NAME/KEY: VARIANT
<222> LOCATION: (5)..(5)
<223> OTHER INFORMATION: Xaa5 is Ser, Asn, Ile, or is absent
<220> FEATURE:
<221> NAME/KEY: VARIANT
<222> LOCATION: (6)..(6)
<223> OTHER INFORMATION: Xaa6 is Tyr, Asp, 4-fluorophenylalanine
      ((4-F)Phe), or is absent
<220> FEATURE:
<221> NAME/KEY: VARIANT
<222> LOCATION: (7)..(7)
<223> OTHER INFORMATION: Xaa7 is Cys, cystathionine (Cth), allylglycine
      (Ag), allylglycine with a reduced dicarba bond (Hag), or Asp
<220> FEATURE:
<221> NAME/KEY: VARIANT
<222> LOCATION: (8)..(8)
<223> OTHER INFORMATION: Xaa8 is Cys, cystathionine (Cth), penicillamine
      (Pen), or allylglycine (Ag)
<220> FEATURE:
<221> NAME/KEY: VARIANT
<222> LOCATION: (9)..(9)
<223> OTHER INFORMATION: Xaa9 is Glu, Asp, Ser, Thr, or Gln
<220> FEATURE:
<221> NAME/KEY: VARIANT
<222> LOCATION: (10)..(10)
<223> OTHER INFORMATION: Xaa10 is Leu, cyclohexylalanine (Cha), Phe, or
      4-fluorophenylalanine ((4-F)Phe)
<220> FEATURE:
<221> NAME/KEY: VARIANT
<222> LOCATION: (12)..(12)
<223> OTHER INFORMATION: Xaa12 is Cys, allylglycine (Ag), Hag, or Val
<220> FEATURE:
<221> NAME/KEY: VARIANT
<222> LOCATION: (14)..(14)
<223> OTHER INFORMATION: Xaa14 is Pro, Val, sarcosine (Sar), Leu, or
      Hydroxyproline (OH-Pro)
```

```
<220> FEATURE:
<221> NAME/KEY: VARIANT
<222> LOCATION: (17)..(17)
<223> OTHER INFORMATION: Xaa17 is Tyr, Thr, cyclohexylalanine (Cha),
      4-fluorophenylalanine ((4-F)Phe), Phe, or Ala
<220> FEATURE:
<221> NAME/KEY: VARIANT
<222> LOCATION: (20)..(20)
<223> OTHER INFORMATION: Xaa20 is Tyr, Leu, 4-fluorophenylalanine
      ((4-F)Phe), cyclohexylalanine (Cha), D-Tyr, N-Methyl Tyr (Nme-Tyr)
      or is absent
<220> FEATURE:
<221> NAME/KEY: VARIANT
<222> LOCATION: (21)..(21)
<223> OTHER INFORMATION: Xaa21 is absent or Asnt

<400> SEQUENCE: 93

Xaa Xaa Xaa Xaa Xaa Xaa Xaa Xaa Xaa Xaa Cys Xaa Asn Xaa Ala Cys
1               5                   10                  15

Xaa Gly Cys Xaa Xaa
            20

<210> SEQ ID NO 94
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 94

Cys Cys Glu Leu Cys Cys Asn Pro Ala Cys Thr Gly Cys Tyr
1               5                   10
```

What is claimed is:

1. A peptide or a pharmaceutically acceptable salt thereof, wherein the peptide comprises the amino acid sequence $Xaa_1$, $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Xaa_{15}$ $Xaa_{16}$ $Xaa_{17}$ $Gly_{18}$ $Xaa_{19}$ $Xaa_{20}$ $Xaa_{21}$ (SEQ ID NO: 1), wherein:

$Xaa_1$ is absent;
$Xaa_2$ is absent;
$Xaa_3$ is absent;
$Xaa_4$ is absent;
$Xaa_5$ is absent;
$Xaa_6$ is absent;
$Xaa_7$ is Ag, Cys, or Cth;
$Xaa_8$ is Cys or Cth;
$Xaa_9$ is Glu;
$Xaa_{10}$ is Leu;
$Xaa_{11}$ is Cys, Ag, or penicillamine (Pen);
$Xaa_{12}$ is Ag or Cys;
$Xaa_{13}$ is Asn or Leu;
$Xaa_{14}$ is Val or Pro;
$Xaa_{16}$ is Cys, Ag, Pen or Cth;
$Xaa_{17}$ is Tyr or Thr;
$Xaa_{19}$ is Cys, Ag or Pen;
$Xaa_{20}$ is Tyr or is absent; and
$Xaa_{21}$ is absent or Asn; and wherein the peptide contains a covalent bond between $Xaa_7$ and $Xaa_{12}$, $Xaa_8$ and $Xaa_{16}$ and $Xaa_{11}$ and $Xaa_{19}$.

2. The peptide or pharmaceutically acceptable salt thereof according to claim 1, wherein the peptide comprises the amino acid sequence:

(SEQ ID NO: 2)
H-Ag Cys Glu Leu Cys Ag Asn Pro Ala Cys Thr Gly Cys Tyr-$NH_2$;

(SEQ ID NO: 26)
H-Ag Cys Glu Leu Cys Ag Asn Pro Ala Cys Tyr Gly Cys Tyr-$NH_2$;

(SEQ ID NO: 43)
H-Ag Cys Glu Leu Cys Ag Asn Pro Ala Cys Tyr Gly Cys-COOH;

(SEQ ID NO: 47)
H-Ag Cys Glu Leu Cys Ag Asn Val Ala Cys Thr Gly Cys Tyr-$NH_2$;

(SEQ ID NO: 62)
H-Ag Cys Glu Leu Cys Ag Asn Val Ala Cys Tyr Gly Cys Tyr-$NH_2$;

(SEQ ID NO: 64)
H-Cth Cys Glu Leu Cys Cys Asn Pro Ala Cys Tyr Gly Cys-COOH;

-continued (SEQ ID NO: 68)
Ac-Cys Cth Glu Leu Cys Cys Asn Pro Ala Cys Tyr Gly Cys Tyr-$NH_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;
or (SEQ ID NO: 71)
Ac-Cys Cth Glu Leu Cys Cys Asn Pro Ala Cys Tyr Gly Cys-COOH.

3. A peptide or a pharmaceutically acceptable salt thereof, wherein the peptide comprises the amino acid sequence:

(SEQ ID NO: 2)
H-Ag Cys Glu Leu Cys Ag Asn Pro Ala Cys Thr Gly Cys Tyr-$NH_2$;

(SEQ ID NO: 3)
C12-BE BK Asn Ser Ser Tyr Cys Cys Glu Leu Cys Cys Asn Pro Ala Cys Thr Gly Cys Tyr-$NH_2$;

(SEQ ID NO: 4)
C16-BE BK Asn Ser Ser Tyr Cys Cys Glu Leu Cys Cys Asn Pro Ala Cys Thr Gly Cys Tyr-$NH_2$;

(SEQ ID NO: 5)
C12-BE BK Asn Ser Ser Tyr Cys Cys Glu Leu Cys Cys Asn Pro Ala Cys Thr Gly Cys Tyr-COOH;

(SEQ ID NO: 6)
C14-BE BK Asn Ser Ser Tyr Cys Cys Glu Leu Cys Cys Asn Pro Ala Cys Thr Gly Cys Tyr-COOH;

(SEQ ID NO: 7)
C16-BE BK Asn Ser Ser Tyr Cys Cys Glu Leu Cys Cys Asn Pro Ala Cys Thr Gly Cys Tyr-COOH;

(SEQ ID NO: 8)
H-Cys Ag Glu Leu Cys Cys Asn Pro Ala Ag Thr Gly Cys Tyr-$NH_2$;

(SEQ ID NO: 9)
H-Asn Asp Asp Ag Glu Leu Cys Val Asn Val Ala Ag Thr Gly Cys Leu-$NH_2$;

(SEQ ID NO: 10)
H-Asn Asp Asp Cys Glu Leu Ag Val Asn Val Ala Cys Thr Gly Ag Leu-$NH_2$;

(SEQ ID NO: 11)
C18-BE BK Asn Ser Ser Tyr Cys Cys Glu Leu Cys Cys Asn Pro Ala Cys Thr Gly Cys Tyr-COOH;

(SEQ ID NO: 12)
H-Ag Cys Glu Leu Cys Ag Asn Pro Ala Cys Thr Gly Cys-$NH_2$;

(SEQ ID NO: 13)
H-Ag Cys Glu Leu Cys Ag Asn Pro Ala Cys Ala Gly Cys-$NH_2$;

(SEQ ID NO: 14)
H-Ag Cys Glu Phe Cys Ag Asn Pro Ala Cys Thr Gly Cys Tyr-$NH_2$;

(SEQ ID NO: 15)
H-Ag Cys Glu (4-F)Phe Cys Ag Asn Pro Ala Cys Thr Gly Cys-$NH_2$;

(SEQ ID NO: 16)
H-Ag Cys Glu (4-F)Phe Cys Ag Asn Pro Ala Cys Thr Gly Cys Tyr-$NH_2$;

-continued

```
                                                 (SEQ ID NO: 17)
H-Ag Cys Glu (4-F)Phe Cys Ag Asn Pro Ala Cys Thr Gly Cys (4-F)Phe-
NH2;

(SEQ ID NO: 18)
H-Cys Cys Glu Leu Ag Cys Asn Pro Ala Cys Thr Gly Ag Tyr-NH2;

(SEQ ID NO: 19)
H-Ag Cys Glu Phe Cys Ag Asn Pro Ala Cys Thr Gly Cys-NH2;

(SEQ ID NO: 20)
H-Ag Cys Glu Phe Cys Ag Asn Pro Ala Cys Thr Gly Cys (4-F)Phe-NH2;

(SEQ ID NO: 21)
H-Cys Cys Glu (4-F)Phe Cys Cys Asn Pro Ala Cys Thr Gly Cys Tyr-NH2;

(SEQ ID NO: 22)
H-Cys Cys Glu (4-F)Phe Cys Cys Asn Pro Ala Cys Thr Gly Cys (4-F)Phe-
NH2;

(SEQ ID NO: 23)
H-Ag Cys Glu Leu Cys Ag Asn Pro Ala Cys Thr Gly Cys (4-F)Phe-NH2;

(SEQ ID NO: 24)
H-(4-F)Phe Ag Cys Glu Leu Cys Ag Asn Pro Ala Cys Thr Gly Cys (4-
F)Phe-NH2;

(SEQ ID NO: 25)
H-Ag Cys Glu Leu Cys Ag Asn Pro Ala Cys Ala Gly Cys Tyr-NH2;

(SEQ ID NO: 26)
H-Ag Cys Glu Leu Cys Ag Asn Pro Ala Cys Tyr Gly Cys Tyr-NH2;

(SEQ ID NO: 27)
H-Ag Cys Glu Leu Cys Ag Asn Pro Ala Cys Phe Gly Cys Tyr-NH2;

(SEQ ID NO: 28)
H-Ag Cys Glu Leu Cys Ag Asn Pro Ala Cys (4-F)Phe Gly Cys Tyr-NH2;

(SEQ ID NO: 29)
H-Ag Cys Glu Leu Cys Ag Asn Pro Ala Cys Thr Gly Cys Leu-NH2;

(SEQ ID NO: 30)
H-Ag Cys Glu Leu Cys Ag Asn Pro Ala Cys Thr Gly Cys Cha-NH2;

(SEQ ID NO: 31)
H-Ag Cys Glu Cha Cys Ag Asn Pro Ala Cys Thr Gly Cys Tyr-NH2;

(SEQ ID NO: 32)
H-Ag Cys Glu Leu Cys Ag Asn Pro Ala Cys Thr Gly Cys D-Tyr-NH2;

(SEQ ID NO: 33)
H-Ag Pen Glu Leu Cys Ag Asn Pro Ala Pen Thr Gly Cys Tyr-NH2;

(SEQ ID NO: 34)
H-Ag Cys Glu Leu Cys Ag Asn Pro Ala Cys Thr Gly Cys Leu Asn-NH2;

(SEQ ID NO: 35)
H-Ag Cys Glu Leu Cys Ag Asn Pro Ala Cys Thr Gly Cys Tyr Asn-NH2;

(SEQ ID NO: 36)
H-Asp Ag Cys Glu Leu Cys Ag Asn Pro Ala Cys Thr Gly Cys Tyr-NH2;

(SEQ ID NO: 37)
H-Ile Asp Ag Cys Glu Leu Cys Ag Asn Pro Ala Cys Thr Gly Cys Tyr-
NH2;

(SEQ ID NO: 38)
H-Ag Cys Glu Leu Cys Ag Asn OH-Pro Ala Cys Thr Gly Cys Tyr-NH2;

(SEQ ID NO: 39)
H-Ag Cys Glu Leu Cys Ag Asn OH-Pro Ala Cys Thr Gly Cys-NH2;

(SEQ ID NO: 40)
H-Ag Cys Glu Leu Pen Ag Asn Pro Ala Cys Thr Gly Pen Tyr-NH2;
```

-continued (SEQ ID NO: 41)
H-Ag Cys Glu Leu Pen Ag Asn Pro Ala Cys Thr Gly Pen Tyr-$NH_2$;

(SEQ ID NO: 42)
H-Ag Cys Glu Leu Cys Ag Asn Pro Ala Cys Tyr Gly Cys Nme-Tyr-$NH_2$;

(SEQ ID NO: 43)
H-Ag Cys Glu Leu Cys Ag Asn Pro Ala Cys Tyr Gly Cys-COOH;

(SEQ ID NO: 44)
H-Ag Cys Glu Leu Cys Ag Asn Pro Ala Cys Cha Gly Cys Tyr-$NH_2$;

(SEQ ID NO: 45)
H-Ag Cys Glu Leu Cys Ag Asn Leu Ala Cys Thr Gly Cys Tyr-$NH_2$;

(SEQ ID NO: 46)
H-Ag Cys Glu Leu Cys Ag Asn Sar Ala Cys Thr Gly Cys Tyr-$NH_2$;

(SEQ ID NO: 47)
H-Ag Cys Glu Leu Cys Ag Asn Val Ala Cys Thr Gly Cys Tyr-$NH_2$;

(SEQ ID NO: 48)
H-Ag Cys Glu Leu Cys Ag Asn Pro Ala Cys Tyr Gly Cys Nme-Tyr-$NH_2$;

(SEQ ID NO: 49)
H-Ag Cys Glu Leu Cys Ag Leu Pro Ala Cys Tyr Gly Cys-COOH;

(SEQ ID NO: 50)
H-Ag Cys Asp Leu Cys Ag Asn Pro Ala Cys Tyr Gly Cys-COOH;

(SEQ ID NO: 51)
H-Ag Cys Ser Leu Cys Ag Asn Pro Ala Cys Tyr Gly Cys-COOH;

(SEQ ID NO: 52)
H-Ag Cys Thr Leu Cys Ag Asn Pro Ala Cys Tyr Gly Cys-COOH;

(SEQ ID NO: 53)
H-Hag Cys Glu Leu Cys Hag Asn Pro Ala Cys Thr Gly Cys Tyr-$NH_2$;

(SEQ ID NO: 54)
H-Ag Cys Gln Leu Cys Ag Asn Pro Ala Cys Tyr Gly Cys-COOH;

(SEQ ID NO: 55)
H-Ag Cys Glu Leu Cys Ag Leu Pro Ala Cys Thr Gly Cys Tyr-$NH_2$;

(SEQ ID NO: 56)
Pent-Cys Glu Leu Cys Ag Asn Pro Ala Cys Tyr Gly Cys Tyr-$NH_2$;

(SEQ ID NO: 57)
H-Cys Cys Glu Leu Cys Ag Asn Pro Ala Cys Tyr Gly Ag-COOH;

(SEQ ID NO: 58)
Pent-Cys Glu Leu Cys Ag Asn Pro Ala Cys Tyr Gly Cys-COOH;

(SEQ ID NO: 59)
H-Hag Cys Glu Leu Cys Hag Asn Pro Ala Cys Tyr Gly Cys-COOH;

(SEQ ID NO: 60)
H-Ag Cys Glu Leu Cys Ag Asn Val Ala Cys Tyr Gly Cys Tyr-$NH_2$;

(SEQ ID NO: 61)
H-Ag Cys Glu Leu Cys Ag Asn Val Ala Cys Tyr Gly Cys-COOH;

(SEQ ID NO: 62)
H-Cys Cth Glu Leu Cys Cys Asn Pro Ala Cys Tyr Gly Cys Tyr-$NH_2$;

(SEQ ID NO: 63)
H-Cth Cys Glu Leu Cys Cys Asn Pro Ala Cys Tyr Gly Cys Tyr-$NH_2$;

(SEQ ID NO: 64)
H-Cth Cys Glu Leu Cys Cys Asn Pro Ala Cys Tyr Gly Cys-COOH;

(SEQ ID NO: 65)
H-Cys Cth Glu Leu Cys Cys Asn Val Ala Cys Tyr Gly Cys Tyr-$NH_2$;

(SEQ ID NO: 66)
H-Cys Cth Glu Leu Cys Cys Asn Val Ala Cys Thr Gly Cys Tyr-$NH_2$;

(SEQ ID NO: 67)
Ac-Cys Cth Glu Leu Cys Cys Asn Val Ala Cys Thr Gly Cys Tyr-$NH_2$;

-continued (SEQ ID NO: 68)
Ac-Cys Cth Glu Leu Cys Cys Asn Pro Ala Cys Tyr Gly Cys Tyr-$NH_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;

(SEQ ID NO: 71)
Ac-Cys Cth Glu Leu Cys Cys Asn Pro Ala Cys Tyr Gly Cys-COOH;

(SEQ ID NO: 72)
H-Cys Cys Glu Leu Cys Asn Val Ala Cth Tyr Gly Cys-COOH;

(SEQ ID NO: 73)
H-Cys Cys Glu Leu Cys Cys Asn Val Ala Cth Tyr Gly Cys Tyr-$NH_2$;

(SEQ ID NO: 74)
H-Cys Cys Glu Leu Cys Cys Asn Val Ala Cth Thr Gly Cys Tyr-$NH_2$;

(SEQ ID NO: 75)
H-Cys Cys Glu Leu Cys Cth Asn Val Ala Cys Tyr Gly Cys-COOH;

(SEQ ID NO: 76)
H-Cys Cys Glu Leu Cys Cth Asn Val Ala Cys Tyr Gly Cys Tyr-$NH_2$;

(SEQ ID NO: 77)
H-Cys Cys Glu Leu Cys Cth Asn Val Ala Cys Thr Gly Cys Tyr-$NH_2$;

(SEQ ID NO: 78)
4-Mepip-Cys Cth Glu Leu Cys Cys Asn Val Ala Cys Tyr Gly Cys-COOH;

(SEQ ID NO: 79)
H-Cys Cth Glu Leu Cys Cys Asn Val Ala Cys Thr Gly Cys-COOH;

(SEQ ID NO: 80)
H-Cys Cth Glu Leu Cys Cys Asn Val Ala Cys Thr Gly Cys-$NH_2$;

(SEQ ID NO: 81)
H-Cys Cth Glu Leu Cys Cys Asn Val Ala Cys Phe Gly Cys-COOH;

(SEQ ID NO: 82)
H-Ag Ag Glu Leu Ag Ag Asn Pro Ala Ag Thr Gly Ag Tyr-COOH;

(SEQ ID NO: 83)
H-Cys Cth Glu Leu Cys Cys Asn Ala Ala Cys Thr Gly Cys Tyr-$NH_2$;

(SEQ ID NO: 84)
H-Asp Cys Glu Leu Cys Dpr Asn Val Ala Cys Thr Gly Cys Tyr-$NH_2$;

(SEQ ID NO: 85)
H-Cys Cth Glu Leu Cys Cys Asn Val Ala Cys Ser Gly Cys Tyr-$NH_2$;

(SEQ ID NO: 86)
H-Cth Glu Leu Cys Ag Asn Val Ala Cys Thr Gly Cys Tyr-$NH_2$;

(SEQ ID NO: 87)
H-Ag Cys Glu Leu Cys Ag Asn Val Ala Cys Thr Gly Cys Tyr-$NH_2$;

(SEQ ID NO: 88)
H-Ag Cys Glu Leu Cys Ag Asn Pro Ala Cys Thr Gly Cys Tyr-$NH_2$;

(SEQ ID NO: 89)
H-Cth Cys Glu Leu Cys Cys Asn Val Ala Cys Thr Gly Cys-COOH;

(SEQ ID NO: 90)
H-Cth Cys Glu Leu Cys Cys Asn Val Ala Cys Thr Gly Cys Tyr-$NH_2$;

(SEQ ID NO: 91)
H-Cth Cys Glu Leu Cys Cys Asn Val Ala Cys Tyr Gly Cys Tyr-$NH_2$;
or (SEQ ID NO: 92)
H-Cys Cys Glu Leu Cys Cys Asn Val Ala Cth Tyr Gly Cys-COOH.

4. A peptide or a pharmaceutically acceptable salt thereof, wherein the peptide consists of the amino acid sequence $Xaa_1$ $Xaa_2$ $Xaa_3$ $Xaa_4$ $Xaa_5$ $Xaa_6$ $Xaa_7$ $Xaa_8$ $Xaa_9$ $Xaa_{10}$ $Xaa_{11}$ $Xaa_{12}$ $Xaa_{13}$ $Xaa_{14}$ $Ala_{15}$ $Xaa_{16}$ $Xaa_{17}$ $Glyl_{18}$ Xaa₁₉ Xaa₂₀ Xaa₂₁ (SEQ ID NO: 1), or a pharmaceutically acceptable salt thereof;
wherein:
Xaa₁ is absent;
Xaa₂ is absent;
Xaa₃ is absent;
Xaa₄ is absent;
Xaa₅ is absent;
Xaa₆ is absent;
Xaa₇ is Ag, Cys, or Cth;
Xaa₈ is Cys or Cth;
Xaa₉ is Glu;
Xaa₁₀ is Leu;
Xaa₁₁ is Cys, Ag, or penicillamine (Pen);
Xaa₁₂ is Ag or Cys;
Xaa₁₃ is Asn or Leu;
Xaa₁₄ is Val or Pro;
Xaa₁₆ is Cys, Ag, Pen or Cth;
Xaa₁₇ is Tyr or Thr;
Xaa₁₉ is Cys, Ag or Pen;
Xaa₂₀ is Tyr or is absent; and
Xaa₂₁ is absent or Asn; and
wherein the peptide contains a covalent bond between Xaa₇ and Xaa₁₂, Xaa₈ and Xaa₁₆ and Xaa₁₁ and Xaa₁₉.

5. The peptide or pharmaceutically acceptable salt thereof according to claim 4, wherein the peptide consists of the amino acid sequence

```
                                                           (SEQ ID NO: 2)
H-Ag Cys Glu Leu Cys Ag Asn Pro Ala Cys Thr Gly Cys Tyr-NH₂;

(SEQ ID NO: 26)
H-Ag Cys Glu Leu Cys Ag Asn Pro Ala Cys Tyr Gly Cys Tyr-NH₂;

(SEQ ID NO: 43)
H-Ag Cys Glu Leu Cys Ag Asn Pro Ala Cys Tyr Gly Cys-COOH;

(SEQ ID NO: 47)
H-Ag Cys Glu Leu Cys Ag Asn Val Ala Cys Thr Gly Cys Tyr-NH₂;

(SEQ ID NO: 62)
H-Ag Cys Glu Leu Cys Ag Asn Val Ala Cys Tyr Gly Cys Tyr-NH₂;

(SEQ ID NO: 64)
H-Cth Cys Glu Leu Cys Cys Asn Pro Ala Cys Tyr Gly Cys-COOH;

(SEQ ID NO: 68)
Ac-Cys Cth Glu Leu Cys Cys Asn Pro Ala Cys Tyr Gly Cys Tyr-NH₂;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;
or (SEQ ID NO: 71)
Ac-Cys Cth Glu Leu Cys Cys Asn Pro Ala Cys Tyr Gly Cys-COOH.
```

6. A peptide or a pharmaceutically acceptable salt thereof, wherein the peptide consists of the amino acid sequence:

```
                                                           (SEQ ID NO: 2)
H-Ag Cys Glu Leu Cys Ag Asn Pro Ala Cys Thr Gly Cys Tyr-NH₂;

(SEQ ID NO: 3)
C12-BE BK Asn Ser Ser Tyr Cys Cys Glu Leu Cys Cys Asn Pro Ala Cys

Thr Gly Cys Tyr-NH₂;

(SEQ ID NO: 4)
C16-BE BK Asn Ser Ser Tyr Cys Cys Glu Leu Cys Cys Asn Pro Ala Cys

Thr Gly Cys Tyr-NH₂;

(SEQ ID NO: 5)
C12-BE BK Asn Ser Ser Tyr Cys Cys Glu Leu Cys Cys Asn Pro Ala Cys

Thr Gly Cys Tyr-COOH;

(SEQ ID NO: 6)
C14-BE BK Asn Ser Ser Tyr Cys Cys Glu Leu Cys Cys Asn Pro Ala Cys

Thr Gly Cys Tyr-COOH;

(SEQ ID NO: 7)
C16-BE BK Asn Ser Ser Tyr Cys Cys Glu Leu Cys Cys Asn Pro Ala Cys

Thr Gly Cys Tyr-COOH;
```

-continued

```
                                                 (SEQ ID NO: 8)
H-Cys Ag Glu Leu Cys Cys Asn Pro Ala Ag Thr Gly Cys Tyr-NH₂;

(SEQ ID NO: 9)
H-Asn Asp Asp Ag Glu Leu Cys Val Asn Val Ala Ag Thr Gly Cys Leu-
NH₂;

(SEQ ID NO: 10)
H-Asn Asp Asp Cys Glu Leu Ag Val Asn Val Ala Cys Thr Gly Ag Leu-
NH₂;

(SEQ ID NO: 11)
C18-BE BK Asn Ser Ser Tyr Cys Cys Glu Leu Cys Cys Asn Pro Ala Cys
Thr Gly Cys Tyr-COOH;

(SEQ ID NO: 12)
H-Ag Cys Glu Leu Cys Ag Asn Pro Ala Cys Thr Gly Cys-NH₂;

(SEQ ID NO: 13)
H-Ag Cys Glu Leu Cys Ag Asn Pro Ala Cys Ala Gly Cys-NH₂;

(SEQ ID NO: 14)
H-Ag Cys Glu Phe Cys Ag Asn Pro Ala Cys Thr Gly Cys Tyr-NH₂;

(SEQ ID NO: 15)
H-Ag Cys Glu (4-F)Phe Cys Ag Asn Pro Ala Cys Thr Gly Cys-NH₂;

(SEQ ID NO: 16)
H-Ag Cys Glu (4-F)Phe Cys Ag Asn Pro Ala Cys Thr Gly Cys Tyr-NH₂;

(SEQ ID NO: 17)
H-Ag Cys Glu (4-F)Phe Cys Ag Asn Pro Ala Cys Thr Gly Cys (4-F)Phe-
NH₂;

(SEQ ID NO: 18)
H-Cys Cys Glu Leu Ag Cys Asn Pro Ala Cys Thr Gly Ag Tyr-NH₂;

(SEQ ID NO: 19)
H-Ag Cys Glu Phe Cys Ag Asn Pro Ala Cys Thr Gly Cys-NH₂;

(SEQ ID NO: 20)
H-Ag Cys Glu Phe Cys Ag Asn Pro Ala Cys Thr Gly Cys (4-F)Phe-NH₂;

(SEQ ID NO: 21)
H-Cys Cys Glu (4-F)Phe Cys Cys Asn Pro Ala Cys Thr Gly Cys Tyr-NH₂;

(SEQ ID NO: 22)
H-Cys Cys Glu (4-F)Phe Cys Cys Asn Pro Ala Cys Thr Gly Cys (4-F)Phe-
NH₂;

(SEQ ID NO: 23)
H-Ag Cys Glu Leu Cys Ag Asn Pro Ala Cys Thr Gly Cys (4-F)Phe-NH₂;

(SEQ ID NO: 24)
H-(4-F)Phe Ag Cys Glu Leu Cys Ag Asn Pro Ala Cys Thr Gly Cys (4-
F)Phe-NH₂;

(SEQ ID NO: 25)
H-Ag Cys Glu Leu Cys Ag Asn Pro Ala Cys Ala Gly Cys Tyr-NH₂;

(SEQ ID NO: 26)
H-Ag Cys Glu Leu Cys Ag Asn Pro Ala Cys Tyr Gly Cys Tyr-NH₂;

(SEQ ID NO: 27)
H-Ag Cys Glu Leu Cys Ag Asn Pro Ala Cys Phe Gly Cys Tyr-NH₂;

(SEQ ID NO: 28)
H-Ag Cys Glu Leu Cys Ag Asn Pro Ala Cys (4-F)Phe Gly Cys Tyr-NH₂;

(SEQ ID NO: 29)
H-Ag Cys Glu Leu Cys Ag Asn Pro Ala Cys Thr Gly Cys Leu-NH₂;

(SEQ ID NO: 30)
H-Ag Cys Glu Leu Cys Ag Asn Pro Ala Cys Thr Gly Cys Cha-NH₂;
```

```
                                                        (SEQ ID NO: 31)
H-Ag Cys Glu Cha Cys Ag Asn Pro Ala Cys Thr Gly Cys Tyr-NH₂;

(SEQ ID NO: 32)
H-Ag Cys Glu Leu Cys Ag Asn Pro Ala Cys Thr Gly Cys D-Tyr-NH₂;

(SEQ ID NO: 33)
H-Ag Pen Glu Leu Cys Ag Asn Pro Ala Pen Thr Gly Cys Tyr-NH₂;

(SEQ ID NO: 34)
H-Ag Cys Glu Leu Cys Ag Asn Pro Ala Cys Thr Gly Cys Leu Asn-NH₂;

(SEQ ID NO: 35)
H-Ag Cys Glu Leu Cys Ag Asn Pro Ala Cys Thr Gly Cys Tyr Asn-NH₂;

(SEQ ID NO: 36)
H-Asp Ag Cys Glu Leu Cys Ag Asn Pro Ala Cys Thr Gly Cys Tyr-NH₂;

(SEQ ID NO: 37)
H-Ile Asp Ag Cys Glu Leu Cys Ag Asn Pro Ala Cys Thr Gly Cys Tyr-
NH₂;

(SEQ ID NO: 38)
H-Ag Cys Glu Leu Cys Ag Asn OH-Pro Ala Cys Thr Gly Cys Tyr-NH₂;

(SEQ ID NO: 39)
H-Ag Cys Glu Leu Cys Ag Asn OH-Pro Ala Cys Thr Gly Cys-NH₂;

(SEQ ID NO: 40)
H-Ag Cys Glu Leu Pen Ag Asn Pro Ala Cys Thr Gly Pen Tyr-NH₂;

(SEQ ID NO: 41)
H-Ag Cys Glu Leu Pen Ag Asn Pro Ala Cys Thr Gly Pen Tyr-NH₂;

(SEQ ID NO: 42)
H-Ag Cys Glu Leu Cys Ag Asn Pro Ala Cys Tyr Gly Cys Nme-Tyr-NH₂;

(SEQ ID NO: 43)
H-Ag Cys Glu Leu Cys Ag Asn Pro Ala Cys Tyr Gly Cys-COOH;

(SEQ ID NO: 44)
H-Ag Cys Glu Leu Cys Ag Asn Pro Ala Cys Cha Gly Cys Tyr-NH₂;

(SEQ ID NO: 45)
H-Ag Cys Glu Leu Cys Ag Asn Leu Ala Cys Thr Gly Cys Tyr-NH₂;

(SEQ ID NO: 46)
H-Ag Cys Glu Leu Cys Ag Asn Sar Ala Cys Thr Gly Cys Tyr-NH₂;

(SEQ ID NO: 47)
H-Ag Cys Glu Leu Cys Ag Asn Val Ala Cys Thr Gly Cys Tyr-NH₂;

(SEQ ID NO: 48)
H-Ag Cys Glu Leu Cys Ag Asn Pro Ala Cys Tyr Gly Cys Nme-Tyr-NH₂;

(SEQ ID NO: 49)
H-Ag Cys Glu Leu Cys Ag Leu Pro Ala Cys Tyr Gly Cys-COOH;

(SEQ ID NO: 50)
H-Ag Cys Asp Leu Cys Ag Asn Pro Ala Cys Tyr Gly Cys-COOH;

(SEQ ID NO: 51)
H-Ag Cys Ser Leu Cys Ag Asn Pro Ala Cys Tyr Gly Cys-COOH;

(SEQ ID NO: 52)
H-Ag Cys Thr Leu Cys Ag Asn Pro Ala Cys Tyr Gly Cys-COOH;

(SEQ ID NO: 53)
H-Hag Cys Glu Leu Cys Hag Asn Pro Ala Cys Thr Gly Cys Tyr-NH₂;

(SEQ ID NO: 54)
H-Ag Cys Gln Leu Cys Ag Asn Pro Ala Cys Tyr Gly Cys-COOH;

(SEQ ID NO: 55)
H-Ag Cys Glu Leu Cys Ag Leu Pro Ala Cys Thr Gly Cys Tyr-NH₂;

(SEQ ID NO: 56)
Pent-Cys Glu Leu Cys Ag Asn Pro Ala Cys Tyr Gly Cys Tyr-NH₂;
```

-continued (SEQ ID NO: 57)
H-Cys Cys Glu Leu Cys Ag Asn Pro Ala Cys Tyr Gly Ag-COOH;

(SEQ ID NO: 58)
Pent-Cys Glu Leu Cys Ag Asn Pro Ala Cys Tyr Gly Cys-COOH;

(SEQ ID NO: 59)
H-Hag Cys Glu Leu Cys Hag Asn Pro Ala Cys Tyr Gly Cys-COOH;

(SEQ ID NO: 60)
H-Ag Cys Glu Leu Cys Ag Asn Val Ala Cys Tyr Gly Cys Tyr-NH$_2$;

(SEQ ID NO: 61)
H-Ag Cys Glu Leu Cys Ag Asn Val Ala Cys Tyr Gly Cys-COOH;

(SEQ ID NO: 62)
H-Cys Cth Glu Leu Cys Cys Asn Pro Ala Cys Tyr Gly Cys Tyr-NH$_2$;

(SEQ ID NO: 63)
H-Cth Cys Glu Leu Cys Cys Asn Pro Ala Cys Tyr Gly Cys Tyr-NH$_2$;

(SEQ ID NO: 64)
H-Cth Cys Glu Leu Cys Cys Asn Pro Ala Cys Tyr Gly Cys-COOH;

(SEQ ID NO: 65)
H-Cys Cth Glu Leu Cys Cys Asn Val Ala Cys Tyr Gly Cys Tyr-NH$_2$;

(SEQ ID NO: 66)
H-Cys Cth Glu Leu Cys Cys Asn Val Ala Cys Thr Gly Cys Tyr-NH$_2$;

(SEQ ID NO: 67)
Ac-Cys Cth Glu Leu Cys Cys Asn Val Ala Cys Thr Gly Cys Tyr-NH$_2$;

(SEQ ID NO: 68)
Ac-Cys Cth Glu Leu Cys Cys Asn Pro Ala Cys Tyr Gly Cys Tyr-NH$_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;

(SEQ ID NO: 71)
Ac-Cys Cth Glu Leu Cys Cys Asn Pro Ala Cys Tyr Gly Cys-COOH;

(SEQ ID NO: 72)
H-Cys Cys Glu Leu Cys Asn Val Ala Cth Tyr Gly Cys-COOH;

(SEQ ID NO: 73)
H-Cys Cys Glu Leu Cys Cys Asn Val Ala Cth Tyr Gly Cys Tyr-NH$_2$;

(SEQ ID NO: 74)
H-Cys Cys Glu Leu Cys Cys Asn Val Ala Cth Thr Gly Cys Tyr-NH$_2$;

(SEQ ID NO: 75)
H-Cys Cys Glu Leu Cys Cth Asn Val Ala Cys Tyr Gly Cys-COOH;

(SEQ ID NO: 76)
H-Cys Cys Glu Leu Cys Cth Asn Val Ala Cys Tyr Gly Cys Tyr-NH$_2$;

(SEQ ID NO: 77)
H-Cys Cys Glu Leu Cys Cth Asn Val Ala Cys Thr Gly Cys Tyr-NH$_2$;

(SEQ ID NO: 78)
4-Mepip-Cys Cth Glu Leu Cys Cys Asn Val Ala Cys Tyr Gly Cys-COOH;

(SEQ ID NO: 79)
H-Cys Cth Glu Leu Cys Cys Asn Val Ala Cys Thr Gly Cys-COOH;

(SEQ ID NO: 80)
H-Cys Cth Glu Leu Cys Cys Asn Val Ala Cys Thr Gly Cys-NH$_2$;

(SEQ ID NO: 81)
H-Cys Cth Glu Leu Cys Cys Asn Val Ala Cys Phe Gly Cys-COOH;

(SEQ ID NO: 82)
H-Ag Ag Glu Leu Ag Ag Asn Pro Ala Ag Thr Gly Ag Tyr-COOH;

(SEQ ID NO: 83)
H-Cys Cth Glu Leu Cys Cys Asn Ala Ala Cys Thr Gly Cys Tyr-NH$_2$;

-continued (SEQ ID NO: 84)
H-Asp Cys Glu Leu Cys Dpr Asn Val Ala Cys Thr Gly Cys Tyr-NH$_2$;

(SEQ ID NO: 85)
H-Cys Cth Glu Leu Cys Cys Asn Val Ala Cys Ser Gly Cys Tyr-NH$_2$;

(SEQ ID NO: 86)
H-Cth Glu Leu Cys Ag Asn Val Ala Cys Thr Gly Cys Tyr-NH$_2$;

(SEQ ID NO: 87)
H-Ag Cys Glu Leu Cys Ag Asn Val Ala Cys Thr Gly Cys Tyr-NH$_2$;

(SEQ ID NO: 88)
H-Ag Cys Glu Leu Cys Ag Asn Pro Ala Cys Thr Gly Cys Tyr-NH$_2$;

(SEQ ID NO: 89)
H-Cth Cys Glu Leu Cys Cys Asn Val Ala Cys Thr Gly Cys-COOH;

(SEQ ID NO: 90)
H-Cth Cys Glu Leu Cys Cys Asn Val Ala Cys Thr Gly Cys Tyr-NH$_2$;

(SEQ ID NO: 91)
H-Cth Cys Glu Leu Cys Cys Asn Val Ala Cys Tyr Gly Cys Tyr-NH$_2$;
or (SEQ ID NO: 92)
H-Cys Cys Glu Leu Cys Cys Asn Val Ala Cth Tyr Gly Cys-COOH.

7. A pharmaceutical composition comprising a peptide or a pharmaceutically acceptable salt thereof, wherein the peptide or pharmaceutically acceptable salt thereof comprises the amino acid sequence:

(SEQ ID NO: 2)
H-Ag Cys Glu Leu Cys Ag Asn Pro Ala Cys Thr Gly Cys Tyr-NH$_2$;

(SEQ ID NO: 3)
C12-BE BK Asn Ser Ser Tyr Cys Cys Glu Leu Cys Cys Asn Pro Ala Cys Thr Gly Cys Tyr-NH$_2$;

(SEQ ID NO: 4)
C16-BE BK Asn Ser Ser Tyr Cys Cys Glu Leu Cys Cys Asn Pro Ala Cys Thr Gly Cys Tyr-NH$_2$;

(SEQ ID NO: 5)
C12-BE BK Asn Ser Ser Tyr Cys Cys Glu Leu Cys Cys Asn Pro Ala Cys Thr Gly Cys Tyr-COOH;

(SEQ ID NO: 6)
C14-BE BK Asn Ser Ser Tyr Cys Cys Glu Leu Cys Cys Asn Pro Ala Cys Thr Gly Cys Tyr-COOH;

(SEQ ID NO: 7)
C16-BE BK Asn Ser Ser Tyr Cys Cys Glu Leu Cys Cys Asn Pro Ala Cys Thr Gly Cys Tyr-COOH;

(SEQ ID NO: 8)
H-Cys Ag Glu Leu Cys Cys Asn Pro Ala Ag Thr Gly Cys Tyr-NH$_2$;

(SEQ ID NO: 9)
H-Asn Asp Asp Ag Glu Leu Cys Val Asn Val Ala Ag Thr Gly Cys Leu-NH$_2$;

(SEQ ID NO: 10)
H-Asn Asp Asp Cys Glu Leu Ag Val Asn Val Ala Cys Thr Gly Ag Leu-NH$_2$;

(SEQ ID NO: 11)
C18-BE BK Asn Ser Ser Tyr Cys Cys Glu Leu Cys Cys Asn Pro Ala Cys Thr Gly Cys Tyr-COOH;

```
                                                      (SEQ ID NO: 12)
H-Ag Cys Glu Leu Cys Ag Asn Pro Ala Cys Thr Gly Cys-NH2;

(SEQ ID NO: 13)
H-Ag Cys Glu Leu Cys Ag Asn Pro Ala Cys Ala Gly Cys-NH2;

(SEQ ID NO: 14)
H-Ag Cys Glu Phe Cys Ag Asn Pro Ala Cys Thr Gly Cys Tyr-NH2;

(SEQ ID NO: 15)
H-Ag Cys Glu (4-F)Phe Cys Ag Asn Pro Ala Cys Thr Gly Cys-NH2;

(SEQ ID NO: 16)
H-Ag Cys Glu (4-F)Phe Cys Ag Asn Pro Ala Cys Thr Gly Cys Tyr-NH2;

(SEQ ID NO: 17)
H-Ag Cys Glu (4-F)Phe Cys Ag Asn Pro Ala Cys Thr Gly Cys (4-F)Phe-
NH2;

(SEQ ID NO: 18)
H-Cys Cys Glu Leu Ag Cys Asn Pro Ala Cys Thr Gly Ag Tyr-NH2;

(SEQ ID NO: 19)
H-Ag Cys Glu Phe Cys Ag Asn Pro Ala Cys Thr Gly Cys-NH2;

(SEQ ID NO: 20)
H-Ag Cys Glu Phe Cys Ag Asn Pro Ala Cys Thr Gly Cys (4-F)Phe-NH2;

(SEQ ID NO: 21)
H-Cys Cys Glu (4-F)Phe Cys Cys Asn Pro Ala Cys Thr Gly Cys Tyr-NH2;

(SEQ ID NO: 22)
H-Cys Cys Glu (4-F)Phe Cys Cys Asn Pro Ala Cys Thr Gly Cys (4-F)Phe-
NH2;

(SEQ ID NO: 23)
H-Ag Cys Glu Leu Cys Ag Asn Pro Ala Cys Thr Gly Cys (4-F)Phe-NH2;

(SEQ ID NO: 24)
H-(4-F)Phe Ag Cys Glu Leu Cys Ag Asn Pro Ala Cys Thr Gly Cys (4-
F)Phe-NH2;

(SEQ ID NO: 25)
H-Ag Cys Glu Leu Cys Ag Asn Pro Ala Cys Ala Gly Cys Tyr-NH2;

(SEQ ID NO: 26)
H-Ag Cys Glu Leu Cys Ag Asn Pro Ala Cys Tyr Gly Cys Tyr-NH2;

(SEQ ID NO: 27)
H-Ag Cys Glu Leu Cys Ag Asn Pro Ala Cys Phe Gly Cys Tyr-NH2;

(SEQ ID NO: 28)
H-Ag Cys Glu Leu Cys Ag Asn Pro Ala Cys (4-F)Phe Gly Cys Tyr-NH2;

(SEQ ID NO: 29)
H-Ag Cys Glu Leu Cys Ag Asn Pro Ala Cys Thr Gly Cys Leu-NH2;

(SEQ ID NO: 30)
H-Ag Cys Glu Leu Cys Ag Asn Pro Ala Cys Thr Gly Cys Cha-NH2;

(SEQ ID NO: 31)
H-Ag Cys Glu Cha Cys Ag Asn Pro Ala Cys Thr Gly Cys Tyr-NH2;

(SEQ ID NO: 32)
H-Ag Cys Glu Leu Cys Ag Asn Pro Ala Cys Thr Gly Cys D-Tyr-NH2;

(SEQ ID NO: 33)
H-Ag Pen Glu Leu Cys Ag Asn Pro Ala Pen Thr Gly Cys Tyr-NH2;

(SEQ ID NO: 34)
H-Ag Cys Glu Leu Cys Ag Asn Pro Ala Cys Thr Gly Cys Leu Asn-NH2;

(SEQ ID NO: 35)
H-Ag Cys Glu Leu Cys Ag Asn Pro Ala Cys Thr Gly Cys Tyr Asn-NH2;

(SEQ ID NO: 36)
H-Asp Ag Cys Glu Leu Cys Ag Asn Pro Ala Cys Thr Gly Cys Tyr-NH2;
```

-continued

```
                                       (SEQ ID NO: 37)
H-Ile Asp Ag Cys Glu Leu Cys Ag Asn Pro Ala Cys Thr Gly Cys Tyr-
NH2;

(SEQ ID NO: 38)
H-Ag Cys Glu Leu Cys Ag Asn OH-Pro Ala Cys Thr Gly Cys Tyr-NH2;

(SEQ ID NO: 39)
H-Ag Cys Glu Leu Cys Ag Asn OH-Pro Ala Cys Thr Gly Cys-NH2;

(SEQ ID NO: 40)
H-Ag Cys Glu Leu Pen Ag Asn Pro Ala Cys Thr Gly Pen Tyr-NH2;

(SEQ ID NO: 41)
H-Ag Cys Glu Leu Pen Ag Asn Pro Ala Cys Thr Gly Pen Tyr-NH2;

(SEQ ID NO: 42)
H-Ag Cys Glu Leu Cys Ag Asn Pro Ala Cys Tyr Gly Cys Nme-Tyr-NH2;

(SEQ ID NO: 43)
H-Ag Cys Glu Leu Cys Ag Asn Pro Ala Cys Tyr Gly Cys-COOH;

(SEQ ID NO: 44)
H-Ag Cys Glu Leu Cys Ag Asn Pro Ala Cys Cha Gly Cys Tyr-NH2;

(SEQ ID NO: 45)
H-Ag Cys Glu Leu Cys Ag Asn Leu Ala Cys Thr Gly Cys Tyr-NH2;

(SEQ ID NO: 46)
H-Ag Cys Glu Leu Cys Ag Asn Sar Ala Cys Thr Gly Cys Tyr-NH2;

(SEQ ID NO: 47)
H-Ag Cys Glu Leu Cys Ag Asn Val Ala Cys Thr Gly Cys Tyr-NH2;

(SEQ ID NO: 48)
H-Ag Cys Glu Leu Cys Ag Asn Pro Ala Cys Tyr Gly Cys Nme-Tyr-NH2;

(SEQ ID NO: 49)
H-Ag Cys Glu Leu Cys Ag Leu Pro Ala Cys Tyr Gly Cys-COOH;

(SEQ ID NO: 50)
H-Ag Cys Asp Leu Cys Ag Asn Pro Ala Cys Tyr Gly Cys-COOH;

(SEQ ID NO: 51)
H-Ag Cys Ser Leu Cys Ag Asn Pro Ala Cys Tyr Gly Cys-COOH;

(SEQ ID NO: 52)
H-Ag Cys Thr Leu Cys Ag Asn Pro Ala Cys Tyr Gly Cys-COOH;

(SEQ ID NO: 53)
H-Hag Cys Glu Leu Cys Hag Asn Pro Ala Cys Thr Gly Cys Tyr-NH2;

(SEQ ID NO: 54)
H-Ag Cys Gln Leu Cys Ag Asn Pro Ala Cys Tyr Gly Cys-COOH;

(SEQ ID NO: 55)
H-Ag Cys Glu Leu Cys Ag Leu Pro Ala Cys Thr Gly Cys Tyr-NH2;

(SEQ ID NO: 56)
Pent-Cys Glu Leu Cys Ag Asn Pro Ala Cys Tyr Gly Cys Tyr-NH2;

(SEQ ID NO: 57)
H-Cys Cys Glu Leu Cys Ag Asn Pro Ala Cys Tyr Gly Ag-COOH;

(SEQ ID NO: 58)
Pent-Cys Glu Leu Cys Ag Asn Pro Ala Cys Tyr Gly Cys-COOH;

(SEQ ID NO: 59)
H-Hag Cys Glu Leu Cys Hag Asn Pro Ala Cys Tyr Gly Cys-COOH;

(SEQ ID NO: 60)
H-Ag Cys Glu Leu Cys Ag Asn Val Ala Cys Tyr Gly Cys Tyr-NH2;

(SEQ ID NO: 61)
H-Ag Cys Glu Leu Cys Ag Asn Val Ala Cys Tyr Gly Cys-COOH;

(SEQ ID NO: 62)
H-Cys Cth Glu Leu Cys Cys Asn Pro Ala Cys Tyr Gly Cys Tyr-NH2;
```

-continued

```
(SEQ ID NO: 63)
H-Cth Cys Glu Leu Cys Cys Asn Pro Ala Cys Tyr Gly Cys Tyr-$NH_2$;

(SEQ ID NO: 64)
H-Cth Cys Glu Leu Cys Cys Asn Pro Ala Cys Tyr Gly Cys-COOH;

(SEQ ID NO: 65)
H-Cys Cth Glu Leu Cys Cys Asn Val Ala Cys Tyr Gly Cys Tyr-$NH_2$;

(SEQ ID NO: 66)
H-Cys Cth Glu Leu Cys Cys Asn Val Ala Cys Thr Gly Cys Tyr-$NH_2$;

(SEQ ID NO: 67)
Ac-Cys Cth Glu Leu Cys Cys Asn Val Ala Cys Thr Gly Cys Tyr-$NH_2$;

(SEQ ID NO: 68)
Ac-Cys Cth Glu Leu Cys Cys Asn Pro Ala Cys Tyr Gly Cys Tyr-$NH_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;

(SEQ ID NO: 71)
Ac-Cys Cth Glu Leu Cys Cys Asn Pro Ala Cys Tyr Gly Cys-COOH;

(SEQ ID NO: 72)
H-Cys Cys Glu Leu Cys Asn Val Ala Cth Tyr Gly Cys-COOH;

(SEQ ID NO: 73)
H-Cys Cys Glu Leu Cys Cys Asn Val Ala Cth Tyr Gly Cys Tyr-$NH_2$;

(SEQ ID NO: 74)
H-Cys Cys Glu Leu Cys Cys Asn Val Ala Cth Thr Gly Cys Tyr-$NH_2$;

(SEQ ID NO: 75)
H-Cys Cys Glu Leu Cys Cth Asn Val Ala Cys Tyr Gly Cys-COOH;

(SEQ ID NO: 76)
H-Cys Cys Glu Leu Cys Cth Asn Val Ala Cys Tyr Gly Cys Tyr-$NH_2$;

(SEQ ID NO: 77)
H-Cys Cys Glu Leu Cys Cth Asn Val Ala Cys Thr Gly Cys Tyr-$NH_2$;

(SEQ ID NO: 78)
4-Mepip-Cys Cth Glu Leu Cys Cys Asn Val Ala Cys Tyr Gly Cys-COOH;

(SEQ ID NO: 79)
H-Cys Cth Glu Leu Cys Cys Asn Val Ala Cys Thr Gly Cys-COOH;

(SEQ ID NO: 80)
H-Cys Cth Glu Leu Cys Cys Asn Val Ala Cys Thr Gly Cys-$NH_2$;

(SEQ ID NO: 81)
H-Cys Cth Glu Leu Cys Cys Asn Val Ala Cys Phe Gly Cys-COOH;

(SEQ ID NO: 82)
H-Ag Ag Glu Leu Ag Ag Asn Pro Ala Ag Thr Gly Ag Tyr-COOH;

(SEQ ID NO: 83)
H-Cys Cth Glu Leu Cys Cys Asn Ala Ala Cys Thr Gly Cys Tyr-$NH_2$;

(SEQ ID NO: 84)
H-Asp Cys Glu Leu Cys Dpr Asn Val Ala Cys Thr Gly Cys Tyr-$NH_2$;

(SEQ ID NO: 85)
H-Cys Cth Glu Leu Cys Cys Asn Val Ala Cys Ser Gly Cys Tyr-$NH_2$;

(SEQ ID NO: 86)
H-Cth Glu Leu Cys Ag Asn Val Ala Cys Thr Gly Cys Tyr-$NH_2$;

(SEQ ID NO: 87)
H-Ag Cys Glu Leu Cys Ag Asn Val Ala Cys Thr Gly Cys Tyr-$NH_2$;

(SEQ ID NO: 88)
H-Ag Cys Glu Leu Cys Ag Asn Pro Ala Cys Thr Gly Cys Tyr-$NH_2$;

(SEQ ID NO: 89)
H-Cth Cys Glu Leu Cys Cys Asn Val Ala Cys Thr Gly Cys-COOH;

-continued (SEQ ID NO: 90)
H-Cth Cys Glu Leu Cys Cys Asn Val Ala Cys Thr Gly Cys Tyr-NH$_2$;

(SEQ ID NO: 91)
H-Cth Cys Glu Leu Cys Cys Asn Val Ala Cys Tyr Gly Cys Tyr-NH$_2$;
or (SEQ ID NO: 92)
H-Cys Cys Glu Leu Cys Cys Asn Val Ala Cth Tyr Gly Cys-COOH.

8. The pharmaceutical composition according to claim 7, wherein the peptide or pharmaceutically acceptable salt thereof consists of the amino acid sequence:

(SEQ ID NO: 2)
H-Ag Cys Glu Leu Cys Ag Asn Pro Ala Cys Thr Gly Cys Tyr-NH$_2$;

(SEQ ID NO: 26)
H-Ag Cys Glu Leu Cys Ag Asn Pro Ala Cys Tyr Gly Cys Tyr-NH$_2$;

(SEQ ID NO: 43)
H-Ag Cys Glu Leu Cys Ag Asn Pro Ala Cys Tyr Gly Cys-COOH;

(SEQ ID NO: 47)
H-Ag Cys Glu Leu Cys Ag Asn Val Ala Cys Thr Gly Cys Tyr-NH$_2$;

(SEQ ID NO: 62)
H-Ag Cys Glu Leu Cys Ag Asn Val Ala Cys Tyr Gly Cys Tyr-NH$_2$;

(SEQ ID NO: 64)
H-Cth Cys Glu Leu Cys Cys Asn Pro Ala Cys Tyr Gly Cys-COOH;

(SEQ ID NO: 68)
Ac-Cys Cth Glu Leu Cys Cys Asn Pro Ala Cys Tyr Gly Cys Tyr-NH$_2$;

(SEQ ID NO: 69)
Ac-Cys Cth Glu Leu Cys Cys Asn Val Ala Cys Tyr Gly Cys-COOH;

(SEQ ID NO: 70)
H-Cys Cth Glu Leu Cys Cys Asn Val Ala Cys Tyr Gly Cys-COOH;
or (SEQ ID NO: 71)
Ac-Cys Cth Glu Leu Cys Cys Asn Pro Ala Cys Tyr Gly Cys-COOH.

9. The pharmaceutical composition according to claim 8, wherein the pharmaceutical composition is a solid dosage formulation, or an oral solid dosage formulation.

10. The peptide or pharmaceutically acceptable salt thereof according to claim 1, wherein the peptide comprises the amino acid sequence: (SEQ ID NO: 2) H-Ag Cys Glu Leu Cys Ag Asn Pro Ala Cys Thr Gly Cys Tyr-NH$_2$.

11. The peptide or pharmaceutically acceptable salt thereof according to claim 1, wherein the peptide comprises the amino acid sequence: (SEQ ID NO: 26) H-Ag Cys Glu Leu Cys Ag Asn Pro Ala Cys Tyr Gly Cys Tyr-NH$_2$.

12. The peptide or pharmaceutically acceptable salt thereof according to claim 1, wherein the peptide comprises the amino acid sequence: (SEQ ID NO: 43) H-Ag Cys Glu Leu Cys Ag Asn Pro Ala Cys Tyr Gly Cys-COOH.

13. The peptide or pharmaceutically acceptable salt thereof according to claim 1, wherein the peptide comprises the amino acid sequence: (SEQ ID NO: 47) H-Ag Cys Glu Leu Cys Ag Asn Val Ala Cys Thr Gly Cys Tyr-NH$_2$.

14. The peptide or pharmaceutically acceptable salt thereof according to claim 1, wherein the peptide comprises the amino acid sequence: (SEQ ID NO: 62) H-Cys Cth Glu Leu Cys Cys Asn Pro Ala Cys Tyr Gly Cys Tyr-NH$_2$.

15. The peptide or pharmaceutically acceptable salt thereof according to claim 1, wherein the peptide comprises the amino acid sequence: (SEQ ID NO: 64) H-Cth Cys Glu Leu Cys Cys Asn Pro Ala Cys Tyr Gly Cys-COOH.

16. The peptide or pharmaceutically acceptable salt thereof according to claim 1, wherein the peptide comprises the amino acid sequence: (SEQ ID NO: 68) Ac-Cys Cth Glu Leu Cys Cys Asn Pro Ala Cys Tyr Gly Cys Tyr-NH$_2$.

17. The peptide or pharmaceutically acceptable salt thereof according to claim 1, wherein the peptide comprises the amino acid sequence: (SEQ ID NO: 69) Ac-Cys Cth Glu Leu Cys Cys Asn Val Ala Cys Tyr Gly Cys-COOH.

18. The peptide or pharmaceutically acceptable salt thereof according to claim 1, wherein the peptide comprises the amino acid sequence: (SEQ ID NO: 70) H-Cys Cth Glu Leu Cys Cys Asn Val Ala Cys Tyr Gly Cys-COOH.

19. The peptide or pharmaceutically acceptable salt thereof according to claim 1, wherein the peptide comprises the amino acid sequence: (SEQ ID NO: 71) Ac-Cys Cth Glu Leu Cys Cys Asn Pro Ala Cys Tyr Gly Cys-COOH.

20. A pharmaceutical composition comprising a peptide or a pharmaceutically acceptable salt thereof according to claims 1.

21. The pharmaceutical composition according to claim 20, wherein the peptide or a pharmaceutically acceptable salt thereof is (SEQ ID NO: 2) H-Ag Cys Glu Leu Cys Ag Asn Pro Ala Cys Thr Gly Cys Tyr-NH$_2$.

22. The pharmaceutical composition according to claim 20, wherein the peptide or a pharmaceutically acceptable salt thereof is (SEQ ID NO: 26) H-Ag Cys Glu Leu Cys Ag Asn Pro Ala Cys Tyr Gly Cys Tyr-NH$_2$.

23. The pharmaceutical composition according to claim 20, wherein the peptide or a pharmaceutically acceptable salt thereof is (SEQ ID NO: 43) H-Ag Cys Glu Leu Cys Ag Asn Pro Ala Cys Tyr Gly Cys-COOH.

24. The pharmaceutical composition according to claim 20, wherein the peptide or a pharmaceutically acceptable salt thereof is (SEQ ID NO: 47) H-Ag Cys Glu Leu Cys Ag Asn Val Ala Cys Thr Gly Cys Tyr-NH$_2$.

25. The pharmaceutical composition according to claim 20, wherein the peptide or a pharmaceutically acceptable salt thereof is (SEQ ID NO: 62) H-Cys Cth Glu Leu Cys Cys Asn Pro Ala Cys Tyr Gly Cys Tyr-NH$_2$.

26. The pharmaceutical composition according to claim 20, wherein the peptide or a pharmaceutically acceptable salt thereof is (SEQ ID NO: 64) H-Cth Cys Glu Leu Cys Cys Asn Pro Ala Cys Tyr Gly Cys-COOH.

27. The pharmaceutical composition according to claim 20, wherein the peptide or a pharmaceutically acceptable salt thereof is (SEQ ID NO: 68) Ac-Cys Cth Glu Leu Cys Cys Asn Pro Ala Cys Tyr Gly Cys Tyr-NH$_2$.

28. The pharmaceutical composition according to claim 20, wherein the peptide or a pharmaceutically acceptable salt thereof is (SEQ ID NO: 69) Ac-Cys Cth Glu Leu Cys Cys Asn Val Ala Cys Tyr Gly Cys-COOH.

29. The pharmaceutical composition according to claim 20, wherein the peptide or a pharmaceutically acceptable salt thereof is (SEQ ID NO: 70) H-Cys Cth Glu Leu Cys Cys Asn Val Ala Cys Tyr Gly Cys-COOH.

30. The pharmaceutical composition according to claim 20, wherein the peptide or a pharmaceutically acceptable salt thereof is (SEQ ID NO: 71) Ac-Cys Cth Glu Leu Cys Cys Asn Pro Ala Cys Tyr Gly Cys-COOH.

* * * * *